United States Patent
Chen et al.

(10) Patent No.: US 10,415,026 B2
(45) Date of Patent: *Sep. 17, 2019

(54) COMPLEMENT FACTOR B ANALOGS AND THEIR USES

(71) Applicant: Wellstat ImmunoTherapeutics, LLC, Gaithersburg, MD (US)

(72) Inventors: ChangHung Chen, Germantown, MD (US); Michael Kaleko, Rockville, MD (US); Beibei Li, Potomac, MD (US); Tianci Luo, Clarksville, MD (US); Jeffrey Allan Miller, Lincoln University, PA (US); Ruigong Wang, Frederick, MD (US)

(73) Assignee: Wellstat ImmunoTherapeutics, LLC, Rockville, MD (US)

( * ) Notice: Subject to any disclaimer, the term of this patent is extended or adjusted under 35 U.S.C. 154(b) by 39 days.

This patent is subject to a terminal disclaimer.

(21) Appl. No.: 15/334,339

(22) Filed: Oct. 26, 2016

(65) Prior Publication Data

US 2017/0037391 A1 Feb. 9, 2017

Related U.S. Application Data

(62) Division of application No. 14/951,565, filed on Nov. 25, 2015, now Pat. No. 9,533,028, which is a division of application No. 14/115,115, filed as application No. PCT/US2012/036459 on May 4, 2012, now Pat. No. 9,228,003.

(60) Provisional application No. 61/497,835, filed on Jun. 16, 2011, provisional application No. 61/482,827, filed on May 5, 2011, provisional application No. 61/568,518, filed on Dec. 8, 2011.

(51) Int. Cl.
| | |
|---|---|
| *C12N 9/64* | (2006.01) |
| *C07K 16/18* | (2006.01) |
| *C07K 16/40* | (2006.01) |
| *C07K 14/47* | (2006.01) |
| *A61K 38/48* | (2006.01) |

(52) U.S. Cl.
CPC .......... *C12N 9/6424* (2013.01); *A61K 38/482* (2013.01); *C07K 14/472* (2013.01); *C07K 16/18* (2013.01); *C07K 16/40* (2013.01); *C12Y 304/21047* (2013.01); *C07K 2319/30* (2013.01); *Y02A 50/473* (2018.01)

(58) Field of Classification Search
None
See application file for complete search history.

(56) References Cited

U.S. PATENT DOCUMENTS

| | | |
|---|---|---|
| 6,753,165 B1 | 6/2004 | Cox |
| 9,228,003 B2 | 1/2016 | Chen et al. |
| 2006/0074225 A1 | 4/2006 | Chamberlain |
| 2007/0104689 A1 | 5/2007 | Gillies et al. |
| 2009/0081182 A1 | 3/2009 | Boone et al. |
| 2009/0269804 A1 | 10/2009 | Rosendahl |
| 2010/0120665 A1 | 5/2010 | Kaleko |
| 2010/0239573 A1 | 9/2010 | Bansal |
| 2011/0311584 A1 | 12/2011 | Sahin |
| 2012/0263707 A1 | 10/2012 | Hill |

FOREIGN PATENT DOCUMENTS

| | | |
|---|---|---|
| RU | 2417099 C2 | 4/2011 |
| WO | 2007056227 A2 | 5/2007 |
| WO | 2008106644 A2 | 9/2008 |
| WO | 2010066418 A1 | 6/2010 |
| WO | 2010085682 A2 | 7/2010 |

OTHER PUBLICATIONS

GenBank GU441459.1 (< https://www.ncbi.nlm.nih.gov/nuccore/GU441459> Mar. 1, 2010).*
Ricklin et al., "Complement—a key system for immune surveillance and homeostatis", Nature Immunol. 11(9): 785-797. Sep. 2010.
Petersen et al., "Amino acid neighhbours and detailed conformational analysis of cysteines in proteins", Protein Engineering. 12(7): 535-548. 1999.
Hourcade, et al., "Analysis of the Short Consensus Repeats of Human Complement Factor B by Site-Directed Mutagenesis", J. Biol. Chem. 270(34):19716-19722. Aug. 25, 1995.
Hourcade, et al., "Mutations of the Type A Domain of Complement Factor B that Promote High-Affinity C3b-Binding", J. Immunol. 162:2906-2911. 1999.
Christie, et al., "Amino acid sequence of the Bb fragment from complement Factor B", Biochemical J., 209:61-70. 1983.
Colombatti, et al., "The Superfamily of Proteins With von Willebrand Factor Type A-Like Domains: One theme Common to Components of Extracellular Matrix, Hemostasis, Cellular Adhesion, and Defense Mechanisms", Blood, 77 (11):2305-2315. Jun. 1, 1991.
Gros, et al., "Complement driven by conformational changes", Nature Review Immunol., 8:48-58. Jan. 2008.
Harris, et al., "Decay-Accelerating Factor Must Bind Both Components of the Complement Alternative Pathway C3 Convertase to Mediate Efficient Decay," J. Immunol., 178:352-359. 2007.
Hourcade, et al., "A Conserved Element in the Serine Protease Domain of Complement Factor B", J. Biol. Chem., 273(40): 25996-26000. Oct. 2, 1998.

(Continued)

*Primary Examiner* — James H Alstrum-Acevedo
*Assistant Examiner* — Tara L Martinez
(74) *Attorney, Agent, or Firm* — Lewis J. Kreisler

(57) ABSTRACT

The invention provides polypeptides comprising a complement factor B analog. The invention also provides various complement factor B analogs including complement factor B analogs comprising a mutation of a free cysteine amino acid and related methods, nucleic acids and vectors. These complement factor B analogs and related methods, nucleic acids and vectors can be used to modulate a complement pathway or for the study and/or treatment of various conditions or diseases related to a complement pathway.

18 Claims, 11 Drawing Sheets

Specification includes a Sequence Listing.

(56) References Cited

OTHER PUBLICATIONS

Mole, et al., "Complete primary structure for the zymogen of human complement factor B", J. Biol. Chem., 259:3407-3412. 1984.

Parkes, et al., "The reaction of iodine and thiol-blocking reagents with human complement components C2 and Factor 8", Biochem. J. 213: 201-209. 1983.

Perkins, et al., "Identity of the putative serine-proteinase fold in proteins of the complement system with nine relevant crystal structures", Biochem. J., 295: 109-114. 1993.

Xu, et al., "Mutational Analysis of the Primary Substrate Specificity Pocket of Complement Factor B", J. Biol. Chem., 275: 378-385. 2000.

Ponnuraj, et al., "Structural Analysis of Engineered Bb Fragment of Complement Factor B: Insights into the Activation Mechanism of the Alternative Pathway C3-Convertase", Molecular Cell, 14: 17-28. Apr. 9, 2004.

Kristensen, et al., "The superfamily of C3b/C4b-binding proteins", Fed Proc., 46(7):2463. May 15, 1987 (abstract).

Lesavre et al., "Inhibition of alternative pathway factor D by factor B-related synthetic hexapeptides", Eur. J. Immunol., 12(3): 252-254, 1982.

Tatara et al., "A single free cysteine residue and disulfide bond contribute to the thermostability of Aspergillus saitoi 1,2-alpha-Mannosidase", Biosci. biotechnol. Biochem., 69(11): 2101-2108, 2005.

Lee and Blaber, "Structural basis of conserved cysteine in the fibroblast growth factor family: evidence for a vestigial half-cystine", J. Mol. Biol., 393: 128-139, 2009.

Sequence Listing of WO 2008/106644 A2, published Sep. 4, 2008.

Williams et al., "Production and functional activity of a recombinant von Willebrand factor-A domain from human complement factor B", Biochem. J. 342: 625-632. 1999.

Hourcade et al., "Decay-accelerating Factor (DAF), Complement Receptor 1 (CR1), and Factor H Dissociate the Complement AP C3 Convertase (C3bBb) via Sites on the Type A Domain of Bb", J. Biol. Chem. 277(2): 1107-1112. Jan. 11, 2002.

Holers, "The spectrum of complement alternative pathway-mediated diseases", Immunol. Rev., 223: 300-316. 2008.

Malik et al., "The alternative pathway is critical for pathogenic complement activation in endotoxin- and diet-induced atherosclerosis in low-density lipoprotein receptor-deficient mice", Circulation, 122(9): 1948-1956. Nov. 9, 2010.

Kallenberg et al., "Review: Complement system activation in ANCA: vasculitis: A translational success story?", Mol. Immunol., 68: 53-56. 2015.

Kang et al., "The role of the alternative complement pathway in early graft loss after intraportal porcine islet xenotransplantation", Transplantation, 97(10): 999-1008. May 27, 2014.

Lepock et al., "Contribution of conformational stability and reversibility of unfolding to the increased thermostability of human and bovine superoxide dismutase mutated at free cysteines", J. Biol. Chem., 265(35): 21612-21618. Dec. 15, 1990.

Gold et al., "Variation in factor B (BF) and complement component 2 (C2) genes is associated with age-related macular degeneration", Nature Genetics, 38(4): 458-462. Published online Mar. 5, 2006; doi:10.1038/ng1750.

Noris et al., "Overview of complement activation and regulation", Semin Nephrol., 33(6): 479-492. Nov. 2013.

Allowed claims in U.S. Appl. No. 14/951,565 (dated Oct. 6, 2016).

\* cited by examiner

Group 1

Group 2

Group 3

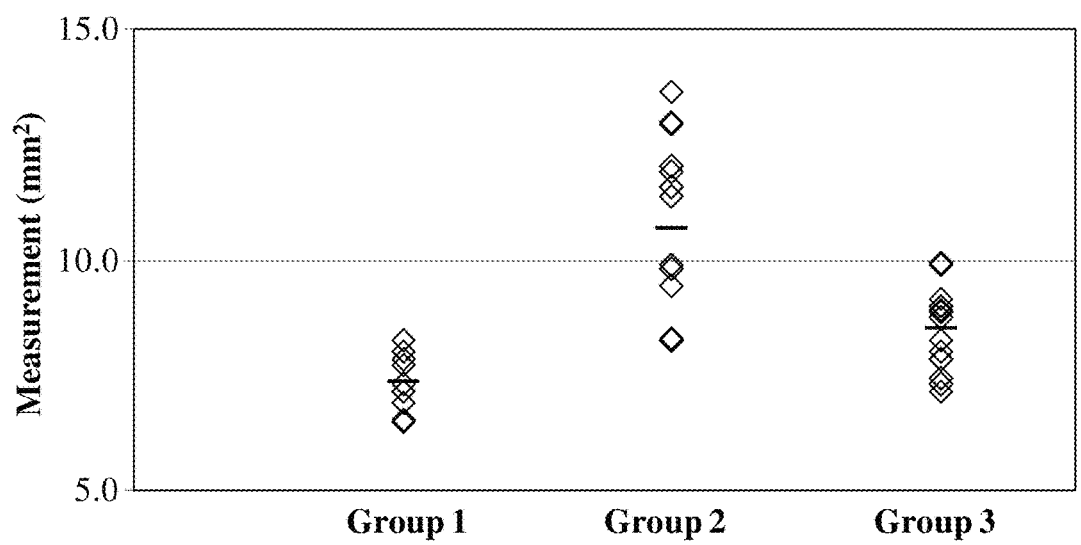
Figure 10
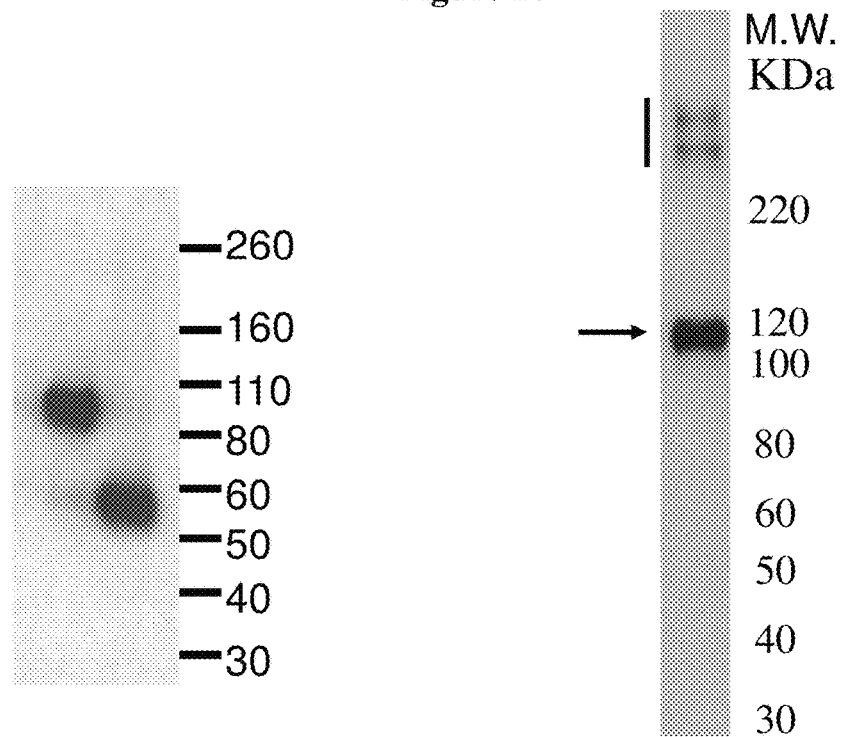
Figure 11
Figure 12

COMPLEMENT FACTOR B ANALOGS AND THEIR USES

BACKGROUND OF THE INVENTION

The complement system is a component of the innate and adaptive immune system (reviewed by Volanakis, J. E., 1998. Chapter 2. In *The Human Complement System in Health and Disease*. Edited by J. E. Volanakis, and M. M. Frank. Marcel Dekker, Inc., New York pp 9-32). Complement plays an important role in microbial killing, and for the transport and clearance of immune complexes. Many of the activation products of the complement system are also associated with proinflammatory or immunoregulatory functions. The complement system consists of plasma and membrane-associated proteins that are organized in three enzymatic-activation cascades: the classical, the lectin, and the alternative pathways (FIG. 1). All three pathways can lead to the formation of the terminal complement complex (TCC) and an array of biologically active products.

In some cases, complement activation is initiated either by specific antibodies recognizing and binding to a variety of pathogens and foreign molecules, and/or by direct interaction of complement proteins with foreign substances. On activation, these pathways result in the formation of protease complexes, the C3-convertases. The classical pathway C3-convertase, C4b2a, and the alternative pathway C3-convertase, C3bBb, are both able to cleave the α chain of C3 generating C3b. C3b has the potential to bind covalently to biological surfaces. C3b binding leads to opsonization for phagocytosis by polymorphonuclear cells and macrophages. When additional C3b is available, the C3-convertases can function as C5-convertases, cleaving C5 and initiating the assembly of the TCC, or membrane attack complex (MAC), which mediates cellular lysis by insertion of pore-forming protein complexes into targeted cell membranes.

In the classical pathway as shown in FIG. 1A, C1q, a collagenous subcomponent of the first component (C1), binds to immunoglobulins within immune complexes, and its associated serine proteases, C1r and C1s, become activated. This complement cascade is initiated by the subsequent cleavage of C4 and C2, followed by C3 activation. The resulting C3b fragment not only acts as an opsonin but also leads to the membrane attack complex (MAC) formation in the lytic pathway. In innate immunity, a complex composed of a recognition molecule (lectin) and serine proteases, termed the mannose-binding lectin (MBL)-associated serine protease (MASP), activates C4 and C2 upon binding to carbohydrates on the surface of microorganisms via the lectin pathway. This binding occurs in the absence of immunoglobulins. Recognition molecules of the lectin pathway found in jawed vertebrates are MBLs and ficolins, both of which are characterized by the presence of a collagen-like domain, like C1q, and a carbohydrate binding domain having a common binding specificity for GlcNAc. MASPs and C1r/C1s share the same domain organization and form a subfamily of serine proteases.

The lectin complement pathway in innate immunity is closely related to the classical complement pathway in adaptive immunity, e.g., with respect to the structures and functions of their components. Both pathways are typically initiated by complexes consisting of collagenous proteins and serine proteases of the mannose-binding lectin (MBL)-associated serine protease (MASP)/C1r/C1s family. It has been speculated that the classical pathway emerged evolutionarily after the lectin pathway.

Activation of the alternative complement pathway, shown in FIG. 1B, typically begins when C3b protein (or C3i) binds to a cell and other surface components, e.g., of microbes. C3b can also bind to immunoglobulin G (IgG) antibodies. Alternative pathway Factor B protein then combines with the C3b protein to form C3bB. Factor D protein then splits the bound Factor B protein into fragments Bb and Ba, forming C3bBb. Properdin then binds to the Bb to form C3bBbP that functions as a C3 convertase capable of enzymatically splitting typically hundreds of molecules of C3 into C3a and C3b. Some of the C3b subsequently binds to some of the C3bBb to form C3bBbC3b, a C5 convertase capable of splitting molecules of C5 into C5a and C5b.

Since C3b is free in the plasma, it can bind to either a host cell or pathogen surface. To prevent complement activation from proceeding on the host cell, there are several different kinds of regulatory proteins that disrupt the complement activation process. Complement Receptor 1 (CR1 or CD35) and DAF (also known as CD55) compete with Factor B in binding with C3b on the cell surface and can even remove Bb from an already formed C3bBb complex. The formation of a C3 convertase can also be prevented when a plasma protease called Factor I cleaves C3b into its inactive form, iC3b. Factor I works with C3b-binding protein cofactors such as CR1 and Membrane Cofactor of Proteolysis (MCP or CD46). Another complement regulatory protein is Factor H which either competes with factor B, displaces Bb from the convertase, acts as a cofactor for Factor I, or preferentially binds to C3b bound to vertebrate cells.

The precise function of the complement system depends on its regulation, as activation of the complement cascade leads to the production of a number of proteins that contribute to inflammation. This is beneficial when contributing to a host defense, but can be detrimental if activated on self tissue. Typically, activation of C3 in the blood is kept at a low level, and C3b deposition is limited to the surface of pathogens.

The human wild type complement factor B protein is a 764 amino acid, single-chain glycoprotein (approximately 93-kDa) composed of five protein domains (Mole et al., 1984 The J. Biol Chem, 259:6, 3407-3412). A human wild type complement factor B protein (fB) is typically expressed with an N-terminal 25 amino acid signal peptide, e.g., see SEQ ID NO: 1. The amino-terminal region (Ba) of human wild type complement factor B protein consists primarily of three short consensus repeats. The middle region is a type A domain similar to those found in von Willebrand factor (Colombatti et al., Blood (1991) 77(11):2305-15). The carboxy terminus is a serine protease (SP) domain (Perkins and Smith, Biochem J. (1993) 295(Pt 1):109-14; Hourcade et al., JBC (1998) 273(40):25996-6000; Hourcade et al. J Immunol. (1999) 162(5):2906-11; Xu et al., J Biol Chem. 2000 275(1):378-85; Milder et al. Nat Struct Mol Biol (2007) 14(3):224-8).

Complement factor B analogs and their use for inhibiting complement and treating complement mediated diseases are described in PCT Publication No. WO08/106644 and U.S. Patent Publication No. US20100120665. For example, the human complement factor B protein analog, hfB3 (described in U.S. Patent Publication No. 20100120665), is a dominant negative human factor B protein variant that efficiently inhibits the alternative complement (AP) activity. hfB3 protein (SEQ ID NO:4) has five amino acid changes compared to a human wild type factor B protein (SEQ ID NO:1). The five amino acid changes enable hfB3 protein to (i) bind much tighter to C3b protein, (ii) resist C3b-dependent cleavage by factor D protein, and (iii) bind tighter to factor D protein when compared to the wild type factor B protein. The tighter binding of hfB3 protein with C3b protein and factor D protein sequester two essential components of the alternative complement pathway (ACP) in an inactive C3 convertase (hfB3), blocking the AP activity. Since C3b-bound hfB3 protein cannot be cleaved by factor D protein, the conformational change of hfB3 protein does not occur and the serine protease at the C-terminus of hfB3 protein is not activated.

Both human wild type complement factor B protein and hfB3 contain 23 cysteine amino acids. The "active" forms of both have all of the cysteines forming disulfide bonds with one of the other cysteines, with the exception of the cysteine corresponding to the C292 of SEQ ID NO: 1. The C292 of the "active forms" of hfB3 and wild type factor B is a free cysteine (Parkes et al. 1983 Biochem J. 213, 201-209) and is highly conserved among various mammalian species, e.g., see Table 1, below.

Citation or discussion of a reference herein shall not be construed as an admission that such is prior art to the present invention.

SUMMARY OF THE INVENTION

The invention provides polypeptides comprising a complement factor B analog. The invention also provides various complement factor B analogs. In some embodiments, a complement factor B analog comprises a mutation of a free cysteine amino acid. The invention also provides nucleic acids and viral vectors comprising a nucleotide sequence encoding polypeptides and complement factor B protein analogs of the invention. Some embodiments of the invention provide cells, wherein the cells comprise a nucleic acid encoding a complement factor B protein analog of the invention and wherein the cells express a complement factor B protein analog.

Additionally, the invention provides pharmaceutical preparations comprising a polypeptide or complement factor B protein analog of the invention, a nucleic acid of the invention, a viral vector of the invention or any combination thereof.

Also provided by the present invention are methods of treating a complement-mediated disease comprising administering to a patient a pharmaceutical preparation of the invention, a polypeptide of the invention, a complement factor B protein analog of the invention, a nucleic acid of the invention, a viral vector of the invention or any combination thereof.

The invention also provides methods of producing a polypeptide comprising a complement factor B protein analog, the method comprising: expressing in a cell a complement factor B protein analog of the invention and purifying said complement factor B protein analog.

Polypeptides of the invention, complement factor B analogs of the invention, and nucleic acids and vectors encoding them, can be used to modulate a complement pathway and for the study and/or treatment of various conditions or diseases related to a complement pathway.

The invention is based on the findings that mutation or removal of a free cysteine (i) improves the yield of an active and/or properly folded complement factor B protein analog (e.g., see Examples 9 and 10); (ii) enhances the thermostability of a complement factor B protein analog (e.g., see Examples 13 and 14); and/or (iii) reduces aggregation of a complement factor B protein analog (e.g., see Example 6).

This summary of the invention does not necessarily describe all features or necessary features of the invention. The invention may also reside in a sub-combination of the described features.

BRIEF DESCRIPTION OF THE FIGURES

For the purpose of illustrating the invention, there are depicted in the drawings certain embodiments of the invention. However, the invention is not limited to the precise arrangements and instrumentalities of embodiments depicted in the drawings.

FIG. 1A depicts the classical and lectin complement pathways. The classical pathway is initiated through C1 while the lectin pathway is initiated through mannose binding lectin (MBL). C4bC2a is a protease that cleaves C3 to C3a and C3b and is termed the C3 convertase. Similarly, C4bC2aC3b cleaves C5 to C5a and C5b and is termed the C5 convertase. C3a, C4a, and C5a have inflammatory properties and attract phagocytotic cells. C5b6-9 forms the membrane attack complex (MAC), which creates membrane pores that kill infectious agents but can also damage host cells. MASP is mannan-binding lectin associated serine protease.

FIG. 1B depicts the alternative complement pathway. This pathway is constitutively active at a low level through spontaneous cleavage of C3. In the presence of an appropriate surface, C3b binds to complement factor B (fB). This complex is then cleaved by complement factor D (fD) to yield C3bBb. Spontaneous dissociation ("decay") of this complex within minutes leads to its inactivation, whereas stabilization by properdin generates a complex that cleaves C3; that is, a C3 convertase. Several of the factors that attenuate the complement pathways do so by accelerating the decay of the C3 and C5 convertases. C3b participates in the C3 convertase to generate additional C3b thereby creating a positive feedback loop as shown by the large arrow. C3bBb is a C3 convertase. C3bBbC3b is a C5 convertase.

FIG. 2 is a hfB3-292S expression construct. CMV-cytomegalovirus immediate early promoter; IRES-internal ribosomal entry site; Neo-neomycin phosphotransferase gene; SynPolyA-synthetic polyA; Amp-Ampicillin-resistant gene. SEQ ID NO:8 is the nucleotide sequence of the hfB3-292S expression construct shown in FIG. 2.

FIG. 3 shows Western blot analysis of raw cell culture supernatants containing either hfB3 or hfB3-292S protein after cell culture incubation for 72 hour ($2\times10^6$ cells/mL). Lane 1, one μl of cell culture medium from naïve untransfected 293 FreeStyle cells served as a negative control; Lane 2, one hundred ng of human wild type factor B (Quidel, Santa Clara, Calif.) purified from plasma served as a positive control; Lane 3, one μl of cell culture medium from hfB3 producing cells; Lane 4, one μl of cell culture medium from hfB3-292S producing cells. The molecular weight markers in KDa are indicated on the right.

FIG. 4 shows the results of a hemolytic assay. These results demonstrate inhibition of human alternative complement pathway hemolytic activity by raw hfB3 protein or hfB3-292S protein producing cell culture medium. The relative hemolytic activity is scored by hemoglobin released after hemolysis of rRBCs by human alternative complement pathway activity. X-axis from left to right: factor B-depleted human serum supplemented with 0 μg of purified human factor B protein (control, no lysis of rRBCs); factor B-depleted human serum supplemented in each reaction with a mixture of 0.5 μg of purified human factor B protein and 1.0, 0.5, 0.25 or 0.125 μg of hfB3 protein or hfB3-292S protein, as indicated, from the culture medium of hfB3 protein or hfB3-292S protein producing cells. Note: 100% inhibition represented no lysis of rRBCs. The Y-axis represents mean OD405 and Standard Deviation (SD).

FIG. 5A shows hfB3 protein (200 ng), purified from a three step chromatography process, subjected to SDS-PAGE and silver staining analysis. FIG. 5B shows inhibition of human alternative complement pathway hemolytic activity by the purified hfB3 protein. X-axis from left to right: factor B protein-depleted human serum supplemented with 0 μg of purified wild type human factor B protein (wt hfB) (control, no lysis of rRBCs); factor B protein-depleted human serum supplemented in each reaction with a mixture of 0.5 μg of purified wild type human factor B protein and 1.0, 0.5, 0.3, 0.2, 0.1 or 0.05 μg of hfB3, as indicated. 100% inhibition represents no lysis of rRBCs. The Y-axis represents mean OD405 and SD.

FIG. 6 shows biological activity of two populations of hfB3 protein. Shown are the results for hydrophobic interaction chromatography (HIC) purified hfB3 protein from Peak I and Peak II for inhibition of human alternative complement pathway hemolytic activity. X-axis from left to right: factor B protein-depleted human serum supplemented with 0 μg of purified human factor B protein (control, no rRBCs lysis); factor B protein-depleted human serum supplemented in each reaction with a mixture of 0.5 μg of purified wild type human factor B protein and various amounts of hfB3 protein ranging from 1.0 to 0.05 μg. 100% inhibition represents no lysis of rRBCs. The Y-axis represents mean OD405 and SD.

FIG. 7A shows reverse phase high-pressure liquid chromatography (HPLC) of raw cell culture supernatants containing either hfB3 protein or hfB3-292S protein after tissue culture incubation for 72 hours ($2 \times 10^6$ cells/mL). Supernatants from hfB3 producing cells ( . . . ), hfB3-292S protein producing cells (_____) and naïve 293 cells (_ _ _ _), were applied to an Agilent HP1100 HPLC system using a narrow bore Jupiter™ C4 column (Phenomenex) and eluted with a 50 minute water/acetonitrile (25-70% acetonitrile) gradient containing 0.1% TFA. Elution was monitored at 215 nm with a PDA detector. The position of heat shock 70 protein (HSP70), present in all three samples, is also shown.

Figure 9:
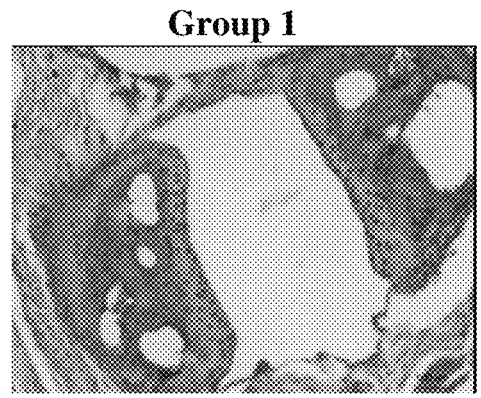
Figure 9:
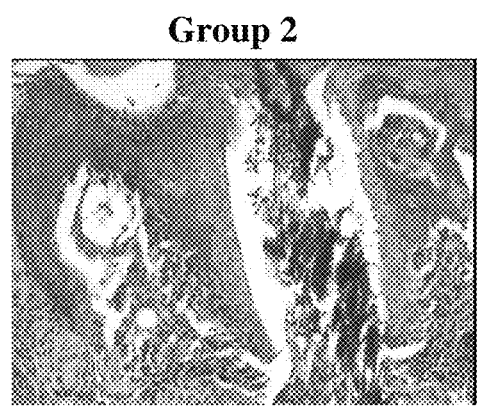
Figure 9:
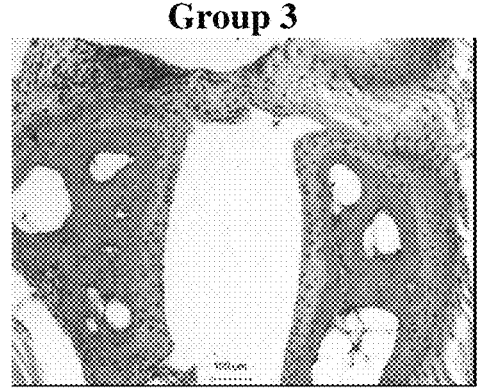

FIG. 9 shows representative H&E staining of paraffin sections of the right front paw joints of mice from a study testing hfB3-292S in a collagen antibody-induced arthritis (CAIA) mouse model for rheumatoid arthritis as described in Example 16. Group 1 is the vehicle control group that received no collagen antibody cocktail. Group 2 is the untreated group that received the collagen antibody cocktail. Group 3 is the treated group that received the collagen antibody cocktail and was treated with hfB3-292S.

FIG. 10 shows joint swelling measurements from a study testing hfB3-292S in a collagen antibody-induced arthritis (CAIA) mouse model for rheumatoid arthritis as described in Example 16. The groups are the same as those in FIG. 8, as described in the paragraph. hfB3-292S caused a statistically significant (p<0.0003) reduction in joint swelling as compared to the untreated group (Group 2).

FIG. 11 shows a Western blot analysis of cell culture medium from cells transfected with an hfB3-292SN480 expression construct. This Western blot analysis was performed using a monoclonal antibody specific for hfB3-292S. The left lane contains hfB3-292S and the right lane is cell culture medium from cells transfected with an hfB3-292SN480 expression construct. The analysis detected a band of approximately 55 KDa from the cell culture medium of hfB3-292SN480 cell line (right lane).

FIG. 12 shows a Western blot analysis of cell culture medium from cells transfected with an hfB3-292S/Fc-mono expression construct as described in Example 19, below. A band of approximately 115 KDa was detected by purified goat anti-human factor B antibody from this non-reducing SDS-PAGE.

Figure 13:
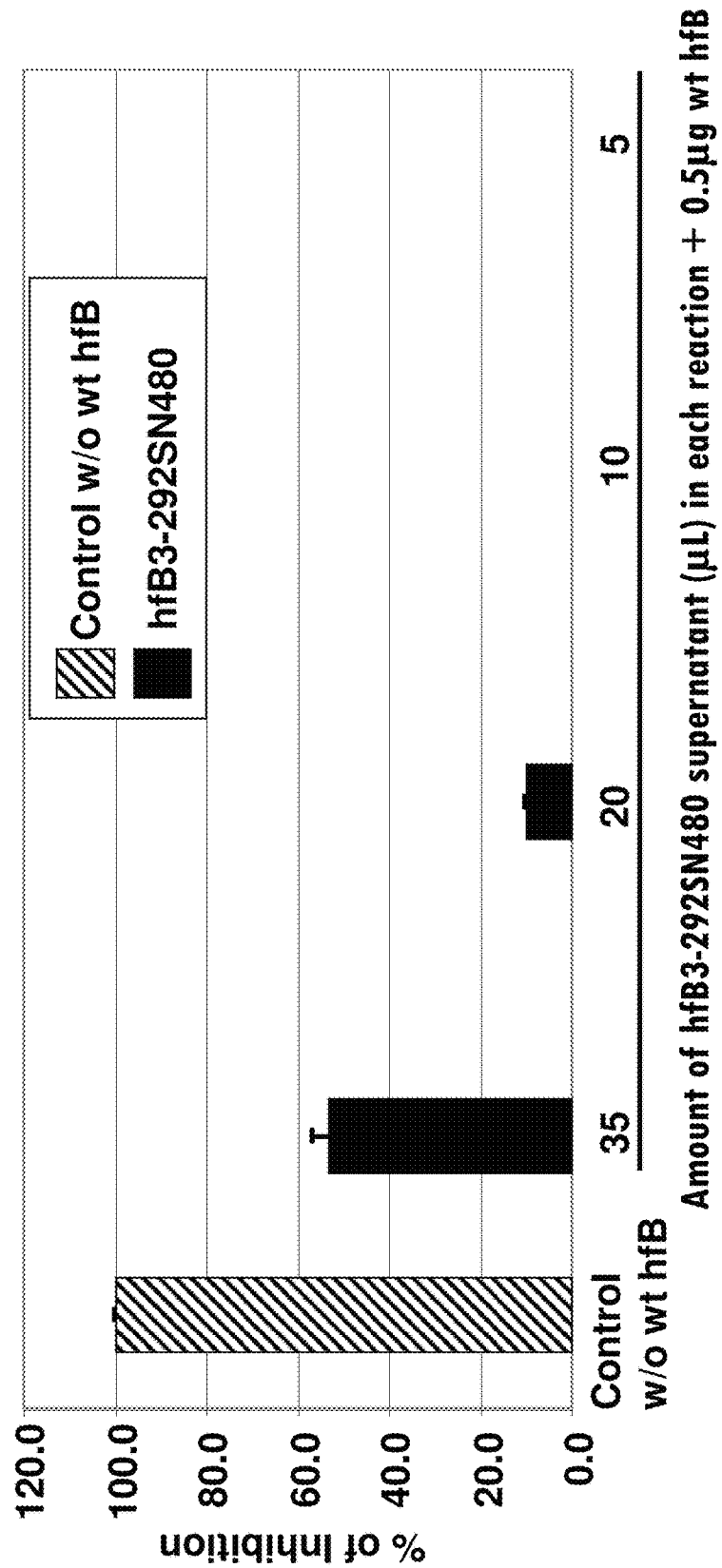

FIG. 13 shows the cell culture supernatant from cells expressing hfB3-292SN480 inhibited the human alternative complement pathway hemolytic activity in a dose dependent manner.

Figure 14:
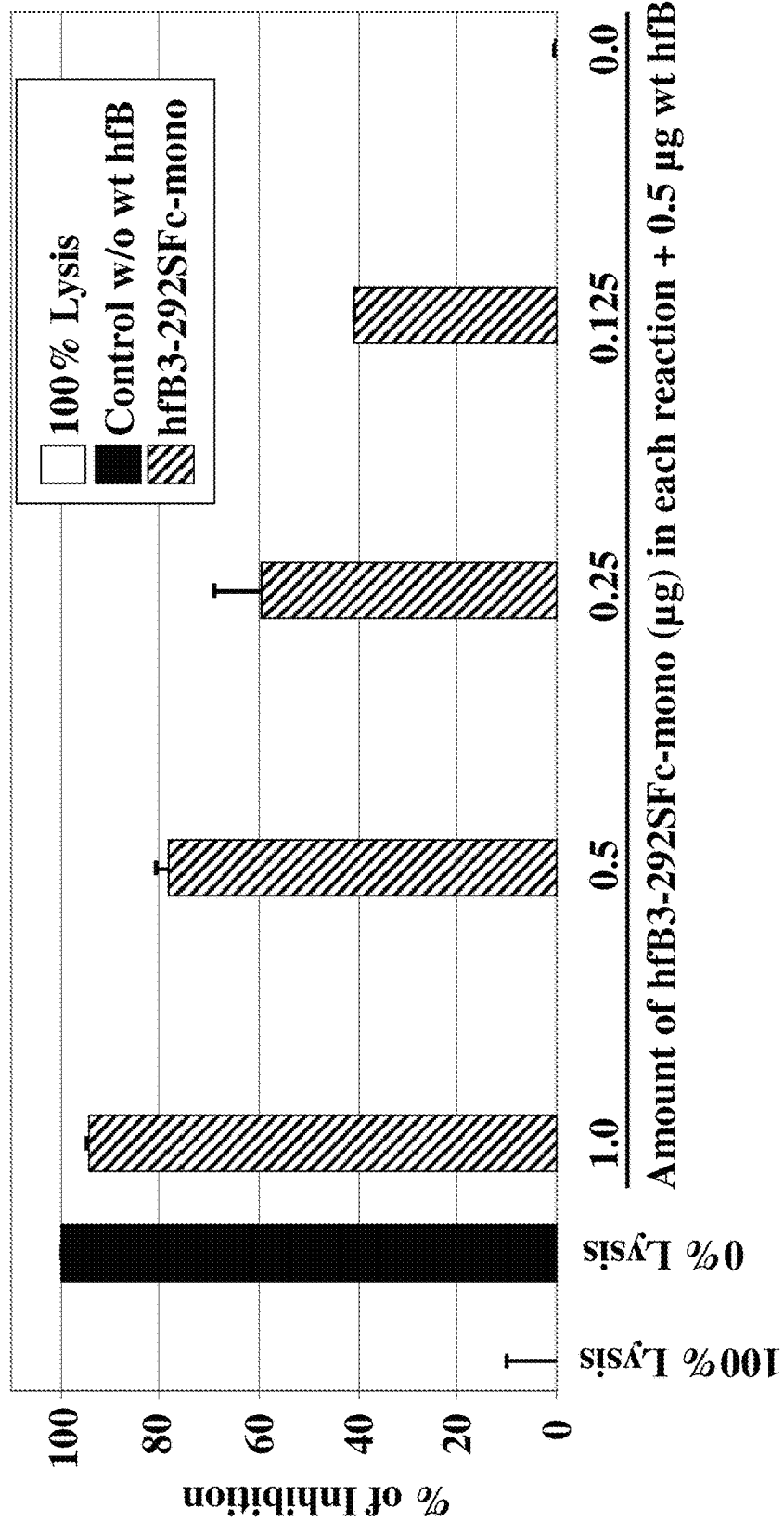

FIG. 14 shows the cell culture supernatant from cells expressing hfB3-292S/Fc-mono inhibited the human alternative complement pathway hemolytic activity in a dose-dependent manner.

BRIEF DESCRIPTION OF THE SEQUENCES

SEQ ID NO:1—amino acid sequence of a wild-type human complement factor B

SEQ ID NO:2—amino acid sequence of a human complement factor B protein analog, hfB3-292S, which comprises the following mutations: K258A, R259A, K260A, D279G, N285D and C292S.

SEQ ID NO:3—amino acid sequence of a human complement factor B analog, hfB3-292S-740N, comprising the following mutations as compared to SEQ ID NO:1: K258A, R259A, K260A, D279G, N285D, D740N and C292S.

SEQ ID NO:4—amino acid sequence of a human complement factor B analog, hfB3, which comprises the following mutations as compared to SEQ ID NO:1: K258A, R259A, K260A, D279G and N285D.

SEQ ID NO:5—nucleotide sequence of an hfB3 expression construct, the construction of which is described in Example 1.

SEQ ID NO:6-7—primers for site directed mutagenesis

SEQ ID NO:8—nucleotide sequence of an hfB3-292S expression construct, the construction of which is described in Example 2.

SEQ ID NO:9-14—partial amino acid sequences of complement factor B proteins from a human, a mouse, a rat, a pig, a monkey and a sheep, respectively.

SEQ ID NO:15-16—primers for site directed mutagenesis

SEQ ID NO:17—amino acid sequence of a human complement factor B protein analog, hfB4.

SEQ ID NO:18—nucleotide sequence of an hfB3-Fc expression construct, the construction of which is described in Example 12.

SEQ ID NO:19-20—primers for site directed mutagenesis.

SEQ ID NO:21—amino acid sequence of a human complement factor B protein analog, hfB3-Fc.

SEQ ID NO:22—amino acid sequence of a human complement factor B protein analog, hfB3-292S-Fc.

SEQ ID NO:23—amino acid sequence of a human complement factor B protein analog, hfB3-292S-740N-Fc.

SEQ ID NO:24—nucleotide sequence of an expression construct for expressing hfB3-292SN480.

SEQ ID NO:25—nucleotide sequence gene expression construct for hfB3-292S/Fc-mono.

SEQ ID NO:26—amino acid sequence of hfB3-292S/Fc-mono.

SEQ ID NO:27—amino acid sequence of an Fc domain.

DETAILED DESCRIPTION

The practice of the present invention will employ, unless otherwise indicated, conventional techniques of cell biology, molecular biology, cell culture, virology and the like which are in the skill of one in the art. These techniques are fully disclosed herein and/or in current literature, for example, Sambrook, Fritsch and Maniatis eds., "Molecular Cloning, A Laboratory Manual", 2nd Ed., Cold Spring Harbor Laboratory Press (1989); Celis J. E. "Cell Biology, A Laboratory Handbook" Academic Press, Inc. (1994) and Bahnson et al., J. of Virol. Methods, 54:131-143 (1995).

It is contemplated that any method, preparation or composition described herein can be implemented with respect to any other method, preparation or composition described herein. The use of the word "a" or "an" when used in conjunction with the term "comprising" in the claims and/or the specification may mean "one," but it is also consistent with the meaning of "one or more," "at least one," and "one or more than one." The use of the term/phrase "and/or" when used with a list means one or more of the listed items may be utilized, e.g., it is not limited to one or all of the elements.

Figure 6:
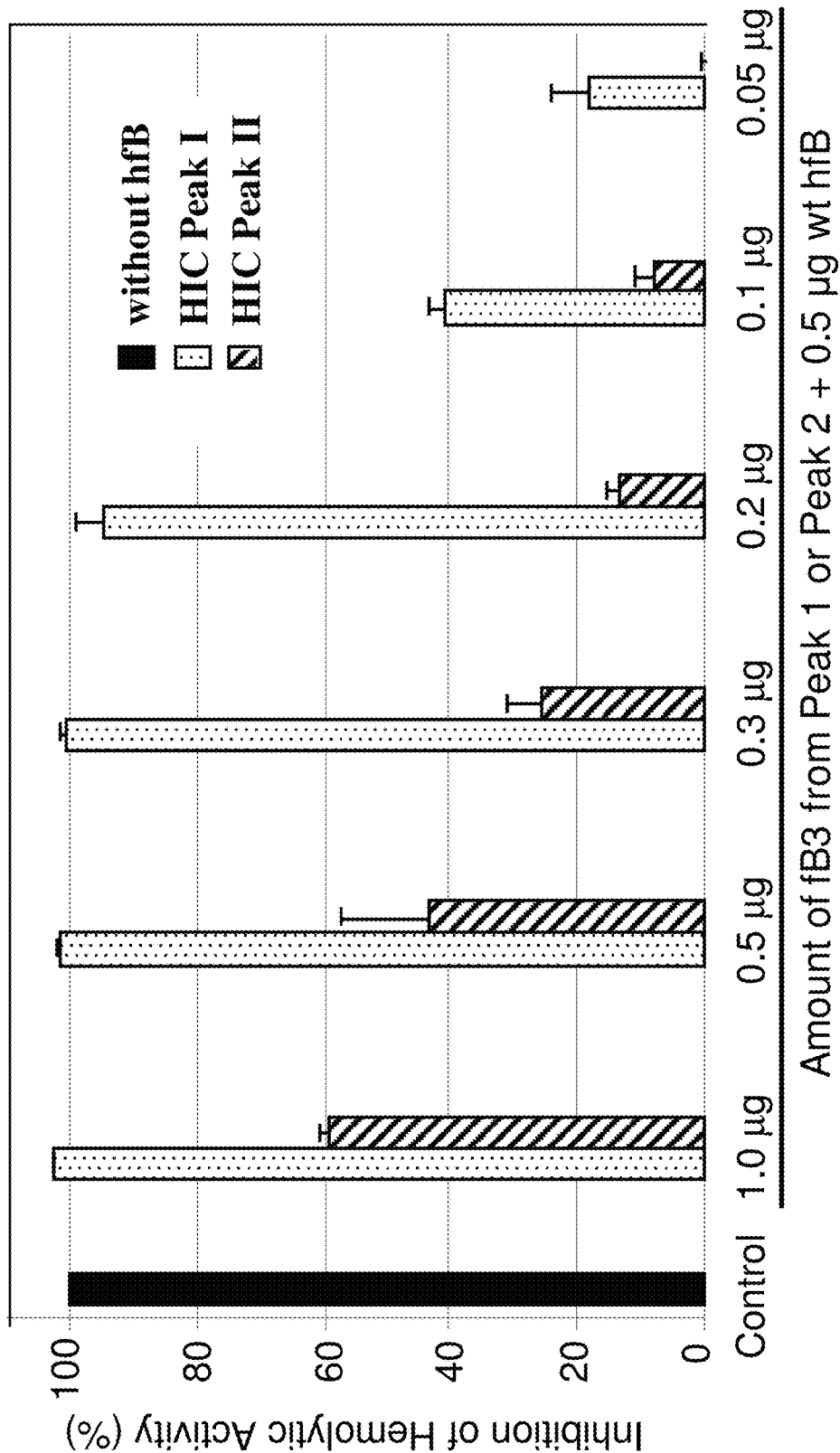

During production and purification of the complement factor B protein analog designated hfB3 (SEQ ID NO:4), two populations of the complement factor B protein analog were detected. One population had the desired activity for the complement factor B protein analog (Peak I) while the other population had substantially less of the desired activity (Peak II), e.g., see FIGS. 6, 7A and 7B. The results from characterization of the two populations suggested that the two populations differed in their disulfide bond patterns. When the free cysteine (position 292 of SEQ ID NO:4) was mutated to a serine, Peak II was undetectable. FIG. 6 shows that the Peak II fraction exhibits some ability to inhibit complement/hemolytic activity, but much less ability per μg of protein as compared to the Peak I fraction. It is possible that the complement/hemolytic inhibitory activity seen with Peak II is mostly or solely a result of Peak II being containing some hfB3 with a free cysteine at position 292, possibly as a result of Peak I and Peak II not being fully resolved from each other.

The cysteine corresponding to position 292 of SEQ ID NO:1 is highly conserved among complement factor B proteins of different mammalian species (e.g., see Table 1). Highly conserved sequences are typically important to the function of a protein. "The neutral theory of molecular evolution states that mutations in amino acids occur in a stochastically constant manner as long as the mutations have no effect on the function of the gene product [Kimura M: The neutral theory of molecular evolution. Sci Am 1979, 241(5):98-100, 102, 108 passim]. On the other hand, amino acids that are important for protein function and structure cannot mutate without a detrimental effect on protein activity. Therefore, these amino acids will change very slowly in a given protein family during evolution." (Liu et al. BMC Bioinformatics 2006, 7:37)

TABLE 1

Conserved Cysteine in Complement Factor B Protein

| | | |
|---|---|---|
| HUMAN* | IGASNFTGAKK<u>C</u>LVNLIEKVASY | (SEQ ID NO: 9) |
| MOUSE | IGSSNFTGAKR<u>C</u>LTNLIEKVASY | (SEQ ID NO: 10) |
| RAT | IGASNFTGAKR<u>C</u>LANLIEKVASY | (SEQ ID NO: 11) |
| PIG | IGARNFTGAKN<u>C</u>LKDFIEKVASY | (SEQ ID NO: 12) |
| MONKEY | IGAGNFTGAKK<u>C</u>LVNLIEKVASY | (SEQ ID NO: 13) |
| SHEEP | VGAHNFTGAKN<u>C</u>LRDFIEKVASY | (SEQ ID NO: 14) |

*<u>C</u> corresponds to position 292 for a human factor B (SEQ ID NO: 1)

Mutating the cysteine at amino acid 292 of the complement factor B protein analog to a serine, e.g., as shown in SEQ ID NO:2 (hfB3-292), greatly reduced, if not eliminated, the amount of the Peak II (substantially less active) population and the hfB3-292S complement factor B protein analog retained its activity, in this case the ability to inhibit or reduce complement activity. (E.g., see Example 10, below.)

Not wishing to be bound by theory, the less active population (Peak II fraction) of hfB3 protein could be the result of misfolding of hfB3 protein. It is possible that the generation of the majority of Peak II population was due to the combination of the free cysteine and the mutations introduced to hfB3 protein because when cells were engineered to express a wild-type human complement factor B protein (SEQ ID NO:1) in a manner similar to that used for hfB3 protein, only one population of the wild-type human factor B protein was detected (data not shown).

This mutation of a free cysteine allows for a higher yield of the active complement factor B analog since most, if not all, of the produced complement factor B protein analog is in an active form. Additionally, mutation of a free cysteine results in a more stable protein since all of the remaining unmutated cysteines are part of a disulfide bond and there is no free cysteine left that can participate in possibly undesirable and detrimental reactions. Additionally, mutating the free cysteine unexpectedly appears to have reduced or eliminated aggregation of the complement factor B protein analog, e.g., see Example 6 and FIG. 3.

The complement factor B protein analogs described in PCT Publication No. WO08/106644 or U.S. Patent Publication No. US20100120665 (both of which are incorporated by reference in their entirety) can have their free cysteine mutated and still retain their desired function, while benefiting from the aforementioned advantages of the mutation. Therefore, the present invention includes any of the complement factor B protein analogs described in PCT Publication No. WO08/106644 or U.S. Patent Publication No. US20100120665 with a mutation of a free cysteine.

The term "free cysteine" refers to a cysteine that is part of a protein or a peptide, wherein the free cysteine does not form a disulfide bond with another cysteine in the same protein or peptide. In some cases a "free cysteine" of a protein analog does not form a disulfide bond with another cysteine (in the same protein or peptide) when the protein analog has a desired activity, but may form a disulfide bond with another cysteine (in the same protein or peptide) in a less active or inactive form of the protein analog.

The term "complement-mediated" refers to a process or disease that involves complement. Typically, a "complement-mediated" disease or condition is one wherein complement activity is one of the underlying causes of the disease or condition and wherein inhibition or blocking of the complement activity lessens the extent of the disease or condition. Examples of numerous complement-mediated diseases or conditions are described herein.

The term "wildtype" (or wild-type), which is used interchangeably with "native", relates to a naturally occurring protein encoded by a mammalian genome, a naturally occurring nucleic acid, and so on. In some cases, there may be actually more than one protein corresponding to the wildtype version, e.g., due to allelic differences; different isoforms; and/or genetic variation among different individuals of a species.

The term "analog" refers to a structural derivative of a protein (parent protein). An analog does not necessarily retain all of the properties of the parent protein and in some cases has at least one altered property as compared to the corresponding native parent protein. In some embodiments, a parent protein is a native (naturally-occurring) protein. An analog or variant protein is produced by replacing, substituting, deleting, and/or adding amino acids with regard to the corresponding native amino acid sequence of the protein. The substitutions or insertions typically involve naturally occurring amino acids, but may also include synthetic or unconventional amino acids as well. In some embodiments, an analog or variant is produced by mutating a protein, e.g., mutating a nucleic acid encoding it. An analog will typically retain at least 70%, at least 75%, at least 80%, at least 85%, at least 90%, at least 95%, at least 96%, at least 97%, at least 98%, at least 99%, at least 99.5% of the corresponding native parent protein's amino acid sequence (e.g., have that percent amino acid sequence identity with respect to the naturally occurring parent protein as determined over the length of the entire parent protein or, in certain embodiments, over a specific domain or portion of the parent protein). Analogs also include fragments of full length analogs that comprise a portion of the amino acid sequence and either retain one or more biological activities of the parent protein or of a full length analog or inhibit one or more of these biological activities.

The term "corresponds" or "corresponding" when referring to an amino acid in a particular protein refers to the particular amino acid in that particular protein and also to an amino acid in a related or similar protein and may provide a similar function to the protein. For example, an amino acid in a human complement factor B may be found to correspond with an amino acid in a murine complement factor B or in a human allelic variant of factor B, usually determined by aligning the two amino acid sequences. For example, one skilled in the art can align two or more related sequences, such as SEQ ID NOs:9-14, to determine corresponding amino acids, e.g., using a BLAST program (e.g., see Table 1, above). Also, corresponding amino acids can be determined, e.g., by aligning motifs (e.g., a protease cleavage motif) within related or unrelated proteins. Such an alignment may also be used to derive consensus sequences of target protein or domains thereof.

As used herein, the term "gene" typically refers to a coding region for a protein. However, in some contexts herein it will be clear that the term "gene" is also referring to elements (e.g., regulatory elements) operatively linked to a coding region such as promoters, enhancers, splice sites (acceptors and/or donors), polyadenylation signals, introns, 5' untranslated regions, 3' untranslated regions, etc.

The term "pharmaceutically acceptable" means approved by a regulatory agency of the Federal or a state government or listed in the U.S. Pharmacopeia or other generally recognized pharmacopeia for use in humans.

A "therapeutic benefit" is not necessarily a cure for a particular disease or condition (including any disease or condition described herein), but rather, encompasses a result which most typically includes alleviation of the disease or condition, elimination of the disease or condition, reduction of one or more symptoms associated with the disease or condition, prevention or alleviation of a secondary disease or condition resulting from the occurrence of a primary disease or condition, diminishing the likelihood of developing a condition or disease, diminishing the severity of a disease or condition, changing the character of a disease or condition, shortening the course of a disease or condition, slowing or preventing the progression or worsening of a disease or condition, and/or prevention of the disease or condition.

Complement Factor B Analogs

The present invention includes complement factor B protein analogs and polypeptides comprising complement factor analogs and their uses. Some embodiments of the invention include a complement factor B protein analog wherein a free cysteine has been mutated. In some embodiments, this mutation of a free cysteine can comprise a deletion of the free cysteine or substitution of the free cysteine with another amino acid(s). A free cysteine can be substituted with essentially any amino acid, that still allows for the complement factor B protein analog to retain at least some of the desired characteristic(s), such as the ability to downregulate, diminish or ablate complement activity. A substitution may be with one or more amino acids. In some embodiments, a free cysteine is substituted with a serine. In some embodiments, a free cysteine is substituted with one or more amino acids selected from the group consisting of alanine, histidine, isoleucine, leucine, methionine, phenylalanine, serine, threonine, tyrosine and valine. In some embodiments, a free cysteine corresponds to amino acid 292 of SEQ ID NO:1.

In some embodiments, the invention provides complement factor B protein analogs that do not comprise a free cysteine. The invention also provides methods of making or producing a complement factor B protein analog comprising mutating a free cysteine.

Mutation of a free cysteine can be combined with other mutations of a complement factor B protein, e.g., other mutations as described herein.

The invention also provides complement factor B protein analogs wherein the cysteine corresponding amino acid 292 of SEQ ID NO:1 is mutated. This mutation can be a deletion, insertion or substitution, such as a serine substitution or other mutations as described herein.

Analogs can include various muteins of a sequence other than the naturally-occurring amino acid sequence. For example, single or multiple amino acid substitutions (e.g., conservative or non-conservative amino acid substitutions) may be made in the naturally-occurring sequence. A conservative amino acid substitution generally should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991). Conservative substitutions include, but are not limited to, those from the following groupings:

Acidic Residues Asp (D) and Glu (E); Basic Residues Lys (K), Arg (R), and His (H); Hydrophilic Uncharged Residues Ser (S), Thr (T), Asn (N), and Gln (Q); Aliphatic Uncharged Residues Gly (G), Ala (A), Val (V), Leu (L), and Ile (I); Non-polar Uncharged Residues Cys (C), Met (M), and Pro (P); Aromatic Residues Phe (F), Tyr (Y), and Trp (W); Alcohol group-containing residues S and T; Aliphatic residues I, L, V and M; Cycloalkenyl-associated residues F, H, W and Y; Hydrophobic residues A, C, F, G, H, I, L, M, R, T, V, W and Y; Negatively charged residues D and E; Polar residues C, D, E, H, K, N, Q, R, S and T; Positively charged residues H, K and R; Small residues A, C, D, G, N, P, S, T and V; Very small residues A, G and S; Residues involved in turn formation A, C, D, E, G, H, K, N, Q, R, S, P and T; and Flexible residues Q, T, K, S, G, P, D, E and R.

In some embodiments, a non-conservative substitution is used.

In some embodiments, mutations include, but are not limited to, substitutions of one or more amino acids, deletions of one or more amino acids or insertions of one or more amino acids. Mutations include, but are not limited to, those which: (1) reduce susceptibility of the complement factor B analog to proteolysis, (2) reduce susceptibility of the complement factor B analog to oxidation, (3) alter binding affinity of the complement factor B analog for forming protein complexes, (4) alter (e.g., increase or decrease) binding affinities of the complement factor B analog, (5) reduce immunogenicity of the complement factor B analog; (6) increase stability (e.g., thermostability) of the complement factor B analog; (7) reduce aggregation of the complement factor B protein analog; or any combinations of 1-7.

In some embodiments, a human complement factor B analog of the invention competes with binding of native complement factor B. For example native complement factor B can bind with complement factor C3b to form C3bB, e.g., see FIG. 1B. Factor B that is part of the C3bB complex can bind factor D. Therefore, in some embodiments, a complement factor B analog of the invention can compete with the binding of a native factor B for (i) binding to C3b, (ii) binding to factor D or (iii) both.

In some embodiments, a complement factor B protein analog of the invention, is an analog of SEQ ID NO:4 having cysteine amino acids that form disulfide bonds and a free cysteine amino acid that has been substituted by another amino acid, more than one amino acid or has been deleted with no substitution.

In some embodiments of the invention, a complement factor B protein analog has increased C3b binding affinity as compared to a corresponding native complement factor B protein and the complement factor B protein analog comprises (i) diminished protease activity as compared to a corresponding native complement factor B protein; (ii) diminished ability to be cleaved by factor D protein as compared to a corresponding native complement factor B protein; or (iii) diminished protease activity as compared to a corresponding native complement factor B protein and diminished ability to be cleaved by a factor D protein as compared to a corresponding native complement factor B protein.

In some embodiments, a complement factor B analog comprises a mutation in the C3b binding domain and the complement factor B protein analog exhibits increased binding affinity to C3b as compared to the binding affinity of a corresponding native complement factor B protein to C3b. In some embodiments, a mutation in the C3b binding domain comprises (i) a substitution or deletion of an aspartic acid corresponding to amino acid 279 of SEQ ID NO:1, a substitution or deletion of an asparagine corresponding to amino acid 285 of SEQ ID NO:1 or both; or (ii) an insertion of at least one amino acid next to said aspartic acid or said asparagine. In some embodiments, this aspartic acid, asparagine or both are substituted with one or more amino acids. In some embodiments, an aspartic acid corresponding to amino acid 279 of SEQ ID NO:1 is substituted with glycine, alanine or asparagine. In some embodiments, an asparagine corresponding to amino acid 285 of SEQ ID NO:1 is substituted with glycine, alanine, or aspartic acid. In some embodiments, an aspartic acid corresponding to amino acid 279 of SEQ ID NO:1 is substituted with glycine and an asparagine corresponding to amino acid 285 of SEQ ID NO:1 is substituted with aspartic acid.

In some embodiments, a complement factor B protein analog is a human complement factor B protein analog, based on a human complement factor protein.

The instant invention includes complement factor B protein analogs, e.g., that can be delivered as proteins and/or via gene transfer to attenuate the alternative pathway of complement activation. These analogs may overcome hurdles that impede the development of some complement inhibitors including, for example; 1) avoiding long term systemic immune suppression; 2) achieving efficacy in the face of otherwise prohibitively high levels of complement factors in the blood; 3) achieving sufficient levels and distribution of the therapeutic complement factor B protein analog in the proximity of the retina and Bruch's membrane for efficacy; 4) achieving activity of the therapeutic complement factor B protein analog within drusen; 5) achieving sufficient duration of therapeutic delivery to treat a chronic disease; 6) achieving efficacy without detrimentally interfering with the classical complement pathway activities in the back of the eye; and/or 7) avoiding or diminishing an immune reaction (e.g., a local immune reaction) to the therapeutic.

Attenuating the positive feedback loop in the alternative pathway is a means of down-regulating the entire alternative pathway. One suitable means for attenuating the alternative pathway feedback loop is to interfere with complement factor B (fB) protein function or levels. Some embodiments of the invention use a complement factor B analog for attenuating complement activity.

A complement factor B protein analog of the invention may comprise at least one mutation corresponding to a mutation of SEQ ID NO:1 selected from the group consisting of K258A, R259A, K260A, D279G, N285D and D740N. In some embodiments, it comprises mutations corresponding to K258A, R259A, K260A, D279G and N285D of SEQ ID NO:1. In some embodiments, a complement factor B protein analog comprises a mutation corresponding to D740N of SEQ ID NO:1.

For exemplary purposes, specific analogs of complement factor B protein are described herein. Factor B protein can be manipulated in a number of ways, e.g., to inhibit or reduce activation of the alternative pathway. In some embodiments, particular sites in factor B can be altered, for example, by site directed mutagenesis, so that the molecule no longer fully functions properly. In some embodiments, the enzyme portion or domain, (e.g., the protease domain, which is a serine protease) of the molecule can be altered so that the molecule no longer has enzymatic activity or has reduced enzymatic activity (e.g., reduced by at least 2 fold, 5 fold, 10 fold, 50 fold or 100 fold). In some embodiments, a complement factor B protein analog comprises a mutation in the active site of the serine protease domain, wherein the mutation decreases or ablates the complement factor B protein analog's ability to cleave complement factor C3 as compared to a corresponding native complement factor B protein.

In some embodiments, this can be achieved by altering the residue corresponding to amino acid 740 of SEQ ID NO:1. In some embodiments, this mutation comprises a deletion or a substitution of an aspartic acid corresponding to amino acid 740 of SEQ ID NO: 1. In some embodiments, an aspartic acid (D), corresponding to amino acid 740 of SEQ ID NO:1, is substituted with another amino acid such as asparagine (N), alanine (A), glutamic acid (E), serine (S), tyrosine (Y), or glycine (G). The numbering of particular factor B amino acids herein relates to the entire polypeptide including the signal peptide and is reflected in SEQ ID NO: 1. Hourcade et al. (JBC (1998) 273(40):25996-6000) notes that amino acids 739-746 of SEQ ID NO:1 (referred to in Hourcade et al. as amino acids 714-721 because the Hourcade et al. numbering does not include the 25 amino acid signal sequence/peptide) play a role in the serine protease function of factor B protein. Additionally, N693, T694 and D740 may constitute or be part of the substrate binding site and H526, D576 and S699 may constitute or be part of the catalytic center, e.g., see Xu et al., J Biol Chem. 2000 275(1):378-85. In some embodiments, a factor B protein analog comprises a mutation of at least one of the amino acids selected from amino acids 739-746 of SEQ ID NO:1. In some embodiments, a complement factor B protein analog comprises a substitution of the amino acid corresponding to amino acid 739 of SEQ ID NO:1 with an alanine. In some embodiments, a complement factor B protein analog comprises a substitution of the amino acid corresponding to amino acid 740 of SEQ ID NO:1 with an amino acid selected from the group consisting of asparagine, glutamic acid, alanine, serine and tyrosine. In some embodiments, a complement factor B protein analog comprises a substitution of the amino acid corresponding to amino acid 741 of SEQ ID NO:1 with an amino acid selected from the group consisting of tryptophan and alanine. In some embodiments, a complement factor B protein analog comprises a substitution of the amino acid corresponding to amino acid 742 of SEQ ID NO:1 with glutamine. In some embodiments, a complement factor B protein analog comprises a substitution of the amino acid corresponding to amino acid 743 of SEQ ID NO:1 with phenylalanine. In some embodiments, a complement factor B protein analog comprises a substitution of the amino acid corresponding to amino acid 745 of SEQ ID NO:1 with phenylalanine. In some embodiments, a complement factor B protein analog comprises a substitution of the amino acid corresponding to amino acid 746 of SEQ ID NO:1 with tryptophan or alanine. In some embodiments, a factor B protein analog comprises a mutation of one or two of the amino acids 693 and 694 of SEQ ID NO:1, e.g., a substitution or deletion. In some embodiments, a factor B protein analog comprises a mutation of one or two of the amino acids 526, 576 and 699 of SEQ ID NO:1, e.g., a substitution or deletion.

Other sites in factor B that can be altered include: 1) the binding site for properdin (the properdin binding domain) such that binding occurs with lower affinity (for example, such as 2 fold, 5 fold, 10 fold, 50 fold or 100 fold reduced affinity as compared to the wild type factor B protein) or with greater affinity (such as at least 2 fold, 5 fold, 10 fold, 50 fold or 100 fold increased affinity as compared to the wild type factor B); 2) the binding site for C3b protein (the C3b binding domain) such that binding occurs with lower affinity (such as at least 2 fold, 5 fold, 10 fold, 50 fold or 100 fold reduced affinity as compared to the wild type factor B protein) or with greater affinity (such as at least 2 fold, 5 fold, 10 fold, 50 fold or 100 fold increased affinity as compared to wild type factor B protein, for example, this may be achieved by substituting the amino acid corresponding to position 279 and/or position 285 of SEQ ID NO:1 with other amino acids, for example, wherein the amino acid at the position corresponding to position 279 is substituted with asparagine (N), alanine (A) or glycine (G) and/or the amino acid at the position corresponding to position 285 is substituted with aspartic acid (D) or alanine (A)); 3) the site acted on by factor D such that factor D has reduced ability to cleave or no longer cleaves factor B to form Bb (for example, at the factor D cleavage site, at least one of the amino acids at the positions corresponding to position 258, 259 or 260 of SEQ ID NO:1, for example, can be altered to alanine (A) or; a combination of any of 1, 2, and/or 3 above).

In some embodiments, a complement factor B protein analog comprises an alteration in the complement factor D cleavage site wherein the alteration decreases or ablates cleavage of the complement factor B protein analog by factor D protein. In some embodiments, an alteration in the factor D cleavage site comprises (i) a substitution or deletion of an arginine corresponding to amino acid 259 of SEQ ID NO:1, a substitution or deletion of one or both lysines corresponding to amino acid 258 or 260 of SEQ ID NO:1 or a substitution or deletion of the arginine and both lysines; or (ii) an insertion next to the arginine, next to the one or both lysines, or next to the arginine and one or both of the lysines. In some embodiments, a complement factor B protein analog has amino acids corresponding to amino acids 258-260 of SEQ ID NO:1 each replaced with alanine.

The invention includes (i) complement factor B protein analogs that bind to both factors C3b and D; (ii) complement factor B protein analogs with increased binding (as compared to their native form) to both factors C3b and D; (iii) complement factor B protein analogs with increased binding (as compared to their native form) to factor D protein; and (iv) complement factor B protein analogs with increased binding (as compared to their native form) to C3bB complex. The invention also includes methods of inhibiting a complement pathway using the complement factor B protein analogs of the invention, such as i-iv, above.

In some embodiments, increased binding is increased by about 1.5 to about 10,000, about 10 to about 10,000, about 100 to about 10,000, about 1,000 to about 10,000, about 1.5 to about 1,000, about 1.5 to about 100, about 1.5 to about 10, about 2 to about 5, about 2 to about 10, about 5 to about 10, about 5 to about 20, about 10 to about 20, about 10 to about 30, about 20 to about 30, about 30 to about 50, about 50 to about 100, about 100 to about 500, about 500 to about 1,000, about 1,000 to about 5,000, or about 5,000 to about 10,000 fold. In some embodiments, increased binding is increased by greater than 1.5, 2, 3, 4, 5, 10, 50, 100, 500, 1000, 5000 or 10,000 fold. In some embodiments, increased binding can be measured by immunoprecipitation or using a Biacore (GE Healthcare, Piscataway, N.J.), e.g., as compared to the wild type protein. As an example for (i) above, binding could be measured by immunoprecipitation of the protein with a binding molecule for C3b protein and then detecting factor D protein in the immunoprecipitate, e.g., using an immunoassay such as an ELISA or Western, for example, with increased binding demonstrated as a band of increased intensity in a Western.

Some factor B protein analogs of the invention may have increased binding to C3b protein and/or factor D protein by a factor of 2 fold, 4 fold, 5 fold, 10 fold, 20 fold, 50 fold, 100 fold, 500 fold, 1000 fold as compared to binding of wild type factor B to C3b and/or factor D. In some embodiments, increased binding can be measured by immunoprecipitation or using a Biacore (GE Healthcare, Piscataway, N.J.).

Some modified factor B protein analogs of the invention comprise one or more of the amino acid alterations discussed herein and additionally have one or more additional amino acid substitutions, insertions or alterations (e.g., at least or no more than 1, 2, 5, 8, 10, 15 20, 50, 100, or 200 alterations), which analogs retain the increased binding to C3b and/or factor D or other biological activity of the factor B protein analogs discussed herein, which mediates inhibition of the complement pathway. Such analogs may have at least 99.9%, 99%, 98%, 95%, 90%, 85%, 80%, 75% or 70% amino acid sequence identity with a wild type factor B protein, for example, the amino acid sequence of SEQ ID NO:1 and retain the increased binding to C3b and/or factor D.

In the context of gene therapy and expression of complement factor B protein analogs, the alterations/mutations will be reflected at the level of the encoding nucleic acid. Thus, modifications also can be made to the nucleic acid to enhance expression. For example, certain codons may be preferred by a particular host cell. Thus, recoding can be performed where certain codons are preferred in, for example, a particular mammalian expression system or cell.

Some embodiments of the invention are directed to polynucleotides and host cells (or host multicellular organisms) useful in the production of a complement factor B protein analog and directed to the analogs, e.g., hfB3-292S (SEQ ID NO:2), hfB3-292S-740N (SEQ ID NO:3), hfB3-292S-Fc (SEQ ID NO:22), hfB3-292S-740N-Fc (SEQ ID NO:23) or hfB3-292S/Fc-mono (SEQ ID NO:26). Methods of isolating and testing complement-mediated activity of these complement factor B protein analogs are also provided. Some aspects of the invention are directed to pharmaceutical compositions/preparations wherein a complement factor B protein analog is an active ingredients in a therapeutic and/or a prophylactic contexts. Some embodiments of the invention are also directed to methods of treating complement-mediated disorders using a therapeutically effective amount of a complement factor B protein analog.

In some embodiments of the invention, a complement factor B analog may comprise glycosylation patterns which are distinct from glycosylation patterns on a naturally-occurring complement factor B, or may lack glycosylation altogether. Carbohydrates may be added to and/or removed from factor B analogs comprising glycosylation site sequences for N- and/or O-linked glycosylation in vitro, such as with a canine pancreatic microsome system (e.g., see Mueckler and Lodish (1986) Cell 44:629 and Walter, P. (1983) Meth. Enzymol. 96:84) or the like. A complement factor B analog of the invention may be produced comprising adding or deleting/mutating an amino acid sequence corresponding to a glycosylation site, e.g., changing the glycosylation pattern/status of a protein can change functional characteristics of a protein. For example, hfB2, hfB3 (SEQ ID NO:4), hfB3-292S (SEQ ID NO:2), hfB3-292S-740N (SEQ ID NO:3), hfB3-292S-Fc (SEQ ID NO:22), hfB3-292S-740N-Fc (SEQ ID NO:23) and hfB3-292S/Fc-mono (SEQ ID NO:26) comprise an N285D substitution, as compared to a wildtype factor B (SEQ ID NO:1), which results in the removal of an N-glycosylation site. (Both the hfB2 and hfB3 complement factor B protein analogs are described in detail in U.S. Patent Publication No. US20100120665.) The loss of the N-glycosylation site alters the characteristics of the protein. The same effect may be achieved by producing the protein in a cell that has an altered glycosylation pattern or that does not glycosylate this N285. For example, a factor B protein or analog may be produced in an *E. coli* cell that does not glycosylate the N285. In some embodiments, a complement factor B protein analog is produced in a cell (e.g., an *E. coli*) that does not glycosylate an amino acid corresponding to a wildtype factor B protein that is typically glycosylated, e.g., corresponding to amino acid N285 of SEQ ID NO:1.

As demonstrated in PCT Publication No. WO08/106644 and U.S. Patent Publication No. US20100120665, in some cases a native factor B protein from one species may have activity in a complement reaction/pathway from another species. Therefore, the present invention also includes complement factor B protein analogs from one species for inhibiting complement activity in another species.

In some embodiments, a complement factor B protein analog of the invention is PEGylated, e.g., see Roberts et al., Advanced Drug Delivery Reviews 54(4):459-476 (2002); Veronese, Biomaterials 22(5):405-417 (2001); Fee and Alstine, Chemical Engineering Science 61(3):924-939 (2006); Kodera et al., Progress in Polymer Science 23(7): 1233-1271 (1998); Morar, Biopharm International 19(4):34 (2006); and Veronese and Pasut, Drug Discovery Today 10(21):1451-1458 (2005). Polyethylene glycol (PEG) can be attached to a complement factor B protein analog of the invention. In some embodiments, PEG is attached with or without a multifunctional linker either through site-specific conjugation of the PEG (e.g., to the N-terminus or to the C terminus of a complement factor B analog) or via epsilon amino groups present on lysine residues. In some embodiments, linear or branched polymer derivatization that results in minimal loss of biological activity can be used. The degree of conjugation can be closely monitored by SDS-PAGE and mass spectrometry to ensure proper conjugation of PEG molecules to a complement factor B analog. In some embodiments, unreacted PEG can be separated from PEG conjugates by size-exclusion and/or by ion exchange chromatography.

In certain embodiments, the carboxy-terminus, the amino-terminus or both of a complement factor B analog, are chemically modified Amino-terminal modifications such as acylation (e.g., acetylation) or alkylation (e.g., methylation) and carboxy-terminal modifications such as amidation, as well as other terminal modifications, including cyclization, may be incorporated into various embodiments of the invention. Certain amino-terminal and/or carboxy-terminal modifications and/or peptide extensions (such as fused to a heterologous polypeptide, such as albumin, immunoglobulin or portion thereof, such as an immunoglobulin Fc domain) to the core sequence can provide advantageous physical, chemical, biochemical, and pharmacological properties, such as enhanced stability, increased potency and/or efficacy, resistance to serum proteases, desirable pharmacokinetic properties, and others.

In some embodiments, a complement factor B protein analog of the invention comprises an immunoglobulin Fc domain, for example, a human immunoglobulin Fc domain. In some embodiments, an Fc domain is C-terminal to the corresponding complement factor B analog amino acid sequence. In some embodiments, an Fc domain comprises or consists of amino acids 766-990 of SEQ ID NO:21 or amino acids 766-1003 or 786-1003 of SEQ ID NO:26. In some embodiments, an Fc domain is amino acids 1-239 or 2-239 of SEQ ID NO:27. In some embodiments, an Fc domain is a human Fc domain. In some embodiments, an Fc domain is from an immunoglobin, e.g., an IgG such as IgG4. In some embodiments, an Fc domain is capable of forming a dimer with another Fc domain. In some embodiments, a complement factor B analog of the invention is capable of forming dimers (e.g., homologous dimers), such as, but not limited to, through interactions of Fc domains. In some embodiments, a complement factor B analog does not form dimers or the majority of a complement factor B analog population/preparation is in the form of monomers. In some embodiments, a complement factor B analog comprising an Fc domain does not form dimers or the majority of this complement factor B analog population/preparation is in the form of monomers. In some embodiments, a complement factor B analog comprises an Fc domain that has one or mutations of a cysteine(s) in the Fc domain sequence, e.g., a cysteine involved in dimerization of the Fc domain. In some embodiments, a Fc domain comprises a mutation of one or more cysteines corresponding to amino acids 17 and/or 20 of SEQ ID NO:27. In some embodiments, a complement factor B analog comprises an Fc domain that has one or mutations of a free cysteine(s) in the Fc domain sequence. In some embodiments, a cysteine(s) is substituted with an amino acid selected from the group consisting of histidine, isoleucine, leucine, methionine, phenylalanine, serine, threonine, tyrosine, and valine. In some embodiments, a cysteine is deleted. In some embodiments, an amino acid sequence linker is used between amino acid sequences for a complement factor B analog and an Fc region. In some embodiments, this linker is one amino acid, e.g., arginine.

In some embodiments, a polypeptide comprises both a truncated complement factor B analog and an Fc region such as comprising amino acids corresponding to amino acids 26-480 of SEQ ID NO:2 and an Fc region.

The invention further provides analogs which are fragments of a complement factor B protein or analog that contain at least a 20, 30, 50, 70, 100, 150, 200, 300, 400, 480, 500, 600 or 700 amino acid portion of the complement factor B protein or analog and/or comprises 1, 2 or 3 domains of the protein and have or retain one or more biological activities of the wild type complement factor B protein or analog and/or acts as an inhibitor of an aspect of the complement system (either the classical pathway, alternative pathway or both). These fragments can be further modified by linking or fusing with another protein or fragment such as an Fc to increase the stability and/or half-life of the analog. In some embodiments, an analog is fragment of a complement factor B protein or analog and the fragment has at least 99.5%, 99%, 98%, 95%, 90%, 85% or 62% identity with the corresponding amino acid sequence of a wild-type complement factor B.

The invention provides proteins comprising a fragment of a complement factor B protein or analog, wherein the fragment has an N-terminal and/or C-terminal truncation. In some embodiments, a complement factor B analog comprises a C-terminal truncation wherein the analog is truncated at or after (C-terminal to) an amino acid corresponding to amino acid 407, 427, 457, 477, 480, 484, 487, 507 or 527 of SEQ ID NOs:1, 2 or 4. In some embodiments, a complement factor B analog comprises a C-terminal truncation wherein the analog is truncated at an amino acid between amino acids corresponding to amino acids 407-487, 470-495 or 477-487 of SEQ ID NOs:1, 2 or 4. In some embodiments, a complement factor B analog of the invention does not comprise amino acids corresponding to amino acids 408-764, 428-764, 458-764, 478-764, 481-764, 485-764, 488-764, 507-764, 527-764 of SEQ ID NOs:1, 2 or 4. In some embodiments, truncation or fragmentation of a factor B protein or analog can create a free cysteine. For example, a truncation can result in the deletion of one cysteine of a cysteine pair that forms a disulfide bond in a native complement factor B protein, thus creating a polypeptide that contains a cysteine, but does not contain its native cysteine "partner". In some of these embodiments, the remaining cysteine of the pair may be mutated, e.g., substituted with another amino acid, such as an alanine, histidine, isoleucine, leucine, methionine, phenylalanine, serine, threonine, tyrosine and valine or the cysteine may be deleted, e.g., to eliminate possible undesired disulfide bonding.

Analogs of the invention can be prepared by various techniques, including but not limited to, chemical synthesis or by expression of the recombinant analog.

Nucleotide sequences for genes and coding regions encoding human factor B, as well as the amino acid sequences are known in the art. For example, a gene encoding human factor B is found in NCBI Database Accession No. NG_000013. A coding sequence for a human factor B is found in NCBI Database Accession No. NM_001710 and an amino acid sequence for a human complement factor B preproprotein is found in NCBI Database Accession No. NP_001701 or P00751. Sequences from other animal species are also known in the art. By way of comparison, in the mouse factor B protein sequence (e.g., see NCBI Database Accession No. P04186), the third SCR domain is located at positions 160-217 of this 761 amino acid preprotein, and the mature murine factor B protein spans positions 23-761. The first 22 amino acids of mouse factor B protein comprises a signal sequence.

Typically, a human factor B preprotein is a 764 amino acid protein (e.g., see SEQ ID NO:1) with a signal peptide spanning amino acid positions 1-25. The mature chain of factor B corresponds to positions 26-764 (e.g., see SEQ ID NO:1). The three SCR regions of human factor B are SCR1, also known as Sushi 1, spanning from about position 35 to about position 100, SCR2, also known as Sushi 2, spanning from about position 101 to about position 160 and SCR3, also known as Sushi 3, spanning from about position 163 to about position 220.

PCT Publication No. WO08/106644 and U.S. Patent Publication No. US20100120665 describe, inter alia, three specific dominant negative human factor B protein analogs designated as hfB1, hfB2 and hfB3. The first of these three analogs, termed fB1, contains a mutated amino acid in the factor B (fB) protease site. This fB moiety binds C3b with normal affinity and kinetics, but when acted upon by factor D (fD) and stabilized by properdin, does not function as a protease and does not form a C3 convertase. fB1 contains a substitution with N at an amino acid corresponding to amino acid 740 of SEQ ID NO:1 (e.g., D740N). The second of these complement factor B analogs, termed fB2, alters the same amino acid as fB1, but in addition, alters two additional amino acids in the C3b binding domain (substitutions at amino acids corresponding to amino acids 279 and 285 of SEQ ID NO:1) which increase the binding affinity of fB2 to C3b, e.g., D279G, N285D and D740N changes. The N285D substitution removes a putative N-glycosylation site. The third of these complement factor B protein analogs, termed hfB3, combines the mutations that increase C3b binding from fB2 with a mutation that knocks out the site for cleavage by factor D, particularly with substitutions at amino acids corresponding to residues 258, 259 and 260 of SEQ ID NO:1 as well as substitutions at amino acids corresponding to residues 279 and 285, e.g., K258A, R259A, K260A, D279G and N285D changes. Cleavage of wild type fB by factor D activates the fB protease. Thus, hfB3, with its five amino acid changes, efficiently binds C3b but has minimal protease activity.

hfB1, hfB2 and hfB3 are examples of human factor B analogs which can be further modified to complement factor B analogs of the present invention by mutating a free cysteine corresponding to amino acid 292 of SEQ ID NO:1, e.g., by substituting the cysteine with a serine, but the invention is not limited to these specific analogs. Some embodiments of the invention include any complement factor B analog that modulates a complement pathway and does not comprise a free cysteine. In some embodiments, a complement factor B analog comprises, in addition to a mutated free cysteine, one or more mutations of amino acids corresponding to one or more of the following amino acids in SEQ ID NO:1: amino acid 258, 259, 260, 279, 285, 739, 740, 741, 742, 743, 744, 745 and 746. These one or more mutations can be a substitution or deletion of the amino acid or an addition of at least one amino acid next to or within 1, 2, 3, 4, 5, 6, 7, 8, 9 or 10 amino acids of the corresponding amino acids. In some embodiments, this addition disrupts, changes, enhances or inhibits the function of the listed amino acid, e.g., disrupts its role (i) in cleavage of another protein (e.g., 740), (ii) as a site of cleavage by another protein (e.g., amino acids corresponding to residues 258, 259 and/or 260 of SEQ ID NO:1), or (iii) its role in binding another protein (e.g., amino acids corresponding to residues 279 or 285 of SEQ ID NO:1).

Some embodiments of the invention comprise a substitution of an amino acid corresponding to one or more of amino acids corresponding to 258, 259 and/or 260 of SEQ ID NO:1, e.g., with an amino acid selected from the group consisting of alanine, glycine, valine, leucine and isoleucine. Some embodiments of the invention comprise a deletion of an amino acid corresponding to one, two or three of amino acids corresponding to amino acids 258, 259 and/or 260 of SEQ ID NO:1. Some embodiments of the invention comprise at least one addition of 1, 2, 3, 4, 5, 6, 7, 8, 9, 10 or more amino acids immediately next to an amino acid corresponding to amino acids 258, 259 and/or 260 of SEQ ID NO:1.

Some embodiments of the invention comprise a substitution of an amino acid corresponding to amino acid 739 of SEQ ID NO: 1. Some embodiments of the invention comprise a substitution of an amino acid corresponding to amino acid 739 of SEQ ID NO:1, e.g., with an amino acid selected from the group consisting of alanine, glycine, valine, leucine and isoleucine. Some embodiments of the invention comprise a deletion of an amino acid corresponding to the 739 amino acid of SEQ ID NO:1.

Some embodiments of the invention comprise a substitution of an amino acid corresponding to amino acid 740 of SEQ ID NO:1, e.g., with an amino acid selected from the group consisting of glutamic acid, asparagine, alanine, serine, glycine and tyrosine. Some embodiments of the invention comprise a substitution of an amino acid corresponding to amino acid 740 of SEQ ID NO:1 with an amino acid selected from the group consisting of valine, leucine, isoleucine, threonine, cysteine, methionine, glutamine, phenylalanine, tyrosine, tryptophan, glutamic acid, asparagine, alanine, serine, glycine and tyrosine. Some embodiments of the invention comprise a deletion of an amino acid corresponding to the 740 amino acid of SEQ ID NO:1.

Some embodiments of the invention comprise a substitution of an amino acid corresponding to amino acid 741 of SEQ ID NO:1, e.g., with an amino acid selected from the group consisting of tryptophan and alanine. Some embodiments of the invention comprise a substitution of an amino acid corresponding to amino acid 741 of SEQ ID NO:1 with an amino acid selected from the group consisting of alanine, glycine, valine, leucine and isoleucine. Some embodiments of the invention comprise a substitution of an amino acid corresponding to amino acid 741 of SEQ ID NO:1 with an amino acid selected from the group consisting of tryptophan, tyrosine and phenylalanine. Some embodiments of the invention comprise a deletion of an amino acid corresponding to the 741 amino acid of SEQ ID NO:1.

Some embodiments of the invention comprise a substitution of an amino acid corresponding to amino acid 742 of SEQ ID NO:1, e.g., with a glutamine Some embodiments of the invention comprise a substitution of an amino acid corresponding to amino acid 742 of SEQ ID NO:1 with an amino acid selected from the group consisting of glutamine, glutamic acid, asparagine, and aspartic acid. Some embodiments of the invention comprise a deletion of an amino acid corresponding to amino acid 742 of SEQ ID NO:1.

Some embodiments of the invention comprise a substitution of an amino acid corresponding to amino acid 743 and/or 745 of SEQ ID NO:1, e.g., with a phenylalanine. Some embodiments of the invention comprise a substitution of an amino acid corresponding to amino acid 743 and/or 745 of SEQ ID NO:1 with an amino acid selected from the group consisting of phenylalanine, tyrosine and tryptophan. Some embodiments of the invention comprise a deletion of one or more of amino acids corresponding to amino acids 743, 744 and/or 745 of SEQ ID NO:1.

Some embodiments of the invention comprise a substitution of an amino acid corresponding to amino acid 746 of SEQ ID NO:1, e.g., with an amino acid selected from the group consisting of tryptophan and alanine. Some embodiments of the invention comprise a substitution of an amino acid corresponding to amino acid 746 of SEQ ID NO:1 with an amino acid selected from the group consisting of alanine, glycine, valine, leucine and isoleucine. Some embodiments of the invention comprise a substitution of an amino acid corresponding to amino acid 746 of SEQ ID NO:1 with an amino acid selected from the group consisting of tryptophan, tyrosine and phenylalanine. Some embodiments of the invention comprise a deletion of an amino acid corresponding to amino acid 746 of SEQ ID NO:1.

Some embodiments of the invention comprise the insertion or substitution of 1, 2, 3, 4, 5, 6, 7, 8, 9, 10 or more amino acids immediately next to or in place of any one or more of the amino acids corresponding to amino acids 739, 740, 741, 742, 743, 744, 745 and/or 746 of SEQ ID NO:1.

Some embodiments of the invention comprise a substitution of an amino acid corresponding to amino acid 279 of SEQ ID NO:1, e.g., with an amino acid selected from the group consisting of glycine, alanine and asparagine. Some embodiments of the invention comprise a substitution of an amino acid corresponding to amino acid 279 of SEQ ID NO:1 with an amino acid selected from the group consisting of glycine, alanine, valine, leucine and isoleucine. Some embodiments of the invention comprise a substitution of an amino acid corresponding to amino acid 279 of SEQ ID NO:1 with an amino acid selected from the group consisting of asparagine, glutamic acid and glutamine Some embodiments of the invention comprise a deletion of an amino acid corresponding to amino acid 279 of SEQ ID NO: 1. Some embodiments of the invention comprise the insertion or substitution of 1, 2, 3, 4, 5, 6, 7, 8, 9, 10 or more amino acids immediately next to or in place of an amino acid corresponding to amino acid 279 of SEQ ID NO:1.

Some embodiments of the invention comprise a substitution of an amino acid corresponding to amino acid 285 of SEQ ID NO:1, e.g., with an amino acid selected from the group consisting of alanine and aspartic acid. Some embodiments of the invention comprise a substitution of an amino acid corresponding to amino acid 285 of SEQ ID NO:1 with an amino acid selected from the group consisting of glycine, alanine, valine, leucine and isoleucine. Some embodiments of the invention comprise a substitution of an amino acid corresponding to amino acid 285 of SEQ ID NO:1 with an amino acid selected from the group consisting of aspartic acid, glutamic acid and glutamine Some embodiments of the invention comprise a deletion of the an amino acid corresponding to amino acid 285 of SEQ ID NO:1. Some embodiments of the invention comprise the insertion or substitution of 1, 2, 3, 4, 5, 6, 7, 8, 9, 10 or more amino acids immediately next to or in place of an amino acid corresponding to amino acid 285 of SEQ ID NO:1.

Some embodiments of the invention comprise a substitution of the one or more of the amino acids corresponding to amino acids 279, 282, 283, 284 and 285 of SEQ ID NO:1. In some embodiments, these amino acids are replaced with glycine, isoleucine, proline, histidine and aspartic acid, respectively.

Some embodiments of the invention comprise mutations of the amino acids corresponding to 258, 259, 260, 279 and 285 of SEQ ID NO:1 as described herein.

In some specific embodiments, the invention provides a factor B protein analog, that comprises the amino acid sequence of SEQ ID NO:2, 3, 21, 22, or 23 (optionally without any signal sequence, e.g., amino acids 1-25 contained therein). These factor B protein analogs can be used in methods of the invention.

The invention includes complement factor B protein analogs that comprise a combination of the mutations (substitutions, deletions and additions) discussed herein. In some embodiments, these complement factor B analogs retain one or more of the attributes of the hfB1, hfB2, hfB3, hfB3-292S or hfB3-292S-740N analogs or any other complement factor B analog discussed herein. The invention further provides analogs that are fragments (for example comprising one or more domains of a complement factor B protein having one or more of the amino acid mutations set forth herein) of these analogs that have one or more of the attributes of the analogs discussed above, e.g., hfB3-292SN480. In addition, the analogs may comprise additional amino acid substitutions, deletions or insertions (for example, conservative amino acid substitutions, truncations of the N-terminus or C-terminus, etc.) such that the analog has at least 99.5%, 99%, 98%, 95%, 90%, 85%, 80%, 75% or 75% identity with the corresponding wild-type complement factor B or, in the case of an analog comprising a fragment of complement factor B, the analog has at least 99.5%, 99%, 98%, 95%, 90%, 85%, 80%, 75% or 70% identity between the corresponding parts of the analog and wild-type complement factor B.

The hfB3-292S and hfB3-292SN480 proteins contain the following key features from N-terminus to C-terminus: 1) factor B protein native signal sequence for efficient secretion out of mammalian expression cells such as human 293 cells, CHO cells, BHK cells; 2) a mutated C3b-dependent factor D protein cleavage site (changing amino acids from K258R259K260 to A258A259A260); 3) a mutated C3b protein binding site (changing amino acid from D279 to G279; and amino acid from N285 to D285) to enable its tight binding with and trapping of C3b protein; and 4) a mutated free cysteine (changing amino acid C292 to S292) to increase the amount of "active" or correctly folded protein.

In some embodiments of the invention, a human complement factor B protein analog is at least 90%, at least 95%, at least 98% or at least 99% identical to (i) SEQ ID NOs:1, 2, 3, 22 or 23; (ii) amino acids 26-764 of SEQ ID NOs:1, 2 or 3; (iii) amino acids 1-990 or 26-990 of either of SEQ ID NOs:22 or 23; amino acids 26-480 of SEQ ID NO:2; and (iv) amino acids 1-1003 or 26-1003 of SEQ ID NO:26. In some embodiments, a human complement factor B protein analog of the invention comprises (i) SEQ ID NOs:2, 3, 22, 23 or 26; (ii) amino acids 1-480 of SEQ ID NO:2; (iii) amino acids 26-480 of SEQ ID NO:2; (iv) amino acids 26-764 of SEQ ID NOs:2 or 3; (v) amino acids 26-990 of SEQ ID NOs:22 or 23; or (vi) amino acids 26-1003 of SEQ ID NO:26. In some embodiments, a complement factor B protein analog consists essentially of (i) amino acids 26-764 of SEQ ID NO:2 or 3; (ii) amino acids 26-480 of SEQ ID NO:2 or 3; (iii) amino acids 26-990 of SEQ ID NOs:22 or 23; or (iv) amino acids 26-1003 of SEQ ID NO:26.

Figure 1A:
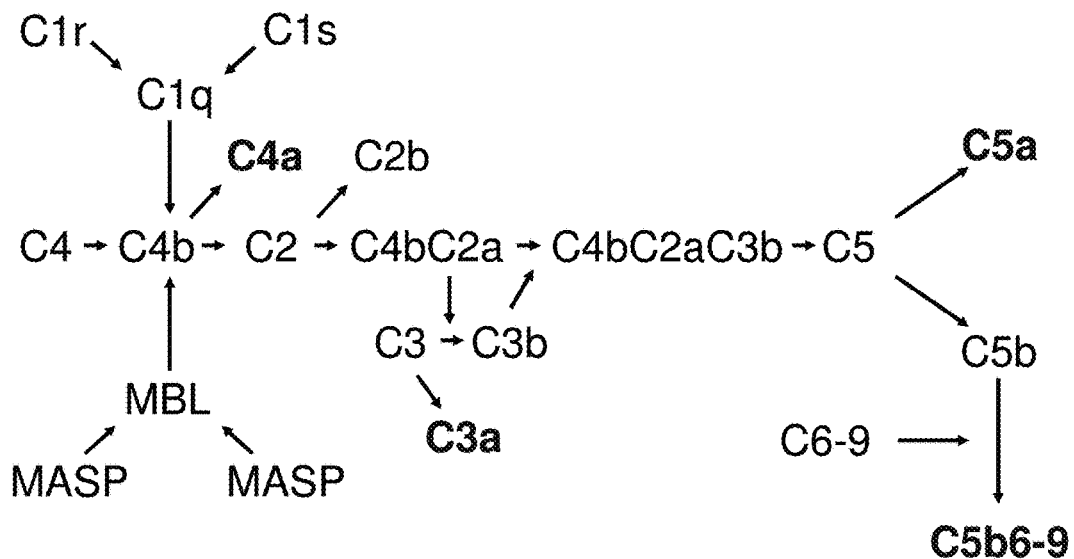
Figure 1B:
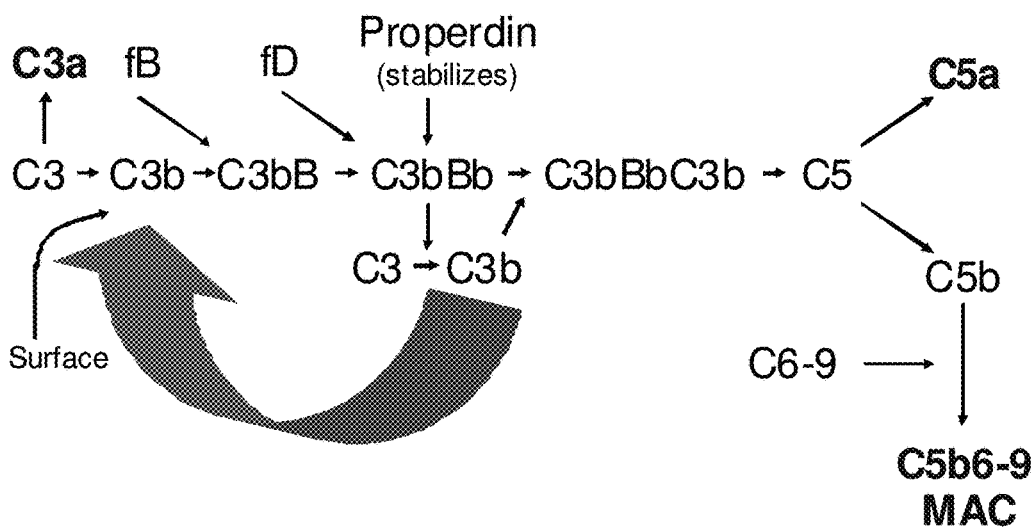

FIG. 1 depicts the classical and lectin complement pathways (FIG. 1a) and the alternative complement pathway (FIG. 1b). Both pathways utilize C3b. The C3bBb complex is a C3 convertase which converts C3 to C3b. Spontaneous dissociation ("decay") of the C3bBb within minutes leads to its inactivation, whereas properdin stabilizes the C3bBb complex. C3b participates in the C3 convertase to generate additional C3b thereby creating a positive feedback loop as shown by the large arrow. Several of the factors that attenuate the complement pathways, such as decay accelerating factor (DAF), do so by accelerating the decay of the C3 convertase, C3bBb. Without wishing to be bound by theory, some of the complement factor B analogs described herein bind C3b in place of a native complement factor B, thereby competing with native complement factor B for binding to C3b. Some complement factor B analogs of the invention bind C3b to create an inactive complex or a complex with significantly reduced C3 convertase activity as compared to a native C3bBb complex.

The invention also provides complement factor B analogs comprising mutations of amino acids corresponding to those in complement factor B that interact with factors/molecules that accelerate the decay of the C3bBb complex. In some embodiments, a complement factor B analog comprises mutations of amino acids that interact with DAF. These mutations include, but are not limited to, one or more mutations of amino acids corresponding to amino acids 290, 291, 323, 363, 364, or 407 of SEQ ID NO:1. In some embodiments, these mutations are a substitution or deletion of one or more of the amino acids corresponding to amino acids 290, 291, 323, 363, 364, or 407 of SEQ ID NO:1. In some embodiments, a complement factor B analog comprises one or more of the following mutations corresponding to K323E, K290A, K291A, Y363A, S364A or D407N of SEQ ID NO:1. In some embodiments, a complement factor B analog comprises one of the following combinations of mutations corresponding to K290A/K291A, Y363A/S364A or K290A/K291A/Y363A/S364A of SEQ ID NO:1. Without wishing to be bound by theory, mutations of amino acids in a complement factor B analog that interact with factors/molecules that accelerate the decay of the C3bBb complex, may inhibit the decay of complexes of C3b and a complement factor B analog of the invention, thereby allowing for a complement factor B analog to better inhibit complement activity.

Exemplary procedures for generating cDNAs (e.g., human wild type fB and three complement factor B analogs as well as four analogous murine sequences) and their incorporation into vectors are detailed in Example 8 of PCT Publication No. WO08/106644 and U.S. Patent Publication No. US20100120665.

Nucleic Acids

The invention includes nucleic acids comprising a nucleotide sequence encoding a complement factor B protein analog of the invention and includes vectors comprising these nucleic acids.

To ensure local and long term expression of a nucleic acid of interest, some embodiments of the invention contemplate transducing a cell with a nucleic acid or vector encoding a complement factor B analog of the invention. The instant invention is not to be construed as limited to any one particular nucleic delivery method, and any available nucleic acid delivery vehicle with either an in vivo or in vitro nucleic acid delivery strategy, or the use of manipulated cells (such as the technology of Neurotech, Lincoln, R.I., e.g., see U.S. Pat. Nos. 6,231,879; 6,262,034; 6,264,941; 6,303,136; 6,322,804; 6,436,427; 6,878,544) as well as nucleic acids of the invention encoding a complement factor B analog per se (e.g., "naked DNA"), can be used in the practice of the instant invention. Various delivery vehicles, such as vectors, can be used with the present invention. For example, viral vectors, amphitrophic lipids, cationic polymers, such as polyethylenimine (PEI) and polylysine, dendrimers, such as combburst molecules and starburst molecules, nonionic lipids, anionic lipids, vesicles, liposomes and other synthetic nucleic acid means of gene delivery (e.g., see U.S. Pat. Nos. 6,958,325 and 7,098,030; Langer, Science 249:1527-1533 (1990); Treat et al., in "Liposomes" in "The Therapy of Infectious Disease and Cancer"; and Lopez-Berestein & Fidler (eds.), Liss, N.Y., pp. 317-327 and 353-365 (1989); "naked" nucleic acids and so on can be used in the practice of the instant invention.

A vector is a means by which a nucleic acid of interest (e.g., a therapeutic nucleic acid, e.g., that can encode a therapeutic protein) is introduced into a target cell of interest. A vector is typically constructed or obtained from a starting material, such as a nucleic acid capable of carrying a foreign gene or transgene and which is capable of entering into and being expressed in a target cell. Suitable starting materials from which a vector can be obtained include transposons, plasmids, viruses, PCR products, cDNAs, mRNAs and so on, as known in the art. Methods for obtaining or constructing a vector of interest include, but are not limited to, standard gene manipulation techniques, sequencing reactions, restriction enzymes digests, polymerase reactions, PCR, PCR SOEing, ligations, recombinase reactions (e.g., Invitrogen's GATEWAY® technology) other enzymes active on nucleic acids, bacteria and virus propagation materials and methods, chemicals and reagents, site directed mutagenesis protocols and so on, as known in the art, see, for example, the Maniatis et al. text, "Molecular Cloning."

Nucleic acids of the invention will typically comprise a promoter operatively linked to a complement factor B protein analog coding sequence. A promoter may be a tissue specific promoter, a cell specific promoter, an inducible promoter, a repressible promoter, a constitutive promoter, a synthetic promoter or a hybrid promoter, for example. Examples of promoters useful in the constructs of the invention include, but are not limited to, a phage lambda (PL) promoter; an SV40 early promoter; a herpes simplex viral (HSV) promoter; a cytomegalovirus (CMV) promoter, such as the human CMV immediate early promoter; a tetracycline-controlled trans-activator-responsive promoter (tet) system; a long terminal repeat (LTR) promoter, such as a MoMLV LTR, BIV LTR or an HIV LTR; a U3 region promoter of Moloney murine sarcoma virus; a Granzyme A promoter; a regulatory sequence(s) of the metallothionein gene; a CD34 promoter; a CD8 promoter; a thymidine kinase (TK) promoter; a B19 parvovirus promoter; a PGK promoter; a glucocorticoid promoter; a heat shock protein (HSP) promoter, such as HSP65 and HSP70 promoters; an immunoglobulin promoter; an MMTV promoter; a Rous sarcoma virus (RSV) promoter; a lac promoter; a CaMV 35S promoter; and a nopaline synthetase promoter. In some embodiments, a promoter is an MND promoter (Robbins et al., 1997, J. Virol. 71:9466-9474), or an MNC promoter, which is a derivative of the MND promoter in which the LTR enhancers are combined with a minimal CMV promoter (Haberman et al., J. Virol. 74(18):8732-8739, 2000).

In some embodiments, a vector of the invention comprises an intron, e.g., as part of the gene coding for a complement factor B protein analog. Heterologous introns are known and non-limiting examples include a human β-globin gene intron. An intron can be from a complement factor B gene or a heterologous intron.

Signal sequences or leader sequences are known and can be used in complement factor B analog expression constructs. Signal sequences are translated in frame as a peptide attached to the amino-terminal end of a polypeptide of choice, the secretory signal sequence will cause the secretion of the polypeptide by interacting with the machinery of the host cell. As part of the secretory process, this secretory signal sequence will be cleaved off. The human placental alkaline phosphatase secretory signal sequence is an example of a useful signal sequence. The present invention is not limited by specific secretory signal sequences and others are known to those skilled in the art. The term "signal sequence" also refers to a nucleic acid sequence encoding the secretory peptide. If a signal sequence is included, it can either be a wild type complement factor B sequence, a homologous sequence, or a heterologous sequence.

Viral Vectors

The present invention includes viral vectors encoding a complement factor B analog(s) of the invention. Examples of viral vectors useful in the present invention are described in PCT Publication No. WO08/106644 and U.S. Patent Publication No. US20100120665. The present invention is not limited to a particular viral vector. Viral vectors include, but are not limited to, retroviral vectors, lentiviral vectors, adenoviral vectors (see, for example, U.S. Pat. No. 7,045,344), AAV vectors (e.g., see U.S. Pat. No. 7,105,345), Herpes viral vectors (e.g., see U.S. Pat. Nos. 5,830,727 and 6,040,172), hepatitis (e.g., hepatitis D) viral vectors (e.g., see U.S. Pat. No. 5,225,347), SV40 vectors, EBV vectors (e.g., see U.S. Pat. No. 6,521,449) and Newcastle disease virus vectors (e.g., see U.S. Pat. Nos. 6,146,642, 7,442,379, 7,332,169 and 6,719,979). In some embodiments, a lentiviral vector is an HIV, EIAV, SIV, FIV or BIV vector. The invention also provides a cell that produces a viral vector of the invention.

Examples of BIV systems are described, for example, in Matukonis et al., 2002 Hum. Gene Ther. 13, 1293-1303; Molina et al., 2002 Virology. 304, 10-23; Molina et al., 2004 Hum. Gene Ther., 15, 65-877; U.S. Pat. Nos. 6,864,085, 7,125,712, 7,153,512; PCT Publication No. WO08/106644 and U.S. Patent Publication No. US20100120665.

Vector virions of the invention may be administered in vivo or in vitro to cells (e.g., mammalian cells). Vectors (viral or nonviral) can be used to transduce or transform cells including, but not limited to, undifferentiated cells, differentiated cells, somatic cells, primitive cells and/or stem cells. In some embodiments, stem cells are intended for administration to a human and not for implantation in a suitably pseudopregnant woman for differentiation and development into an infant.

In some embodiments, a viral vector of the invention comprises a decay accelerating factor (DAF). For example, an enveloped viral vector includes a DAF on the viral membrane. In some embodiments, a DAF is a wild-type DAF. In some embodiments, a DAF is part of a fusion protein with an envelope protein, e.g., see Guibinga et al. Mol Ther. 2005 11(4):645-51. In some embodiments, a BIV producer cell expresses a DAF.

Production of Complement Factor B Analogs of the Invention

The complement factor B protein analogs of the invention can be produced from a cell. In some embodiments, the complement factor B protein analog is then purified from the cell and/or from cell culture medium.

The invention includes (i) cells comprising a nucleic acid comprising a nucleotide sequence encoding a complement factor B analog of the invention and/or (ii) cells expressing a complement factor B protein analog of the invention. In some embodiments, a mammalian cell is utilized. In some embodiments, a prokaryotic cell is utilized.

Host cells are typically transfected or transduced with an expression or cloning vector for protein production and cultured in conventional nutrient media modified as appropriate for inducing promoters, selecting transformants, amplifying the genes encoding the desired sequences or for downstream purification and/or concentration procedures.

Suitable host cells for cloning or expressing a coding region in a vector are prokaryote, yeast, or higher eukaryote cells. Suitable prokaryotes for this purpose include, but are not limited to, eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P), *Pseudomonas* such as *P. aeruginosa*, and *Streptomyces*. In some embodiments, an *E. coli* cloning host is *E. coli* 294 (e.g., ATCC 31,446), although other strains such as *E. coli* B, *E. coli* X1776 (e.g., ATCC 31,537), and *E. coli* W3110 (e.g., ATCC 27,325) may be suitable.

In addition to prokaryotes, eukaryotic microbes such as filamentous fungi or yeast are suitable cloning or expression hosts. *Saccharomyces cerevisiae*, or common baker's yeast, is commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (e.g., ATCC 12,424), *K. bulgaricus* (e.g., ATCC 16,045), *K. wickeramii* (e.g., ATCC 24,178), *K. waltii* (e.g., ATCC 56,500), *K. drosophilarum* (e.g., ATCC 36,906), *K. thermotolerans*, and *K. marxiamis; yarrowia* (e.g., EP402,226); *Pichia pastoris* (e.g., EP183,070); *Candida; Trichoderma reesia* (e.g., EP244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells, e.g., for the expression of glycosylated proteins, can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mor* have been identified and can be used for expressing proteins. A variety of viral strains for transfection can be used for protein expression and are publicly available, e.g., the L-1 variant of *Autographa californica* NPV and the Bm-5 strain of *Bombyx mor* NPV, and such viruses may be used according to the present invention, for example, for transfection of *Spodoptera frugiperda* cells. Plant cell cultures of cotton, corn, potato, soybean, petunia, tomato, and tobacco can also be utilized as hosts.

Some embodiments of the invention utilize vertebrate or mammalian cells, and propagation of vertebrate cells in culture (tissue culture) can be a routine procedure. Examples of useful mammalian host cell lines are a monkey kidney CVI cell line transformed by SV40 (e.g., COS-7, ATCC CRL 1651); human embryonic kidney line (e.g., 293 or 293T cells including either cell line subcloned for growth in suspension culture, Graham et al., J. Gen Virol. 36:59 (1977) such as 293 Freestyle (Invitrogen, Carlsbad, Calif.)) or 293FT; baby hamster kidney cells (e.g., BHK, ATCC CCL 10); Chinese hamster ovary cells; Chinese hamster ovary cells/-DHFR (e.g., CHO, Urlaub et al., Proc. Natl. Acad. Sci. USA 77:4216 (1980)); mouse sertoli cells (e.g., TM4, Mather, Biol. Reprod. 23:243-251 (1980)); monkey kidney cells (e.g., CVI ATCC CCL 70); African green monkey kidney cells (e.g., VERO-76, ATCC CRL-1587); human cervical carcinoma cells (e.g., HELA, ATCC CCL 2); canine kidney cells (e.g., MOCK, ATCC CCL 34); CF2TH cells; buffalo rat liver cells (e.g., BRL 3A, ATCC CRL 1442); human lung cells (e.g., W138, ATCC CCL 75); human liver cells (e.g., Hep G2, HB 8065); mouse mammary tumor cells (e.g., MMT 060562, ATCC CCL51); TRI cells (Mather et al., Annals N.Y. Acad. Sci. 383:44-68 (1983)); MRC 5 cells; and FS4 cells.

In some instances, a host cell may be modified to decrease or eliminate expression of an endogenous protein. For example, if a complement factor B protein analog is to be produced in a particular host cell (e.g., a CHO cell), then the host cell could be modified so as expression of the host cell's native factor B protein (e.g., hamster factor B) is reduced or eliminated. This may be advantageous for the downstream purification of the complement factor B protein analog. Therefore, the invention provides a method of producing a complement protein analog of the invention comprising reducing or eliminating the expression of the corresponding native complement protein in the host cell. Methods for reducing, eliminating or knocking out expression of a host cell protein are known in the art. For example, a protein's expression level may be reduced or eliminated by engineering the host cell to express inhibitory RNA (e.g., RNAi) specific for the RNA coding for the protein. For example, Clontech (Mountain View, Calif.) sells various vectors and kits, such as those referred to as part of the KNOCKOUT™ RNAi Systems, for knocking down expression of proteins in a host cell. Other methods include gene targeting by homologous recombination which allows the introduction of specific mutations into any cloned gene, e.g., see Current Protocols in Molecular Biology, John Wiley & Sons, Inc., 1994-1998, Sections 9.16 and 9.17. This can be used to knockout the gene expressing the host cell protein.

Another method which may be utilized to reduce expression of an endogenous protein, involves using a targeted transcription factor that represses expression of the endogenous protein. For example, a repressor domain from a transcription factor may be attached or fused to a DNA binding domain such as a zinc finger polypeptide. One skilled in the art can design zinc finger polypeptides that bind specific DNA sequences, e.g., see U.S. Pat. Nos. 6,140,081; and 7,067,617; and U.S. Published Patent Applications 20060078880; 20040224385; and 20070213269. One skilled in the art can associate designed zinc finger polypeptides with a transcriptional repressor domain (e.g., a KRAB (Krüppel-associated box) domain). Examples of such molecules and techniques are described in Beerli el al. (Proc Natl Acad Sci USA. 2000 97(4):1495-1500) and U.S. Published Patent Application 20070020627. In some embodiments of the invention, a host cell would be transduced with a vector expressing the transcriptional repressor. This approach has an advantage over knocking out the gene of interest using homologous recombination because, in most cases, a host cell will be diploid and it would be desirable to knock out both gene copies. Whereas, expression of a transcriptional repressor should repress expression of both gene copies.

The expression of particular endogenous protein may also be reduced using compounds that will directly or indirectly reduce the expression of the particular endogenous protein. Using fB as an example, various compounds can be used to reduce the expression of endogenous fB expression. For example, fB protein expression has been shown to be inhibited by histamine (Falus & Meretey, Immunology 1987 60:547-551 and Falus & Meretey, Mol Immunol 1988 25(11):1093-97), sodium butyrate (Andoh et al. Clin Exp Immuno 1999 118:23-29), a glucocorticoid such as dexamethasone (Dauchel et al, Eur J Immunol 1990 20(8):1669-75), platelet derived growth factor (Circolo et al. 1990 The Journal of Biol Chem 265(9):5066-5071), epidermal growth factor (Circolo el al. 1990), and fibroblast growth factor (Circolo et al. 1990). A host cell of the invention may be cultured in the presence of any one or combination of these molecules to reduce the endogenous expression of complement factor B protein. Therefore, in some embodiments of the invention, a host cell expressing a complement factor B protein analog is cultured in the presence of any one or more compounds selected from the group consisting of a histamine, a sodium butyrate, a glucocorticoid (e.g., dexamethasone), a platelet derived growth factor, an epidermal growth factor, or a fibroblast growth factor.

Various compounds and proteins have been shown to upregulate or maintain expression of complement factor B protein. For example, complement factor B protein expression has been shown to be upregulated or maintained by tumor necrosis factor (TNF) (Andoh et al, Clin Exp Immuno 1999 118:23-29), estrogen (Sheng-Hsiang et al. Biology of Reproduction 2002 66:322-332), Interleukin-1 (Dauchel et al. Eur J Immunol 1990 20(8):1669-75), dexamethasone (Lappin & Whaley, Biochem J 1991 280:117-123), prednisolone (Lappin & Whaley 1991), cortical (Lappin & Whaley 1991), and Interferon-gamma (Huang et al, 2001 Eur J Immunol 31:3676-3686). A host cell of the invention may be cultured in the absence of any one or combination of these molecules to reduce the endogenous expression of complement factor B protein. Additionally, a host cell may be cultured in the presence of an inhibitor of any one or more of these compounds. Therefore, in some embodiments of the invention, a host cell expressing an complement factor B protein analog is cultured in the presence of any one or more compounds that inhibit a compound selected from the group consisting of a TNF, estrogen, interleukin-1, dexamethasone, prednisolone, cortical, and interferon-gamma. In some embodiments, expression by the host cell of one or more of these compounds is reduced, e.g., using methods as described herein. Examples of inhibitors of estrogen include, but are not limited to, tamoxifen. Inhibitors also include antibodies that bind and reduce the activity of the compound. For example, various antibodies that bind and inactivate TNF are know in the art.

A complement factor B protein analog containing composition prepared from cells can be purified using, for example, hydroxylapatite chromatography, gel electrophoresis, dialysis, size exclusion chromatography, affinity chromatography, immunoaffinity chromatography, tangential flow purification, diafiltration, ion exchange chromatography, hydrophobic interaction chromatography (HIC), reverse phase chromatography, heparin sepharose affinity chromatography and other known forms of separation and concentration. Following any preliminary purification step(s), a mixture comprising a complement factor B protein analog and contaminants, if any, may be subjected to low pH hydrophobic interaction chromatography, e.g., using an elution buffer at a pH between about 2.5-4.5, in some cases performed at low salt concentrations (e.g., from about 0-0.25M salt) or other procedures for further purification.

In some embodiments, a complement factor B protein analog of the invention is at least 90%, at least 93%, at least 95%, at least 98%, at least 99.5% or at least 99.9% pure in relation to total protein.

The invention also provides methods of producing a complement factor B protein analog comprising expressing in a cell a complement factor B protein analog of the invention and purifying the complement factor B protein analog.

Complement Mediated Conditions/Diseases

There are three pathways of complement activation, the classical pathway, the alternative pathway, and the lectin pathway (FIG. 1). Described herein are examples of complement factor B protein analogs of the invention. In some embodiments, these complement factor B protein analogs can attenuate the alternative pathway of complement activation. However, based on the way all three complement pathways intersect, these analogs can diminish inflammation caused by any of the three complement pathways and thereby provide therapy for any illness whose etiology involves, at least in part, complement activation. These include, but are not limited to, early AMD, wet AMD, and geographic atrophy. FIGS. 1A and 1B outline complement pathways. Note that they intersect at C3b.

The invention provides methods of treating a complement-mediated disease comprising administering to a patient a pharmaceutical preparation of the invention, a complement factor B analog of the invention or a nucleic acid or vector encoding a complement factor B analog of the invention. The invention also includes methods of inhibiting complement activity, wherein the method comprises administering to a human subject a mutated human complement factor B analog in an amount sufficient to inhibit a complement pathway by competing with binding of native complement factor B in the subject, wherein the mutated human complement factor B analog is an active complement factor B analog of SEQ ID NO:4 having cysteine amino acids that form disulfide bonds and a free cysteine amino acid that has been substituted by an amino acid selected from the group consisting of histidine, isoleucine, leucine, methionine, phenylalanine, serine, threonine, tyrosine, and valine. In some embodiments, the mutated complement factor B analog comprises SEQ ID NO:2, 3, 22 or 23.

The invention also provides methods of inhibiting complement activity, wherein the methods comprise introducing to a site of the complement activity a complement factor B analog of the invention, a nucleic acid of the invention, a viral vector of the invention, a pharmaceutical composition/preparation of the invention, or any combination thereof in an amount sufficient to inhibit the complement activity. In some embodiments, a method of the invention utilizes a complement factor B an analog of SEQ ID NO:4 having cysteine amino acids that form disulfide bonds and a free cysteine amino acid that has been substituted by another amino acid.

The invention provides methods of inhibiting complement activity, wherein the methods comprise introducing to a site of the complement activity a mutated human complement factor B analog in an amount sufficient to inhibit the complement activity by the mutated human complement factor B analog competing with binding of native complement factor B, wherein the mutated human complement factor B analog is an active complement factor B analog of SEQ ID NO:4 having cysteine amino acids that form disulfide bonds and a free cysteine amino acid that has been substituted by an amino acid. In some embodiments, this method utilizes a complement factor B analog comprising amino acids 26-764 of SEQ ID NO:2, amino acids 26-764 of SEQ ID NO:3, amino acids 26-990 of SEQ ID NO:22 or amino acids 26-990 of SEQ ID NO:23.

Complement pathways are a part of the immune system known as the innate immune system that provides immediate protection from infection prior to activation of the humoral and cell mediated branches of the immune system. They are activated and inactivated through cascading reactions that exhibit high order kinetics but are remarkably well-regulated. The alternative complement pathway, in particular, has evolved to cycle up with great rapidity through a positive feedback loop.

Complement factor B protein analogs of the invention and/or the vectors that express them may advantageously be used for local and/or systemic administration to a mammal and/or to treat chronic diseases. In some embodiments of the invention, a complement factor B analog inhibits a complement pathway by competing with binding of the native complement factor B, e.g., to C3b protein and/or factor D protein. This can allow attenuation of complement activity as opposed to complete blockade of the pathway. Therefore, it may be possible to downregulate complement activity to a level that is therapeutic (e.g., alleviates some symptoms or their severity) without completely blocking complement activity. Thus, avoiding or decreasing the risks associated with blockage of complement activity, such as increased risk of infection. Therefore, the present invention provides methods for treating a complement mediated disease (e.g., a chronic disease) by local or systemic administration (e.g., i.v., intraperitoneal or oral) of a complement factor B protein analog of the invention.

In some embodiments, the present invention provides compositions and methods for modulating, regulating, inhibiting and/or enhancing a complement activity. Complement-related pathways include, but are not limited to, the classical, lectin and alternative complement pathways. In some cases, a complement-related pathway may play a role in a particular condition, disease or diseases. Therefore, some embodiments of the invention provide methods of regulating, modifying, curing, inhibiting, preventing, ameliorating, slowing progression of and/or treating a disease state mediated by one or more complement-related pathways by administering a complement factor B analog of the invention or a nucleic acid or vector encoding a complement factor B analog of the invention. Such disease states or conditions include, but are not limited to, drusen formation, macular degeneration, AMD, dry eye, corneal ulcers, atherosclerosis, diabetic retinopathy, vitreoretinopathy (Grisanti et al. Invest. Ophthalmol. Vis. Sci. 32:2711-2717), corneal inflammation, airway hyperresponsiveness, immune-related diseases, autoimmune-related diseases, lupus nephritis, systemic lupus erythematosus (SLE), arthritis (e.g., rheumatoid arthritis), rheumatologic diseases, antiphospholipid antibody syndrome, intestinal and renal I/R injury, asthma, atypical hemolytic-uremic syndrome, Type II membranoproliferative glomerulonephritis, non-proliferative glomerulonephritis, fetal loss (e.g., spontaneous fetal loss), glaucoma, uveitis, ocular hypertension, brain injury (e.g., traumatic brain injury), stroke (e.g., see Arumugam et al. PNAS 93(12):5872-6 (1996)), post-traumatic organ damage, thermal trauma (e.g., burn injury) post infarction organ damage (e.g., cardiac, neurological), vasculitis, Kawasaki disease, hereditary angioedema (HAE), paroxysmal nocturnal hemoglobinuria (PNH, sometimes referred to as Marchiafava-Micheli syndrome), colitis, inflammatory bowel disease, tumor metastasis, ischemic-reperfusion injury, cerebrovascular accident, Alzheimer's disease, transplant rejection (e.g., xeno and allo), infections, sepsis, septic shock, Sjögren's syndrome, myasthenia gravis, antibody-mediated skin diseases, all antibody-mediated organ-specific diseases (including Type I and Type II diabetes mellitus, thyroiditis, idiopathic thrombocytopenic purpura and hemolytic anemia, and neuropathies), insulin resistance syndrome (e.g., see Weyer et al. (2000) Diabetes Care, 23(6):779-785), gestational diabetes, multiple sclerosis, psoriasis, cardiopulmonary bypass injury, polyarteritis nodosa, Henoch Schonlein purpura, serum sickness, Goodpasture's disease, systemic necrotizing vasculitis, post streptococcal glomerulonephritis, idiopathic pulmonary fibrosis (usual interstitial pneumonitis), membranous glomerulonephritis, myocarditis (e.g., autoimmune myocarditis) (Kaya et al. Nat Immunol. 2001; 2(8):739-45), myocardial infarction, muscular dystrophy (e.g., associated with dystrophin-deficiency), acute shock lung syndrome, adult respiratory distress syndrome, reperfusion, and/or a complement mediated disease.

In some embodiments, a complement-mediated disease is a disease of the eye. In some embodiments, a complement factor B analog or pharmaceutical composition is administered to the eye, for example, by intravitreal injection, subretinal injection, injection to the intraanterior chamber of the eye, injection or application locally to the cornea, subconjunctival injection, subtenon injection, or by eye drops. In some embodiments, a pharmaceutical composition is administered to the eye, wherein the pharmaceutical composition comprises at least one complement factor B analog, e.g., selected from the group hfB3-292S (SEQ ID NO:2), hfB3-292S-740N (SEQ ID NO:3), hfB3-292S-Fc (SEQ ID NO:22) and hfB3-292S-740N-Fc (SEQ ID NO:23).

Age-related macular degeneration (AMD) is the most common cause of decreased vision in individuals over 65 years of age in the developed world. Dry AMD is characterized by a progressive degeneration of the macula causing central field visual loss. A more acute debilitating AMD includes florid neovascularization and extravasation in the retina, known as wet AMD. There is currently no effective therapy for AMD.

A characteristic of AMD is the accumulation of drusen, located between the basal lamina of the retinal pigment epithelium (RPE) and the inner layer of Bruch's membrane (Pauleikhoff et al., 1990 Am. J. Ophthalmol. 109, 38-43; Bressler et al., 1990 Arch. Ophthalmol. 108, 1442-1447). Drusen, as well as other age-related changes that occur proximal to Bruch's membrane, are believed to contribute to the dysfunction and degeneration of the RPE and retina by inducing ischemia as well as restricting the exchange of nutrient and waste products between the retina and choroid (reviewed by Bird, 1992 Pathophysiology of AMD. In *Age-Related Macular Degeneration: Principles and Practice* (Hampton, G., and Nelsen, P. T., eds.) Chap. 3, Raven Press, New York). Several studies have indicated immune-mediated processes in the development of AMD. Importantly, autoantibodies were detected in the sera of AMD patients (Penfold et al., 1990 Graefes Arch. Clin. Exp. Ophthalmol. 228, 270-274), as predicted by the hypothesis that immune and inflammatory-mediated processes are involved in the development and/or removal of drusen.

The formation of drusen in the eye can be associated with various diseases such as macular degeneration. In some cases, drusen formation and/or its association with a disease has been implicated to be related to complement activity. Some embodiments of the invention provide compositions and methods for modulating, regulating, inhibiting, reducing, retarding and/or reversing the formation or growth of drusen in an animal, such as a human. For example, compositions or molecules of the invention may be delivered to drusen (e.g., by direct injection into drusen (intradrusen injection), adjacent to drusen or intravitreal injection). Some embodiments of the invention can be utilized to slow the progression of macular degeneration, possibly by inhibiting drusen formation. Vitronectin, an abundant component of drusen, is also a component of extracellular deposits associated with atherosclerosis (Niculescu et al., 1989 Atherosclerosis, 78, 197-203), amyloidosis (Dahlback et al., 1993 J. Invest. Dermatol. 100, 166-170), elastosis (Dahlback et al., 1988 Acta Derm. Venereol. 68, 107-115), and MPGN type II (Jansen et al., 1993 Am. J. Pathol. 143, 1356-1365). Vitronectin is a multifunctional protein that functions in cell adhesion, maintenance of hemostasis, and inhibition of complement-induced cell lysis (Preissner, 1991 Ann. Rev. Cell Biol. 7, 275-310). Furthermore, atherosclerotic plaques share a number of other constituents with drusen, such as complement components and apoliproprotein E. An association between advanced AMD and atherosclerosis of carotid arteries was reported in an epidemiological study (Vingerling et al., 1995 Am. J. Epidemiol. 142, 404-409) and another study identified a significant correlation between elastotic degeneration of nonsolar-exposed dermis and choroidal neovascularization in AMD patients (Blumenkranz et al., 1986 Ophthalmology, 93, 552-558). Finally, amyloid β peptide, a major constituent of neuritic plaques in Alzheimer's disease, is also found in drusen (Johnson et al., 2002 Proc. Natl. Acad. Sci. USA, 99, 11830-11835). Amyloid β peptide has been implicated as a primary activator of complement (Bradt et al., 1998 J. Exp. Med. 188, 431-438).

Comprehensive analysis of the molecular composition of human drusen, as well as of the RPE cells that flank or overlie drusen, demonstrated immunoreactivity to immunoglobulins and components of the complement system that are associated with immune complex deposition (Johnson et al., 2000 Exp. Eye Res. 70, 441-449). Drusen also contains multifunctional proteins such as vitronectin (Hageman et al., 1999 FASEB J. 13, 477-484) and apolipoprotein E (Anderson et al., 2001 Am. J. Ophthalmol. 131, 767-781) that play a role in immune system modulation. In addition, molecules involved in the acute phase response to inflammation, such as amyloid P component and $\alpha_1$-antitrypsin, have also been identified in drusen (Mullins et al., 2000 The FASEB Journal, 14, 835-846), as well as proteins involved in coagulation and fibrinolysis (factor X, thrombin, and fibrinogen) (Mullins et al., 2000 The FASEB Journal, 14, 835-846). Drusen formation and associated RPE pathology were suggested to contribute to a chronic inflammatory response that activates the complement cascade (Hageman et al., 2001 Prog. Retin, Eye Res. 20, 705-732; Johnson et al., 2001 Exp. Eye Res. 73, 887-896).

One other form of an optic disorder arising from AMD and resulting in perturbations of the retina is geographic atrophy, which leads to death of patches of rod and cone cells, as well as of the RPE cells.

Atherosclerosis has been shown to typically involve complement related pathways, e.g., see Niculescu et al. Immunologic Research, 30(1):73-80(8) (2004) and Niculescu and Horea, immunologic Research 30(1):73-80 (2004). Complement activation and C5b-9 deposition typically occurs both in human and experimental atherosclerosis. C5b-9 may be responsible for cell lysis, and sublytic assembly of C5b-9 induces smooth muscle cell (SMC) and endothelial cell (EC) activation and proliferation. Complement C6 deficiency has a protective effect on diet-induced atherosclerosis, suggesting that C5b-9 assembly is required for, or at least plays a significant role, in the progression of atherosclerotic lesions, e.g., see Niculescu and Horea, immunologic Research 30(1):73-80 (2004). Some embodiments of the invention may be used to inhibit the formation of C5b-9 and/or inhibit atherosclerosis. In some embodiments, a complement factor B protein analog of the invention is administered to a site or potential site of atherosclerosis. This complement factor B protein analog inhibits a pathway (e.g., the classical and/or alternative complement pathway) which in turn inhibits the formation or activation of C5b-9 or another complement pathway related compound involved in atherosclerosis. There may be other complement related proteins involved in atherosclerosis whose formation and/or activation may be inhibited or blocked in a similar manner.

Airway hyperresponsiveness (AHR) is characteristic of various diseases including, but not limited to, asthma (e.g., allergic asthma). AHR has been shown to typically involve complement related pathways, e.g., see Taube et al., 2006 PNAS 103(20:8084-8089; Park et al., American Journal of Respiratory and Critical Care Medicine 169:726-732, (2004); Thurman and Holers, J Immunology 176:1305-1310 (2006) and U.S. Patent Publication No. 20050260198. Park et al. showed that Crry-Ig administered by intraperitoneal injection had an effect on AHR. Some embodiments of the invention provide compositions and methods for modulating, regulating, inhibiting and/or reducing AHR in an animal, such as a human. Specific AHR related diseases that may be treated, alleviated, inhibited and/or ameliorated include, but are not limited to, asthma, chronic obstructive pulmonary disease (COPD), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus (RSV) infection, parainfluenza virus (PIV) infection, rhinovirus (RV) infection, Hantaan virus (e.g., four-corners strain) and adenovirus infection Immune-related diseases such as autoimmune-related diseases, HLA-B27 associated inflammatory diseases, lupus nephritis and systemic lupus erythematosus (SLE) have been shown to typically involve complement related pathways, e.g., see Thurman and Holers, Immunology 176:1305-1310 (2006). Lupus nephritis is one complication of SLR It is related to the autoimmune process of lupus, where the immune system produces antibodies (antinuclear antibody and others) against body components. Complexes of these antibodies and complement components typically accumulate in the kidneys and result in an inflammatory response. Some embodiments of the invention provide methods and compositions for regulating, modifying, curing, inhibiting, preventing, ameliorating and/or treating an immune-related disease, e.g., involving or related to a complement pathway, such as SLE.

Arthritis has been shown to typically involve complement related pathways, e.g., see Thurman and Holers, J. Immunology 176:1305-1310 (2006) and Banda et al. J Immunol. 177(3):1904-12 (2006). The alternative complement pathway plays a significant role in the induction of arthritis and the alternative complement pathway may even be required. Some embodiments of the invention provide methods and compositions for regulating, modifying, curing, inhibiting, preventing, ameliorating and/or treating arthritis, e.g., rheumatoid arthritis or inflammatory arthritis.

Paroxysmal nocturnal hemoglobinuria (PNH) a potentially life-threatening disease of the blood characterized by complement-induced intravascular hemolytic anemia and thrombosis due to intravascular destruction of red blood cells (RBCs) by complement resulting in uncontrolled amplification of the complement system that leads to destruction of the RBC membrane. Persons with this disease typically have blood cells that are missing a gene called PIG-A. This gene allows a substance called glycosyl-phosphatidylinositol (GPI) to help certain proteins stick to cells. Without PIG-A, complement regulating proteins cannot connect to the cell surface and protect the cell from complement. Some embodiments of the invention provide methods and compositions for regulating, modifying, curing, inhibiting, preventing, ameliorating and/or treating Paroxysmal nocturnal hemoglobinuria.

Hereditary angioedema (HAE) is a potentially life-threatening genetic condition typically caused by a deficiency of the C1 inhibitor, a protein of the complement system. Symptoms include episodes of edema (swelling) in various body parts including the hands, feet, face and airway. Hereditary angioedema (HAE) exists in three forms, all of which are caused by a genetic mutation that is inherited in an autosomal dominant form. Types I and II are caused by mutations in the SERPING1 gene, which result in either diminished levels or dysfunctional forms of the C1-inhibitor protein (type I HAE). Type III HAE has been linked with mutations in the F12 gene, which encodes the coagulation protein Factor XII. All forms of HAE lead to abnormal activation of the complement system. Some current treatments include Ecallantide a peptide inhibitor of kallikrein (e.g., see U.S. Patent Publication No. US20070213275), Icatibant (Firazyr, Jerini) which is a selective bradykinin receptor antagonist, and Cinryze (Viropharma, Inc.) a C1 esterase inhibitor. Some embodiments of the invention provide methods and compositions for regulating, modifying, curing, inhibiting, preventing, ameliorating and/or treating Paroxysmal nocturnal hemoglobinuria.

Glaucoma is a group of diseases of the optic nerve involving loss of retinal ganglion cells in a characteristic pattern of optic neuropathy. Approximately 25% of glaucoma patients with retinal ganglion cell loss have normal ocular pressure. Ocular hypertension (OHT) is a significant risk factor for developing glaucoma and lowering it via pharmaceuticals or surgery is currently the mainstay of glaucoma treatment. Ocular hypertension and glaucoma have been shown to typically involve complement related pathways, e.g., see Khalyfa et al., Molecular Vision, 13:293-308 (2007); Stasi et al. IOVS 47(3):1024-1029 (2007); and Kuehn et al., Experimental Eye Research 83:620-628 (2006). Expression and/or the presence of C1q and C3 have been shown to be higher in retina subjected to OHT. Some embodiments of the invention provide methods and compositions for regulating, modifying, curing, inhibiting, preventing, ameliorating and/or treating glaucoma.

Uveitis has been shown to typically be associated with the complement pathway, e.g., see Mondino and Rao, Investigative Ophthalmology & Visual Science 24:380-384 (1983) and Jha et al. Molecular Immunology 44:3901-3908 (2007). Mondino and Rao found that mean values of all tested complement components in aqueous humor to serum measurements were increased in patients with a history of previous eye surgeries and were highest in patients with anterior uveitis. Some embodiments of the invention provide methods and compositions for regulating, modifying, curing, inhibiting, preventing, ameliorating and/or treating uveitis.

Diabetic retinopathy is one of the leading causes of vision loss in middle-aged individuals. Activation of the complement system is believed to play an important role in the pathogenesis of diabetic retinopathy (e.g., see Jha et al. Molecular Immunology 44:3901-3908 (2007)). Some embodiments of the invention provide methods and compositions for regulating, modifying, curing, inhibiting, preventing, ameliorating and/or treating diabetic retinopathy.

Proliferative vitreoretinopathy (PV) is one of the most common complications of retinal detachment. PV has been linked to complement activity, e.g., see Grisante et al. Invest Ophthalmol Vis Sci. 1991; 32(10):2711-7 and Grisante et al. Ophthalmologe 1992; 89(1):50-4. Some embodiments of the invention provide methods and compositions for regulating, modifying, curing, inhibiting, preventing, ameliorating and/or treating PV.

Anti-phospholipid antibody syndrome, intestinal and renal ischemic reperfusion I/R injury, atypical hemolytic-uremic syndrome, Type II membranoproliferative glomerulonephritis, and fetal loss (e.g., spontaneous fetal loss), have been shown to typically involve complement related pathways, e.g., see Thurman and Holers, J Immunology 176: 1305-1310 (2006).

Brain injury (e.g., traumatic brain injury) has been shown to typically involve complement related pathways, e.g., see Leinhase et al., J Neuroinflammation 4:13 (2007) and BMC Neurosci.7:55 (2006). Leinhase 2006, showed that after experimental traumatic brain injury in wild-type (fB+/+) mice, there was a time-dependent systemic complement activation. In contrast, the extent of systemic complement activation was significantly attenuated in fB−/− mice. Some embodiments of the invention provide methods and compositions for regulating, modifying, curing, inhibiting, preventing, ameliorating and/or treating neuronal cell death, traumatic neural injury (e.g. brain), complement-mediated neuroinflammation and/or neuropathology.

Ischemia-reperfusion injury can cause increases in the production of or oxidation of various potentially harmful compounds produced by cells and tissues, which can lead to oxidative damage to or death of cells and tissues. For example, renal ischemia-reperfusion injury can result in histological damage to the kidneys, including kidney tubular damage and changes characteristic of acute tubular necrosis. The resultant renal dysfunction permits the accumulation of nitrogenous wastes ordinarily excreted by the kidney, such as serum urea nitrogen (SUN). Ischemia-reperfusion may also cause injury to remote organs, such as the lung. Some embodiments of the invention utilize modulators, such as inhibitors, of a complement pathway (e.g., inhibitors of factor B activity), e.g., when administered to an animal that has, or is at risk of experiencing or developing, ischemia-reperfusion. In some embodiments, these modulators, prevent, reduce or inhibit at least one symptom of injury due to ischemia-reperfusion. Other types of ischemia-reperfusion injury, that can be prevented or reduced using methods and compositions of the invention, include, but are not limited to, cardiac ischemia-reperfusion injury such as myocardial infarction or coronary bypass surgery, central nervous system ischemia-reperfusion injury, ischemia-reperfusion injury of the limbs or digits, ischemia-reperfusion of internal organs such as the lung, liver or intestine, or ischemia-reperfusion injury of any transplanted organ or tissue. See, e.g., PCT Publication No. WO03/061765 which discusses myocardial infarction and complement pathways.

Inflammation is a major etiologic determinant of myocardial infarction (Ridker, 2007 Nutr. Rev. 65(12 Pt 2):S253-9). It has also been shown that delivery (e.g., intracoronary) of bone marrow (stem) cells leads to an improvement in systolic function after acute myocardial infarction (Wollert, 2008, Curr. Opin. Pharmacol. January 31 [Epub]). Also, bone marrow stem cells can regenerate infarcted myocardium (Orlic et. al. 2003 Pediatr. Transplant. 7 Suppl 3:86-88). Mesenchymal stem cells have been shown to provide a cardiac protective effect in ischemic heart disease (Guo et al. 2007 Inflammation 30(3-4):97-104). In the present invention, delivery of the stem cells can be by any means, such as intracoronary injection, injection directly into myocardium (e.g., into diseased and/or healthy myocardium (e.g., adjacent to the injured area)). In some embodiments, a mammal is treated with cytokines to mobilize their bone marrow stem cells in the circulation allowing the stem cells to traffic to the myocardial infarct.

Various stem cells have been used in vivo for various applications. One problem with the use of stem cells in vivo is the lower than desired survival and/or seeding of the stem cells, e.g., in the area of interest. One significant reason for low seeding and survival of stems cells can be inflammation at the site. Therefore, the present invention provides a method of treatment and/or a method of improving stem cell survival and/or seeding. In some embodiments, these methods comprise administering a composition of the invention before, during and/or after administration or mobilization of stem cells. In some embodiments, complement inhibitors of the invention act as anti-inflammatory agents that will create a favorable environment for stem cells to home in and survive in the area of desired seeding (e.g., damaged heart or bone marrow) and therefore repair or replace the damaged tissue. Stem cells may be administered in a solution that also contains a complement factor B protein analog of the invention. Stem cells may be, but are not limited to, hematopoietic stem cells, embryonic stem cells, mesenchymal stem cells, neural stem cells, mammary stem cells, olfactory stem cells, pancreatic islet stem cells, totipotent stem cells, multipotent stem cells or pluripotent stem cells. The stem cells may be autologous, allogeneic, or syngeneic.

Complement activity appears to be involved in muscular dystrophy (e.g., associated with dystrophin-deficiency). For example, see PCT Publication No. WO2007130031, Spuler & Engel 1998 Neurology 50:41-46, and Selcen et al. 2001 Neurology 56:1472-1481. Therefore, some embodiments of the invention provide methods and compositions for regulating, modifying, curing, inhibiting, preventing, ameliorating and/or treating muscular dystrophy.

Complement activity may contribute to corneal inflammation. Therefore, some embodiments of the invention provide methods and compositions for regulating, modifying, curing, inhibiting, preventing, ameliorating and/or treating corneal inflammation, e.g., after surgery. In some embodiments, a complement factor B analog of the invention is administered via eye drops or as otherwise described herein.

In some embodiments, complement factor B analogs of the invention are used for regulating, modifying, curing, inhibiting, preventing, ameliorating and/or treating corneal neovascularization.

Some embodiments of the invention provide methods for enhancing the efficacy of post-coronary or peripheral artery bypass grafting or angioplasty. In some embodiments, a vector of the invention encoding a complement factor B protein analog of the invention (e.g., hfB3-292S or hfB3-292S-740N) is used to transduce cells of a blood vessel (e.g., endothelial cells). In some embodiments, cells of a blood vessel are transduced prior to implantation in an animal. In some embodiments, cells of a blood vessel are transduced in vivo.

Alleviating pain and suffering and inflammation in post-operative patients is an area of special focus in clinical medicine, especially with the growing number of out-patient operations performed each year. Complement factor B analogs of the present invention can be utilized to inhibit inflammation, e.g., by inhibiting a complement activity. Therefore, complement factor B analogs can be used to reduce inflammation, e.g., in postoperative patients. In some embodiments, a complement factor B analog is administered locally (e.g., perioperative delivery) to a site of surgery to inhibit inflammation, which in some cases will reduce pain and suffering. In some embodiments, a complement factor B analog is administered in a solution, e.g., in a physiologic electrolyte carrier fluid. In some embodiments, a complement factor B analog is delivered via perioperative delivery directly to a surgical site of an irrigation solution containing the composition. In some embodiments, due to the local perioperative delivery method of the present invention, a desired therapeutic effect may be achieved with lower doses of agents than are necessary when employing other methods of delivery, such as intravenous, intramuscular, subcutaneous and oral. In some embodiments, when used perioperatively, the solution will result in a clinically significant decrease in operative site pain and/or inflammation, thereby allowing a decrease in the patient's postoperative analgesic (e.g., opiate) requirement and, where appropriate, allowing earlier patient mobilization of the operative site. In some embodiments, no extra effort on the part of the surgeon and operating room personnel is required to use the present solution relative to conventional irrigation fluids. In some embodiments, a composition of the invention is used (e.g., in irrigation fluid) for arthroscopy, cardiovascular and general vascular therapeutic and diagnostic procedures, urologic procedures, general surgical wounds and wounds in general. Compositions of the invention may be delivered by, but not limited to, injection (e.g., via syringe), via irrigation fluid, as part of a bandage over a wound, or in a topical application such as a solution, cream, gel or the like.

In some embodiments of the invention, a complement factor B analog and/or vector of the invention is administered in combination with a complement inhibiting factor, prior to, concurrently with, or after administration of the complement factor B analog and/or vector. A complement inhibiting factor includes, but is not limited to, a Factor H, a Factor H-like 1, an MCP, a DAF, or a soluble form of an MCP.

In some embodiments of the invention, a complement factor B analog or vector of the invention is administered in combination with an anti-angiogenic factor. Anti-angiogenic factors include, but are not limited to, endostatin, a VEGF binding molecule, PEDF, T2-TrpRS (e.g., see U.S. Pat. No. 7,273,844), sFLT (e.g., see Kong et al. Hum Gene Ther (1998) 9:823-833), aflibercept (VEGF Trap), VEGF Trap-eye, kininostatin, ranibizumab and bevacizumab.

In some embodiments, a complement factor B analog and/or vector of the invention is administered in combination with LUCENTIS® (ranibizumab), AVASTIN® (bevacizumab), VEGF Trap-eye, aflibercept or a molecule(s) that binds VEGF and/or that inhibits angiogenesis. LUCENTIS® is used to treat wet AMD. Some embodiments of the invention can also be used to treat wet AMD. Therefore, the present invention provides methods and compositions for treating wet AMD comprising administering, separately or together, a composition of the invention in combination with LUCENTIS® (ranibizumab), AVASTIN® (Bevacizumab) VEGF Trap-eye, aflibercept and/or a molecule(s) that binds VEGF and/or that inhibits angiogenesis. Additionally, intraocular inflammation is one of the most common adverse reactions reported after administration of LUCENTIS®, e.g., see the "Full Prescribing Information" for LUCENTIS®. The present invention provides a method for inhibiting or reducing intraocular inflammation (e.g., resulting from the administration of LUCENTIS®) comprising administering a molecule or composition of the invention prior to, at the same time, and/or after the administration of LUCENTIS®, VEGF Trap-eye or aflibercept.

In some embodiments of the invention, a complement factor B analog or vector of the invention is administered in combination with another compound(s), such as a compound that inhibits T-cell activation, B-cells, TNF, interleukin-1 (e.g., interleukin-1b), interleukin-6 and/or interferon-gamma. A complement factor B analog or vector of the invention can also be administered in combination with a compound(s) that inhibits complement activity, e.g., alternative complement activity. Compounds that can be used and which inhibit TNF include, but are not limited to, compounds that bind TNF, such as antibodies (e.g., Infliximab (REMICADE®), Golimumab (SIMPONI®) and Adalimumab (HUMIRA®)) or soluble receptors that bind TNF such as Etanercept (ENBREL®). Other compounds that can be used and which inhibit T-cell activation include, but are not limited to, compounds that bind B7 such as abatacept (ORENCIA®). Also compounds which down-regulate B-cells can be used including, but not limited to, compounds that bind CD20 such as Rituximab (RITUXAN® and MABTHERA®).

Complement pathways contributing to and/or causing a disease can be modulated, regulated, inhibited and/or activated using various methods and/or complement factor B protein analogs that are part of the present invention.

Compositions, Formulations and Preparations

Some embodiments of the invention provide compositions, e.g., pharmaceutical compositions containing a complement factor B analog of the invention, such as for therapeutic uses. In some embodiments, a pharmaceutical composition comprises a complement factor B analog comprising amino acids 26-764 of SEQ ID NO:2, amino acids 26-764 of SEQ ID NO:3, amino acids 26-990 of SEQ ID NO:22 or amino acids 26-990 of SEQ ID NO:23, for example, hfB3-292S (SEQ ID NO:2), hfB3-292S-740N (SEQ ID NO:3), hfB3-292S-Fc (SEQ ID NO:22) or hfB3-292S-740N-Fc (SEQ ID NO:23). In some embodiments, a pharmaceutical composition comprises a complement factor B analog consisting of amino acids 26-764 of SEQ ID NO:2, amino acids 26-764 of SEQ ID NO:3, amino acids 26-990 of SEQ ID NO:22 or amino acids 26-990 of SEQ ID NO:23. Examples of pharmaceutical compositions and formulations that can be used with the complement factor B analogs of the invention are described in PCT Publication No. WO08/106644 and U.S. Patent Publication No. US20100120665.

Some embodiments of the invention include pharmaceutical preparations comprising a complement factor B protein analog of the invention, a nucleic acid of the invention, a viral vector of the invention or any combination thereof.

Formulations (e.g., for injection) are generally, but not necessarily, biocompatible solutions of the active ingredient, e.g., comprising Hank's solution or Ringer's solution. Formulations for transdermal or transmucosal administration generally include, but are not limited, penetrants such as fusidic acid or bile salts in combination with detergents or surface-active agents. In some embodiments, formulations can be manufactured as aerosols, suppositories, or patches. In some embodiments, oral administration may not be favored for protein or peptide active ingredients; however, this type of composition may be suitably formulated, e.g., in an enteric coated form, in a depot, in a capsule and so on, so as to be protected from the digestive enzymes, so that oral administration can also be employed. Some formulations of the invention comprise balanced salt solution (Alcon Laboratories, Inc., Fort Worth, Tex.) or balanced salt solution plus (Alcon Laboratories, Inc.). In some embodiments, a formulation comprises one or more of the following: citrate, NaCl (e.g., 0.64%), potassium chloride (KCl) (e.g., 0.075%), calcium chloride dihydrate ($CaCl_2.2H_2O$) (e.g., 0.048%), magnesium chloride hexahydrate ($MgCl_2.6H_2O$) (e.g., 0.03%), sodium acetate trihydrate ($CH_3CO_2Na.3H_2O$) (e.g., 0.39%), sodium citrate dihydrate ($C_6H_5O_7Na_3.2H_2O$) (e.g., 0.17%), sucrose and sodium hydroxide and/or hydrochloric acid (to adjust pH) and water. The preceding list includes some molecules that are listed as particular hydrates, e.g., dihydrate, trihydrate, hexahydrate, etc. It is understood that various hydrates of these compounds can be used in the present invention and the invention is not limited to these particular hydrate forms of the listed molecules. In some embodiments, a formulation comprises one or more of the following: NaCl, monobasic phosphate monohydrate, dibasic sodium phosphate heptahydrate and hydrochloric acid and/or sodium hydroxide to adjust pH and water. In some embodiments, a pharmaceutical composition comprises at least one ingredient selected from the group consisting of histidine, $MgCl_2$, trehalose, a polysorbate, polysorbate 20, NaCl, sucrose, arginine and proline. In some embodiments, a formulation comprises one or more of the following: histidine (e.g., about 10 mM); α, α-trehalose dehydrate (e.g., about 10% or about 50 mM); $MgCl_2$ (e.g., about 10 mM); a polysorbate such as polysorbate 20 (e.g., about 0.01%); and NaCl (e.g., about 0.1%). In some embodiments, a formulation may comprise one or more of the following: sucrose, arginine or proline. In some embodiments, a formulation comprises or consists of a molecule(s) of the present invention, 10 mM histidine, 10 mM $MgCl_2$, 50 mM trehalose and 0.01% polysorbate 20. In some embodiments, a formulation comprises or consists of a molecule(s) of the present invention, 1.0% NaCl and 10 mM $MgCl_2$. In some embodiments, a formulation comprises or consists of a molecule(s) of the present invention, and a balanced salt solution enriched with bicarbonate, dextrose, and glutathione, such as BSS PLUS®. In some embodiments, a formulation does not comprise trehalose. In some embodiments, a formulation or composition is at a pH of about 5.5. In some embodiments, a formulation or composition is at a pH of between from about 5.0 to 9.0, about 5.0 to 5.5, about 5.3 to 5.7, about 5.5 to 6.0, about 5.8 to 6.2, about 6.0 to 6.5, about 6.3 to 6.7, about 6.5 to 7.0, about 6.8 to 7.2, about 7.0 to 7.5, about 7.3 to 7.7, about 7.5 to 8.0, about 7.8 to 8.2, about 8.0 to 8.5, about 8.3 to 8.7 and about 8.5 to 9.0, whatever is suitable to retain the biological activity and stability of the active ingredient(s).

Some formulations of the invention can be manufactured as aerosols, suppositories, eye drops or patches.

Examples of suitable formulations and formulatory methods for a desired mode of administration may be found in Remington's Pharmaceutical Sciences, latest edition, Mack Publishing Co., Easton, Pa. and in U.S. Pat. No. 7,208,577.

In some embodiments, a composition for use in vivo contains a "carrier" or a "pharmaceutically acceptable carrier". The term "carrier" refers to a diluent, adjuvant, excipient, or vehicle with which the vector of interest is administered. The term "carrier" includes, but is not limited to, either solid or liquid material, which may be inorganic or organic and of synthetic or natural origin, with which an active component(s) of the composition is mixed or formulated to facilitate administration to a subject.

In general, a suitable oil(s), saline, aqueous dextrose (glucose), and related sugar solutions and glycols such as propylene glycol or polyethylene glycols are typically suitable carriers for parenteral solutions. In some embodiments, solutions for parenteral administration contain a water soluble salt of the active ingredient, suitable stabilizing agents, and if desirable or necessary, buffer substances. Antioxidizing agents such as sodium bisulfite, sodium sulfite, or ascorbic acid, either alone or combined, can be used as stabilizing agents. Also used are citric acid and its salts and sodium EDTA. In addition, parenteral solutions can contain preservatives, such as benzalkonium chloride, methyl- or propyl-paraben, and chlorobutanol.

Carriers can include carbohydrates such as trehalose, mannitol, glutathione, xylitol, sucrose, lactose, and sorbitol. Other ingredients for use in formulations may include, for example, DPPC (1,2-Didecanoyl-sn-glycero-3-phosphocholine), DOPE (1,2-Dioleoyl-sn-glycero-3-phosphoethanolamine), DSPC (1,2-Distearoyl-sn-glycero-3-phosphocholinez 1,2-Distearoyl-sn-glycero-3-phosphocholine) and DOPC (1,2-Dioleoyl-sn-glycero-3-phosphocholine). Natural or synthetic surfactants may be used. Polyethylene glycol may be used (even apart from its use in derivatizing a protein). Dextrans, such as cyclodextran, may be used. In some embodiments, cyclodextrin, tertiary amines and/or beta-cyclodextrin may be used. Bile salts and other related enhancers may be used. Cellulose and cellulose derivatives may be used. Amino acids may be used, such as use in a buffer formulation. Also, the use of liposomes, microcapsules or microspheres, inclusion complexes, or other types of carriers is contemplated.

Suitable pharmaceutical excipients include, but are not limited to, starch, glucose, lactose, sucrose, gelatin, antibiotics, preservatives, malt, rice, flour, chalk, silica gel, sodium stearate, glycerol monostearate, talc, sodium chloride, dried skim milk, glycerol, propylene, glycol, water, ethanol and the like. A composition, if desired, can also contain wetting and/or emulsifying agents, and/or pH buffering agents. Where necessary, a composition may also include a solubilizing agent and/or a local anesthetic such as lignocaine to ease pain at the site of the injection.

Also contemplated herein is pulmonary delivery of an agent or protein (or derivative thereof) of the present invention. In some embodiments, a complement factor B analog(s) is delivered to the lungs of a mammal while inhaling and can mostly remain in the lungs or in some embodiments traverses across the lung epithelial lining to the blood stream. (e.g., see Adjei et al., Pharmaceutical Research 7:565-569 (1990); Adjei et al., International Journal of Pharmaceutics 63:135-144 (1990); Braquet et al., Journal of Cardiovascular Pharmacology 13(suppl. 5):s.143-146 (1989); Hubbard et al., Annals of Internal Medicine 3:206-212 (1989); Smith et al., J. Clin. Invest. 84:1145-1146 (1989); Oswein et al., Proceedings of Symposium on Respiratory Drug Delivery II, Keystone, Colo., March, 1990; Debs et al., The Journal of Immunology 140:3482-3488 (1988) and Platz et al., U.S. Pat. No. 5,284,656). Contemplated for use in the practice of this invention are a wide range of mechanical devices designed for pulmonary delivery of therapeutic products, including but not limited to nebulizers, metered dose inhalers, and powder inhalers. Some specific examples of commercially available devices suitable for the practice of some embodiments of the invention are the ULTRAVENT™ nebulizer, manufactured by Mallinckrodt, Inc., St. Louis, Mo.; the ACORN II® nebulizer, manufactured by Marquest Medical Products, Englewood, Colo.; the VENTOLIN metered dose inhaler, manufactured by Glaxo Inc., Research Triangle Park, N.C.; and the SPINHALER powder inhaler, manufactured by Fisons Corp., Bedford, Mass.

In some embodiments, a protein is prepared in particulate form. In some embodiments, this particulate form has an average particle size of less than 10 µm (or microns), most preferably 0.5 to 5 µm, for delivery to the distal lung.

Formulations suitable for use with a nebulizer (e.g., jet or ultrasonic) will typically comprise a complement factor B analog dissolved in water, in some embodiments, at a concentration of about 0.1 to about 25 mg of biologically active protein per mL of solution. A formulation may also include a buffer and/or a simple sugar (e.g., for protein stabilization and regulation of osmotic pressure). A nebulizer formulation may also contain a surfactant, to reduce or prevent surface induced aggregation of a protein(s) caused by atomization of the solution in forming the aerosol.

Formulations for use with a metered-dose inhaler device will generally comprise a finely divided powder containing a complement factor B analog of the invention suspended in a propellant, e.g., with the aid of a surfactant. A propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. In some embodiments, formulations for dispensing from a powder inhaler device will comprise a finely divided dry powder containing a complement factor B analog of the invention and may also include a bulking agent, such as lactose, sorbitol, sucrose, mannitol, trehalose, or xylitol in amounts which facilitate dispersal of the powder from the device, e.g., 50 to 90% by weight of the formulation.

Administration and Delivery

It is understood that when introduction or administration of a nucleic acid encoding a complement factor B protein analog is discussed, that the invention also contemplates the introduction or administration of the complement factor B protein analog itself. It is understood that when introduction of a complement factor B analog is discussed, that the invention also contemplates the introduction of a nucleic acid encoding the complement factor B protein analog.

In some embodiments, complement factor B analogs or compositions of the invention can be administered locally or systemically. Useful routes of administration are described herein and known in the art. Methods of introduction or administration include, but are not limited to, intradermal, intramuscular, intraperitoneal, intravenous, subcutaneous, intranasal, intratracheal, topical, inhaled, transdermal, rectal, parenteral routes, epidural, intracranial, into the brain, intraventricular, subdural, intraarticular, intrathecal, intracardiac, intracoronary, intravitreal, subretinal, intraanterior chamber of the eye, particular, locally on the cornea, subconjunctival, subtenon injection, by applying eyedrops, oral routes, via balloon catheter, via stent or any combinations thereof. In some embodiments, a composition or complement factor B analog of the invention is administered to a drusen, e.g., by injecting directly into a drusen. Systemic administration may be, but is not limited to, by intravenous or intra-arterial injection or by transmucosal, subcutaneous and/or transdermal delivery. In some embodiments, a composition of the invention may be initially directed to a site other than a diseased site. For example regarding AHR which occurs in the lungs of an animal, an intraperitoneal injection of a protein, vector or nucleic acid of the invention may result in a change in AHR in the lungs, e.g., see Park et al., American Journal of Respirator and Critical Care Medicine 169:726-732, (2004). In some embodiments, a dosage level and/or mode of administration of a composition may depend on the nature of the composition, the nature of a condition(s) to be treated, and/or a history of an individual patient. In some embodiments, cells expressing a complement factor B analog of the invention are administered. These cells can be a cell line, xenogeneic, allogeneic or autologous.

In some embodiments, e.g., comprising administration to the eye, a complement factor B protein analog or vector of the invention is administered about once every week, month, 2 months, 3 months, 6 months, 9 months, year, 18 months, 2 years, 30 months, 3 years, 5 years, 10 years or as needed. In some embodiments, e.g., comprising administration to the eye, a molecule or vector of the invention is administered from about every 1 to 4 weeks, about every 4 to 8 weeks, about every 1 to 4 months, about every 3 to 6 months, about every 4 to 8 months, about every 6 to 12 months, about every 9 to 15 months, about every 12 to 18 months, about every 15 to 21 months, about every 18 to 24 months, about every 1 to 2 years, about every 1.5 to 3 years, about every 2 to 4 years, about every 3 to 5 years, about every 5 to 7 years, about every 7 to 10 years or about every 10 to 20 years. It is expected that administration of a vector coding for a complement factor B protein analog would be less frequent than administration of the complement factor B protein analog. In some embodiments of the invention, a pharmaceutical preparation comprises a vector encoding a complement factor B analog of the invention and the pharmaceutical preparation is administered only once to the patient.

In some embodiments, e.g., comprising administration to the eye, a vector coding for a complement factor B analog is administered 1, 2, 3, 4, 5, 6, 7, 8, 9, 10 or more times to a patient in their lifetime. In some embodiments, e.g., comprising administration to the eye, a lentiviral vector of the invention is administered 1, 2, 3, 4, 5, 6, 7, 8, 9, 10 or more times to a patient in their lifetime.

In some embodiments, a complement factor B protein analog of the invention is administered by intravitreal injection to a human eye. In some embodiments, about 15 µg to about 5 mg; about 15 µg to about 500 µg; about 100 µg to about 900 µg; about 300 µg to about 700 µg; about 500 µg to about 1 mg; about 1 mg to about 5 mg; about 1 mg; or about 500 µg of a complement factor B protein analog is administered by intravitreal injection to a human eye.

In some embodiments, a complement factor B protein analog of the invention is administered by subretinal injection or intravitreal injection of a lentiviral or adeno associated viral (AAV) vector. In some embodiments, about $5 \times 10^6$ to about $5 \times 10^8$; about $5 \times 10^6$ to about $5 \times 10^7$; about $5 \times 10^7$ to about $5 \times 10^8$; about $1 \times 10^7$ to about $1 \times 10^8$; about $3 \times 10^7$ to about $5 \times 10^7$; about $2.5 \times 10^7$; about $5 \times 10^7$; about $7.5 \times 10^7$; or about $1 \times 10^8$ transducing units of a lentiviral vector is administered by subretinal injection. In some embodiments, about $5 \times 10^8$ to about $1 \times 10^9$; about $5 \times 10^8$ to about $7.5 \times 10^8$; about $7.5 \times 10^8$ to about $1 \times 10^9$; about $6 \times 10^8$ to about $9 \times 10^8$; about $7 \times 10^8$ to about $8 \times 10^8$; about $5 \times 10^8$; about $6 \times 10^8$; about $7 \times 10^8$; about $8 \times 10^8$; about $9 \times 10^8$; or about $1 \times 10^9$ transducing units of an AAV vector is administered by subretinal injection.

In some embodiments, about $5 \times 10^8$ to about $1 \times 10^{10}$; about $5 \times 10^8$ to about $5 \times 10^9$; about $5 \times 10^8$ to about $2 \times 10^9$; about $2 \times 10^9$ to about $5 \times 10^9$; about $5 \times 10^9$ to about $1 \times 10^{10}$; about $5 \times 10^8$ to about $1 \times 10^9$; about $1 \times 10^9$ to about $3 \times 10^9$; about $3 \times 10^9$ to about $6 \times 10^9$; about $6 \times 10^9$ to about $1 \times 10^{10}$; or about $1 \times 10^9$ to about $1 \times 10^{10}$ transducing units of an AAV vector is administered by intravitreal injection.

In some embodiments, about 50 µl to about 100 µl, about 50 µl to about 75 µl, about 75 µl to about 100 µl, about 60 µl to about 90 µl, about 70 µl to about 80 µl, about 50 µl; about 60 µl; about 70 µl; about 80 µl; about 90 µl; or about 100 µl of a complement factor B protein analog or a vector encoding a complement factor B protein analog is injected subretinally. In some embodiments, about 50 µl to about 1 ml, about 50 µl to about 500 µl, about 500 µl to about 1 ml, about 250 µl to about 750 µl, about 250 µl to about 500 µl, about 500 µl to about 750 µl, about 400 µl to about 600 µl, or about 750 µl to about 1 ml of a complement factor B protein analog or a vector encoding a complement factor B protein analog is injected intravitreally.

In some embodiments, an anti-inflammatory may be delivered in combination with a complement factor B protein analog (e.g., hfB3-292S or hfB3-292S-740N), vector or nucleic acid of the invention. An anti-inflammatory may be delivered prior to, concurrently with, and/or after administration of a molecule or vector of the invention. In some embodiments, an anti-inflammatory is administered in the same solution and/or same syringe as a complement factor B protein analog, nucleic acid or vector of the invention. In some embodiments, a complement factor B protein analog or vector of the invention and an anti-inflammatory are co-administered to the eye, e.g., as described herein.

Many anti-inflammatory drugs are known in the art and include, but are not limited to, dexamethasone, dexamethasone sodium metasulfobenzoate, dexamethasone sodium phosphate, fluorometholone, bromfenac, pranoprofen, RESTASIS™, cyclosporine ophthalmic emulsion, naproxen, glucocorticoids, ketorolac, ibuprofen, tolmetin, non-steroidal anti-inflammatory drugs, steroidal anti-inflammatory drugs, diclofenac, flurbiprofen, indomethacin, and suprofen.

Some embodiments of the invention include administration of both a complement factor B protein analog and a vector encoding it. A complement factor B protein analog of the invention may be delivered prior to, concurrently with, and/or after administration of a vector of the invention. In some embodiments, a complement factor B protein analog of the invention is administered in the same solution and/or same syringe as a vector of the invention. In some embodiments, a complement factor B protein analog of the invention and a vector of the invention are co-administered to the eye, e.g., as described herein.

Additionally, a complement factor B analog or a nucleic acid encoding it can be delivered or administered to an animal via a cell, e.g., as cell therapy. For example, this can be accomplished by administering or delivering a cell(s) expressing a complement factor B analog(s). In some embodiments, a complement factor B analog(s) is expressed from the cell via a regulatable, inducible and/or repressible promoter. In some embodiments, encapsulated cells that express a complement factor B analog(s) are delivered to an animal, e.g., see PCT Publication No. WO07078922 related to encapsulated cells. In some embodiments, cells are administered locally (e.g., in a joint, intravitreal, intraretinal, intracranially etc.) or systemically (e.g., i.v.).

Cells to be administered to an animal can be autologous, allogeneic or xenogeneic. In some embodiments, autologous cells are manipulated ex vivo to cause them to produce a complement factor B protein analog of the invention and, in some embodiments, the cells are introduced back to the animal. Transferring a nucleic acid comprised of a coding region to cells ex vivo can be by any method, such as, electroporation, microinjection, cell fusion, chromosome-mediated gene transfer, microcell-mediated gene transfer, spheroplast fusion, lipofection, microparticle bombardment, calcium phosphate mediated transfection, viral infection and so on. Optionally, a selectable marker also can be introduced into the cells. If a selectable marker is utilized, the cells can be then placed under selection, e.g., to enhance expression and/or to isolate those cells that express the transferred coding region (see, e.g., Loeffler & Behr, Meth. Enzymol. 217:599-618 (1993); Cohen et al., Meth. Enzymol. 217:618-644 (1993); and Cline, Pharmac. Ther. 29:69-92 (1985)).

Recombinant cells (e.g., autologous or allogeneic cells transduced in vitro) can be delivered to a patient by various methods known in the art. For example, cells can be encapsulated prior to administration, as known in the art. In some embodiments, when encapsulated, the cells are not autologous. In some embodiments, recombinant blood cells (e.g., hematopoietic stem and/or progenitor cells) are administered intravenously. In some embodiments, eye cells and/or pluripotential cells can be injected directly into the eye. The amount of cells needed depends on the desired effect, the animal's state, etc.

In some embodiments of the invention, a gene delivery system can result in transduction and/or stable integration of a gene or coding region for a complement factor B analog into a target cell. In some embodiments, target cells are mammalian cells such as primate cells, and human cells. In some embodiments, target cells are cells of the eye, such as retinal pigment epithelial cells, retinal cells, or pluripotential cells. Target cells can be in vitro, ex vivo or in vivo. In some embodiments, a target cell is a stem cell. Stem cells include, but are not limited to, pluripotent stem cells, totipotent stem cells, hematopoietic stem cells, cancer stem cells and embryonic stem cells. In some embodiments, pluripotential cells contemplated herein are not those for propagating a living entity from a zygote or blastomere. The instant invention also contemplates the use of a partially undifferentiated cell for implantation into the eye of a patient in need of treatment, e.g., to regenerate cells of the eye.

Transgenic Animals

Some embodiments of the invention provide a transgenic animal (e.g., nonhuman) expressing a complement factor B analog of the invention. Methods for making a transgenic animal are known in the art. In some embodiment, a transgenic animal (such as a mouse) will also comprise a mutation, deletion or disruption in the Fas gene, e.g., see Macmicking et al. Cell. 81:641-650 (1995).

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Whereas, particular embodiments of the invention have been described herein for purposes of description, it will be appreciated by those skilled in the art that numerous variations of the details may be made without departing from the invention as described in the appended claims.

Example 1. Generation of hfB3 Expression Construct

A plasmid was designed to include the coding sequence for human hfB3 with an IRES-Neo selectable marker (hfB3-IRES-Neo). The plasmid was synthesized by GENEART AG (Regensburg, Germany, plasmid), a fee for service contract organization. An Nhe I restriction site was incorporated into both the 5' and 3' ends of the coding sequence. The hfB3 nucleic acid coding sequence was codon optimized for optimal expression in mammalian cells.

The gene expression plasmid, pCI (Promega, Madison, Wis.), was modified. First, the BGH (Bovine Growth Hormone) polyA was removed from pCI and replaced with a synthetic polyA. Next, the hfB3 coding sequence with a selectable marker (hfB3-IRES-Neo) was cut out by Nhe I from a plasmid and cloned into the Sal I site of the modified pCI as a blunt-end ligation to create an hfB3 expression construct. The plasmid was sequenced in its entirety to confirm the sequence integrity of the construct (SEQ ID NO:5).

Example 2. Generation of hfB3-292S Expression Construct

A further modification was introduced to hfB3 protein. Human wild type factor B protein and hfB3 protein have 23 cysteine amino acids (C), suggesting there is at least one unpaired free cysteine present in the protein. Disulfide bond mapping suggested the free C in biologically active hfB3 is located at the amino acid 292. The C at 292 is highly conserved in factor B protein among different species (Table 1, above). In this Example, this C at 292 is changed to serine (S), generating hfB3-292S.

To create the hfB3-292S expression construct, site-specific mutation was introduced into the hfB3 expression construct (SEQ ID NO:5).

Figure 2:
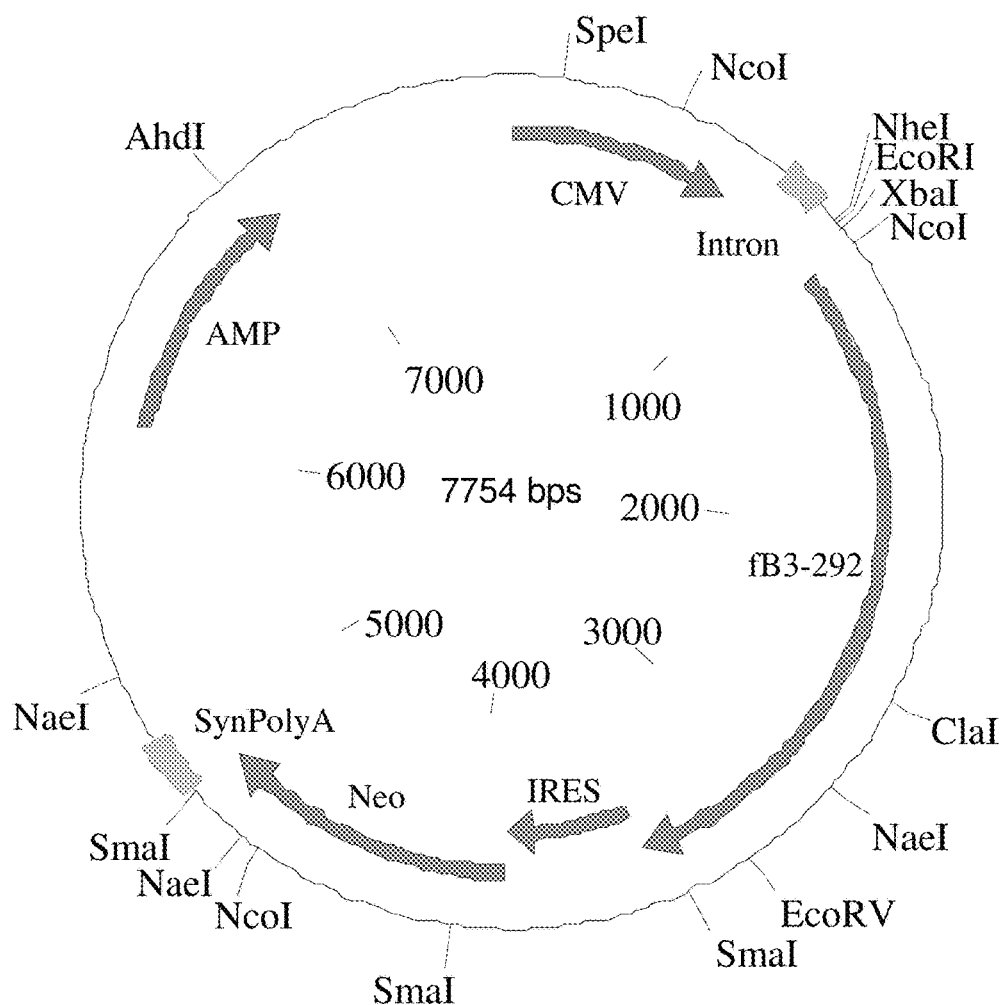

The hfB3 expression construct was used as the template to make the site mutation changing the C at position 292 to S using Stratagene's Site-Directed Mutagenesis Kit according to the manufacture's instructions, creating the hfB3-292S expression construct. Two primers were used: Forward primer 5'-CACCGGCGCCAAGAAG AGCCTGGTCAACCTGATC-3' (SEQ ID NO:6) and Reverse primer 5'-GATCAGGTTGACCAG √GCTCTTCTTGGCGCCGGTG-3' (SEQ ID NO:7). The underlined nucleotides indicate the mutated amino acid from C to S. The hfB3-292S expression cassette includes, from 5' to 3', a CMV promoter, a chimeric intron, a codon optimized coding sequence for hfB3-292S, an IRES-Neo selectable marker, and a synthetic polyA (FIG. 2). The entire construct was sequenced to confirm the mutation and the integrity of the construct (SEQ ID NO:8). The expected amino acid sequence for hfB3-292S is shown in SEQ ID NO:2.

Example 3. Generation of Stable hfB3 and hfB3-292S Expression Cell Lines

Stable cell lines expressing hfB3 or hfB3-292S protein were generated by transfecting 293 FreeStyle cells (Invitrogen, Cat. No. R79007) with the hfB3 or hfB3-292S expression construct. Transfection of plasmid DNA into the 293 FreeStyle cells was mediated by PEI (Polyethylenimine, Sigma, Cat. No. 23966)-based transfection. A PEI solution was prepared in sterile water at a final concentration of 1 mg/mL. The pH was adjusted to 7.0 with 5 N HCl. The solution was sterilized using a 0.22 μm filter. Aliquots of the PEI were stored frozen at −80° C. until use.

The transfection protocol was as follows:

One day prior to transfection, the cells were seeded at $1 \times 10^6$ cells/mL in serum-free 293F Expression Medium (Invitrogen, Cat. No. 12338-018).

The next day, the cells were washed with basal RPMI1640 medium (Invitrogen, Cat. No. 22400-089) supplemented only with HT Supplement (Cat. No. 11067-030, Invitrogen), resuspended in the same medium at $2 \times 10^6$ cells/mL and dispensed into a new 6-well plate with 1 mL in each well.

Stock solutions of DNA and PEI were prepared in sterile 150 mM NaCl as follows: 2.5 μg hfB3 or hfB3-292S expression construct DNA (in 2.5 μL) was diluted into 47.5 μL of 150 mM NaCl and mixed with pipetting (DNA solution). Ten microliters (10 μL) of PEI solution was diluted into 40 μL of 150 mM NaCl, followed by a gentle vortex (PEI solution). The DNA and PEI solutions were incubated at room temperature for 5 minutes. The PEI solution was then added to the DNA solution and the mixture was allowed to incubate at room temperature for an additional 10 minutes and then the DNA/PEI mixture was added to the cells in the 6-well plate and the cells were incubated with agitation (200 RPM) for 5 hours at 37° C. in an incubator with 8% $CO_2$ and 85% humidity. After 5 hours, 1.1 mL of complete 293F Expression Medium (no additives) was added to each of the wells and the incubation was continued for 72 hours.

The cells were then harvested, washed once with the 293F Expression Medium, and placed into fresh 293F Expression Medium containing 300 μg/mL G418 (Teknova). As a negative control, an equal number of un-transfected 293F naive cells were cultured in the same G418-containing medium. The cells were under G418 selection for approximately 3 weeks. By which time, the un-transfected cells in the G418-containing medium were dead. The transfected cells were passed over a FICOL gradient (Sigma) to remove the dead or dying cells from the G418-resistant live population. The G418-resistant live population was further expanded over a period of about 2 weeks, during which the cells were spun down every 2-3 days and resuspended in fresh 293F Expression Medium containing 300 μg/mL G418.

Example 4. Production of hfB3 and hfB3-292S

The G418-resistant hfB3 or hfB3-292S producing cells were seeded at a density of $2 \times 10^6$ cells/mL in the 293F Expression Medium either in 6-well plates with 2 mL culture in each well, in 500 mL spinner flasks with 100 mL culture in each flask, or in 3,000 mL spinner flasks with 1,000 mL culture in each flask. The cells were incubated for 72 hours with shaking at 100 rpm on an orbital shaker in a 37° C. incubator with 8% $CO_2$ and 80% humidity.

The cell culture medium supernatant containing hfB3 protein or hfB3-292S protein was then harvested and centrifuged at 2,000 rpm for 10 minutes to clear cell debris after which the culture medium was filtered through a 0.22 μm filter.

Example 5. Quantitation of hfB3 and hfB3-292S Proteins

An Electrochemiluminescent assay (ECL) was developed for quantitation of hfB3 and hfB3-292S with human wild type factor B as standard. The assay was a sandwich immunoassay based on BioVeris's ECL Technology. Briefly, the ECL assay is formatted as a 96-well plate sandwich, one-step, and no wash assay. The quality control samples (purified factor B from human plasma, Quidel, Cat. No. A408) and test samples were incubated with a master mix reagent containing a biotinylated anti-hfB monoclonal antibody (anti-human factor B monoclonal antibody, R&D Systems, Cat. No. MAB2739), a BV-TAG plus-labeled anti-hfB polyclonal antibody (anti-human factor B polyclonal antibody, R&D Systems, Cat. No. AF2739), and streptavidin-coated paramagnetic beads. The mixture was incubated for 150 minutes. Following the incubation, a stop solution (Borate Buffer, 250 mM, pH9.2 containing 500 mM sodium chloride and 1.6 mg/mL BSA) was added and then the plate was read on MIMR Analyzer. The estimated dynamic range for the assay was 9.0 to 950 ng/mL.

Example 6. Western Blot Analysis for hfB3 and hfB3-292S

Polyacrylamide electrophoresis of hfB3 protein and hfB3-292S protein under denturing but non-reducing conditions (SDS-PAGE) was performed by mixing samples of hfB3 protein or hfB3-292S protein with non-reducing protein sample buffer (Pierce). Human factor B protein purified from plasma (100 ng per sample, Quidel) was used as a positive control. Each gel also contained a well with pre-stained protein molecular weight markers (15 μL/lane) (Invitrogen). The samples and the markers were heated at 95° C. for 5 minutes in non-reducing protein sample buffer. The samples were loaded onto a 7.5% Tris-HCL Precast mini gel (Bio-Rad). The gel was run (10×SDS/Tris/Glycine Running Buffer, Bio-Rad) at 75 V for 15 minutes or until the dye front passed through the stacking gel into the resolving gel. Once the dye front entered the resolving gel, the voltage was increased to 100 V and electrophoresis continued until the dye front ran off the gel.

Western blot analysis was performed by washing and equilibrating the gel in transfer buffer (10× Tris/Glycine Transfer Buffer, Bio-Rad) for 20 minutes while rocking gently. A nitrocellulose membrane (Bio-Rad) and blotting paper were also equilibrated in the transfer buffer. Proteins separated by SDS-PAGE were transferred electrophoretically onto a nitrocellulose using a Trans Blot Semi-Dry Transfer Cell (Bio-Rad) (20V for 45 minutes). Once the transfer was complete, the membrane was blocked with a 1× casein solution (Vector Laboratories) for at least an hour at room temperature with gentle agitation on a rocker. The membrane was probed with a primary antibody (monoclonal antibody against human factor B, R&D Systems, Cat. No. MAB2739) diluted to 1:10,000 in 1× casein solution at room temperature for 1 hour with gentle agitation and washed in 10 mL of 1× casein solution 3 times for 5 minutes each at room temperature with gentle agitation on a rocker. The membrane was incubated with a biotinylated goat anti-mouse IgG (secondary antibody, R&D Systems, Cat. No. BAF007), diluted to 1:20,000 in 1× casein solution, for 1 hour at room temperature with gentle agitation on a rocker and washed in 10 mL of 1× casein solution 3 times for 5 minutes each at room temperature with gentle agitation. The membrane was incubated in Vectastain ABC-AmP reagent (Vector Laboratories) in 20 mL of 1× casein solution for 45 minutes containing 40 μL of Reagent A and 40 μL of Reagent B. The membrane was washed in 10 mL of 1× casein solution 3 times for 5 minutes each at room temperature with gentle agitation.

To acquire the chemiluminescent signal from the Western blots, the membranes were equilibrated in 20 mL of 0.1 M Tris pH 9.5 for 5 minutes without agitation. Excess buffer was removed from the membrane by holding the membrane vertically and touching the edge of the membrane to a Kimwipe. The target side of the membrane was placed facing up in a new container. Duolox Substrate (7 mL, Vector Laboratories) was placed directly onto the target side of the membrane which was incubated for 5 minutes in the dark. Excess Duolox was removed from the membrane by holding the membrane vertically and touching the edge of the membrane to a Kimwipe. The membrane was washed by submerging it in 20 mL of 0.1 M Tris pH 9.5 for 5 minutes with agitation in the dark. Excess buffer was removed from the membrane by holding the membrane vertically and touching the edge of the membrane to a Kimwipe. The membrane was placed in a folded plastic wrap sheet and exposed to Kodak BioMax MS X-ray film in a film cassette for 1 to 5 minutes. The film was placed in Kodak Developer solution (dilute 26 mL of the Developer solution into 92 mL of ddH$_2$O) for 1 minute. The film was removed from the Developer solution and placed in Kodak Fixer solution (dilute 26 mL of the Fixer solution into 92 mL of ddH$_2$O) for 1 minute. Finally, the film was rinsed with tap water and allowed to dry at room temperature.

Figure 3:
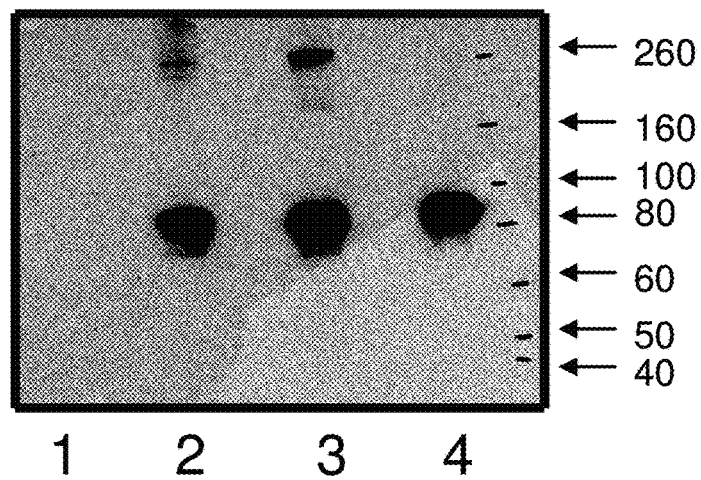

As shown in FIG. 3, G418-resistant hfB3 and hfB3-292S producing cells produced, in the cell culture medium, hfB3 protein (Lane 3) and hfB3-292S protein (Lane 4) at the appropriate size (approximately 100 KDa). These proteins migrated at approximately the same rate as the wild type human factor B purified from human plasma (Lane 2). No visible band was detected in the un-transfected cell culture medium (negative control) indicating the specificity of the monoclonal anti-human factor B antibody (Lane 1). Interestingly, presumed aggregates at approximately 200-260 KDa were readily detected in hfB3 samples (lane 3), while no aggregates were detected in the hfB3-292S samples (lane 4) produced under the same experimental conditions. Aggregates could be caused by misfolded populations of hfB3 in the cell culture medium. When proteins are misfolded, they expose hydrophobic regions that are prone to the formation of aggregates through hydrophobic-hydrophobic interactions. These data suggest that in the hfB3-292S protein preparation, misfolding was either eliminated or significantly reduced as compared to hfB3 protein.

Example 7. Alternative Complement Pathway Hemolytic Activity Assay

Human alternative complement pathway activity can be measured using a hemolytic assay as described in this Example.

One milliliter (1 mL) of rabbit erythrocytes (rRBCs) (Lampire Biological Laboratory, Cat. No. 7246408) suspension was washed with freshly made cold Mg$^{2+}$-EGTA buffer. The erythrocytes were transferred to a 50 mL conical centrifuge tube, 30 mL of the Mg$^{2+}$-EGTA buffer was added and the cells were mixed gently. The rRBCs were pelleted in a Beckman Allegra 6KR centrifuge at 1,200 rpm at 4° C. without brake for 5 minutes and resuspended in the Mg$^{2+}$-EGTA buffer. This wash step was repeated twice. The rRBCs were resuspended in 2 mL of ice-cold Mg$^{2+}$-EGTA buffer and a cell count was obtained using a hemocytometer.

The hemolytic activity reaction mixture was set up in V-bottom shaped 96-well plates placed on ice. To determine if hfB3 protein or hfB3-292S protein can compete with the wild type human factor B protein and inhibit its hemolytic activity, a competition assay was set up in a total volume of 40 μL including 500 ng of wild type human factor B, increasing amounts of hfB3 protein or hfB3-292S protein, and GVB$^{++}$ buffer (Sigma, Cat. No. G6415). Fifty microliters (50 μL) of factor B depleted human serum diluted 25-fold with Mg$^{2+}$-EGTA buffer was added to each well, followed by 10 μL of Mg$^{2+}$-EGTA washed 5×10$^7$ rRBCs. After adding the rRBCs, each sample was gently mixed in the 96 well plate using a multi-channel pipette.

The 96-well plate was placed in a glass tray with a layer of 37° C. water submerging the bottom of the plate. The tray was then placed in a 37° C. water bath with orbital shaking at 110 rpm for 40 minutes. After incubation, the plate was placed on ice, 150 pt of ice-cold 0.9% saline was added to each well, and each reaction gently mixed by pipetting to stop the reaction. The 96-well plate was centrifuged at 2,000 rpm in an Eppendorf 5810R centrifuge for 5 minutes (min) at 4° C. without brake to pellet the rRBC at the bottom of the plate. The supernatant (180 μL) was removed from each well without disturbing the pellet and transferred to the corresponding well of a new 96-well plate. The absorbance of each sample was measured at 405 nm in a microplate reader.

Example 8. Biological Activity of hfB3 and hfB3-292S

Figure 4:
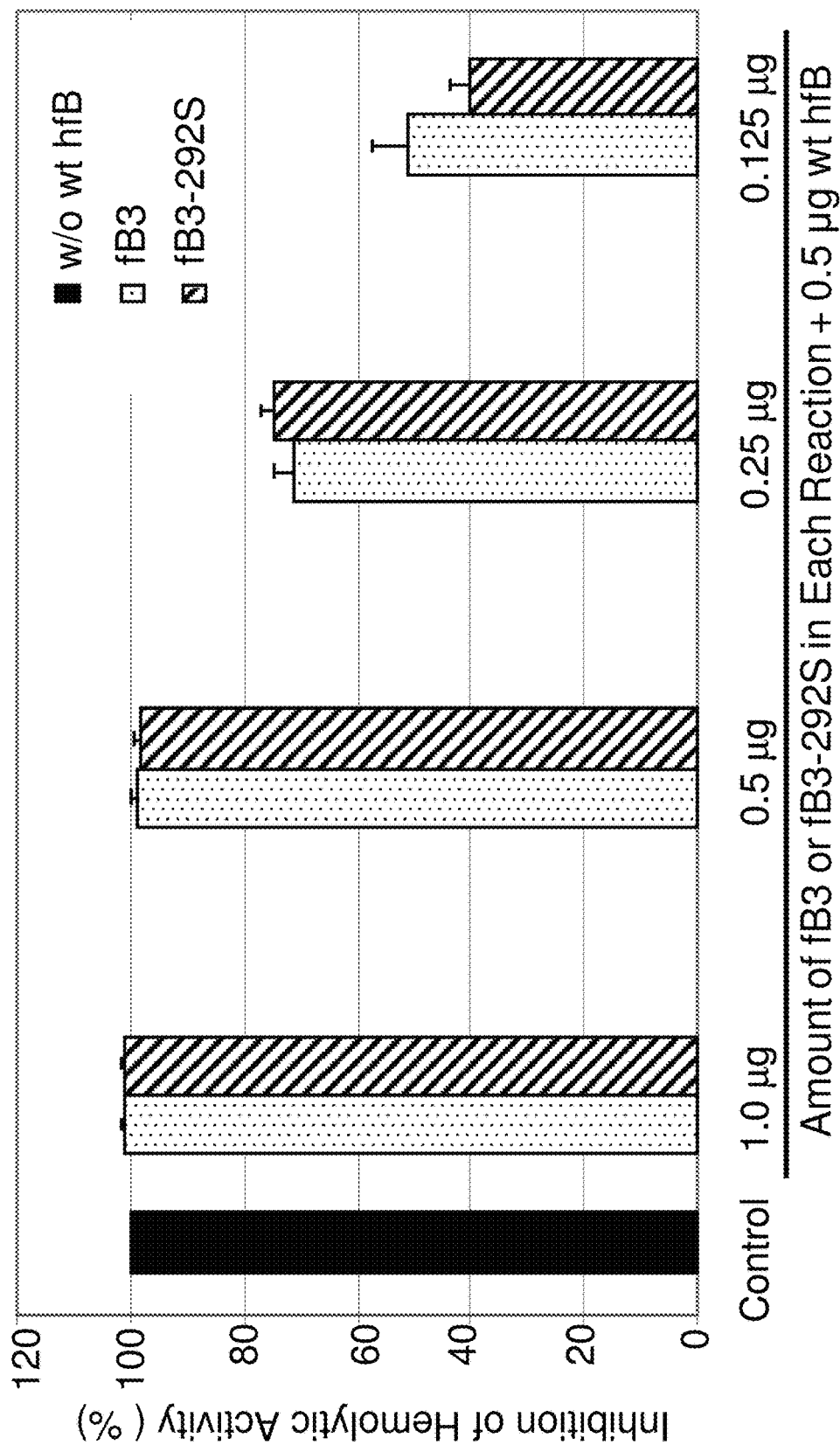

The biological activity of hfB3 protein and hfB3-292S protein was examined by measuring the alternative complement pathway mediated hemolysis of rRBCs. The assay described in Example 7 was used to test the potency of hfB3 protein or hfB3-292S protein in inhibiting the human alternative complement pathway. Each reaction was performed in triplicate. As shown in FIG. 4, the raw cell culture medium from hfB3-292S protein and hfB3 protein producing cells efficiently inhibited/reduced the alternative complement pathway activity in a dose-dependent manner Although not wishing to be bound by theory, hfB3 and hfB3-292S protein may be inhibiting alternative complement pathway activity by competing against the wild type factor B protein and/or by sequestering C3b and/or complement factor D.

Example 9. Purification of hfB3 and hfB3-292S Proteins

Cell culture medium from a human 293 FreeStyle cell line transfected and stably expressing and secreting hfB3 protein or hfB3-292S protein was used as the starting material for purification of hfB3 protein or hfB3-292S protein. Soluble secreted hfB3 or hfB3-292S protein was purified from the cell culture supernatant by a combination of anion exchange (AEX), hydrophobic interaction (HIC) and size exclusion chromatography (SEC) for capturing, intermediate purification and polishing steps, respectively, using a GE AKTA Purifier. Two purification schemes are described below. These two schemes differ in that one uses one HIC chromatography step and the other uses two HIC chromatography steps.

The cell culture supernatant containing hfB3 protein was diluted with distilled water at 4:1 volume ratio of culture supernatant/water to lower the conductivity to ~8 Milli Siemens per centimeter (mS/cm) and adjusted to pH 7.5 with 50 mM phosphate buffer. This material was loaded directly onto a pre-packed ion exchange column (POROS HQ 50, ABI) on an AKTA purifier using a P-960 pump at a flow rate of 30 mL per minute. The column was previously equilibrated with buffer A (50 mM phosphate buffer (PB), pH7.5, conductivity ~8 mS/cm), at a linear flow rate of 600 mL/hr (~1 Column Volume/min, CV/min). The effluent was monitored by UV detection at 280 nm. After washing away unbound material, retained material was eluted with a non-linear gradient of buffer A and buffer B (50 mM PB and 1 M NaCl, pH 7.5) to sequentially raise the conductivity of the mobile phase stepwise from 8 mS/cm (0% of buffer B for 2 CV), to 33 mS/cm (25% of buffer B for 8 CV) and finally to 105 mS/cm (100% of buffer B for 5 CV).

To further facilitate removal of host protein contaminants, an intermediate, hydrophobic interaction (HIC) chromatography step was introduced, which purifies and separates proteins based on differences in their surface hydrophobicity. The major fractions (from the AEX chromatography step) containing hfB3 protein were pooled and adjusted to contain approximately 1.4 M ammonium sulfate and 47 mM phosphate buffer, pH 7.5 (conductivity 216 mS/cm) (1.0 M ammonium sulfate and 33.7 mM phosphate buffer, pH 7.5, conductivity 169 mS/cm for hfB3-292S) by adding buffer C (1.5 M ammonium sulfate and 50 mM phosphate buffer, pH 7.5) to the sample at approximately 30:1 volume ratio of the ammonium sulfate/phosphate buffer vs. the sample. The pooled sample was filtered through a 0.2 µm filter and applied to a hydrophobic interaction column (HiTrap Phenyl HP, GE Healthcare) pre-equilibrated with 1.5 M ammonium sulfate and 50 mM Phosphate buffer, pH 7.5 (buffer C) (1.0 M ammonium sulfate and 33.7 mM phosphate buffer for hfB$_3$-292S) at the flow rate of 300 mL/hr (1 CV/min). The retained material was eluted by decreasing the ammonium sulfate concentration in a non-linear fashion.

Alternatively, the intermediate HIC chromatography step can be replaced with a two-steps HIC chromatography, e.g., to make the purification process easier to scale-up. In this two-step HIC purification process, the majority of host cell proteins were separated from fB3 or fB3-292S by the first step HIC chromatography, HIC negative selection, by binding to HIC column (HiTrap Phenyl HP, GE Healthcare) at low salt condition (0.75 M ammonium sulfate and 25 mM phosphate buffer, pH 7.5 for fB3 and 0.6 M ammonium sulfate and 20 mM phosphate buffer, pH 7.5, conductivity 100 mS/cm for hfB3-292S). The flow-thru fraction from the HIC negative selection step containing hfB3 or fB3-292S protein was then re-adjusted to contain approximately 1.5 M ammonium sulfate and 50 mM phosphate buffer, pH 7.5 (conductivity 216 mS/cm) for fB3 or 1.0 M ammonium sulfate and 33.7 mM phosphate buffer, pH 7.5, (conductivity 169 mS/cm) for hfB3-292S. For the second step HIC chromatography, the sample was filtered through a 0.2 µm filter and applied to a hydrophobic interaction column (HiTrap Phenyl HP, GE Healthcare) pre-equilibrated with 1.5 M ammonium sulfate and 50 mM Phosphate buffer, pH 7.5 for fB3 and 1.0 M ammonium sulfate and 33.7 mM phosphate buffer for hfB$_3$-292S at the flow rate of 300 mL/hr (1 CV/min). The retained material was eluted by decreasing the ammonium sulfate concentration in a non-linear fashion to further separate fB3 or fB3-292S protein from the remaining host cell proteins.

The fractions containing biologically active hfB3 protein from the HIC chromatography step were pooled and concentrated with a centrifugal filter device (Millipore, Amicon Ultra, Cat. No. 901024, 10,000 MW Cut-off). The concentrated sample was subjected to size exclusion chromatography on a Sephacryl S300 26/60 HR column (maximum loading volume: 3% of CV, ~10 mL), equilibrated in PBS buffer (4 mM phosphate, 150 mM NaCl, pH 7.4, (GIBCO)). The elution of hfB3 protein was performed at a constant linear flow rate of 60 cm/hr using PBS, monitoring the effluent by UV detection at 280 nm. The purified hfB3 protein was stored at −80° C. in aliquots.

Figures 5A, 5B:
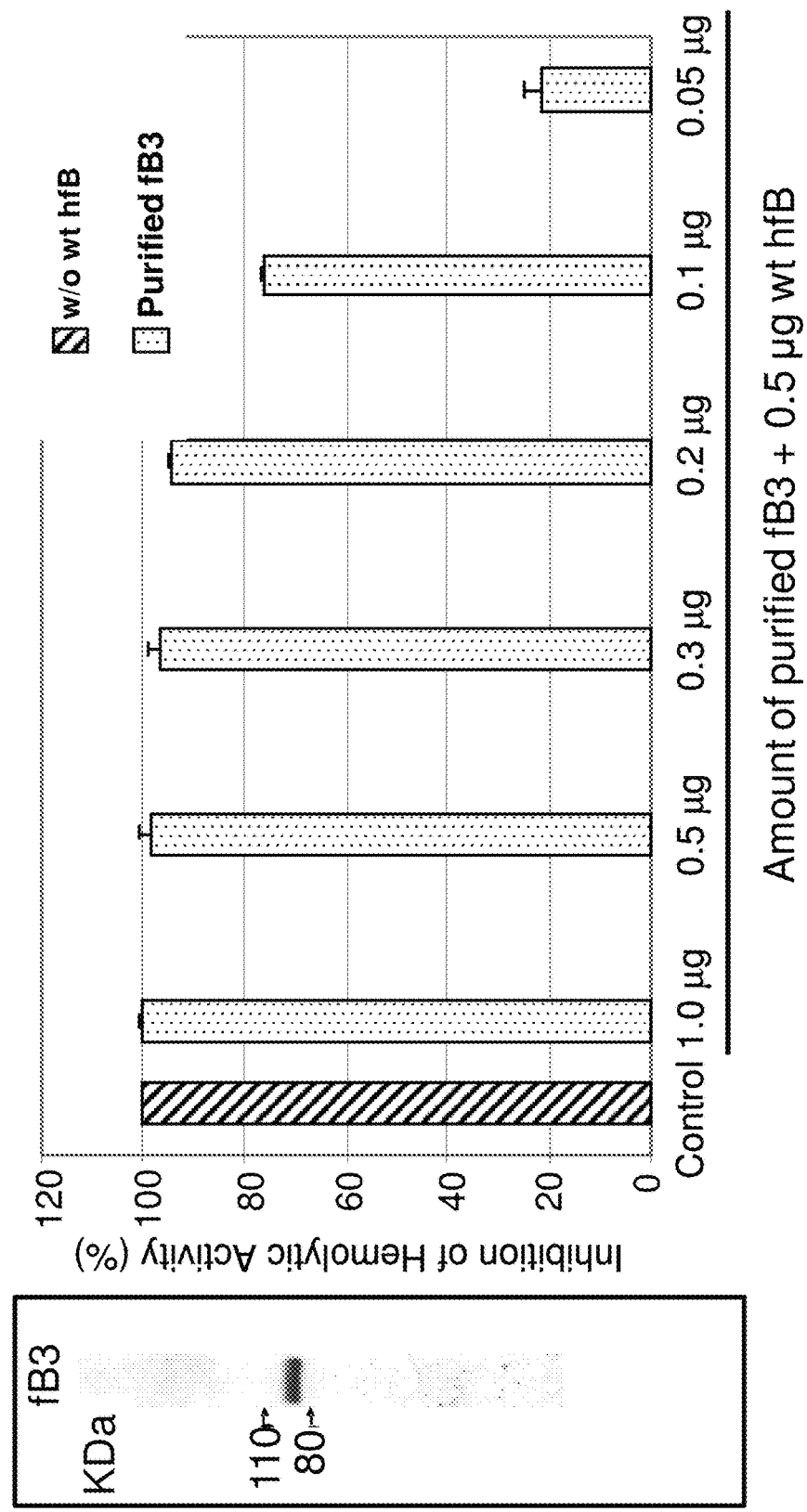

This procedure permitted almost complete separation of hfB3 protein from other contaminants. The purity of hfB3 protein after the three step chromatography process was quite high, as indicated by the fact that SDS-PAGE silver staining analysis of 0.2 µg of purified hfB3 protein only produced a single sharp band (FIG. 5, left panel). When hfB3 protein purified by the above three step chromatography process was subjected to a competition assay against human wild-type factor B in a hemolytic assay, it suppressed hemolytic activity of the human alternative complement pathway, demonstrating that the purified hfB3 protein was biologically active (FIG. 5, right panel). Surprisingly, two populations of hfB3 were detected by HIC, one was biologically active (designated as Peak I or active population) and the other had a much reduced biological activity (designated as Peak II or less active population) (FIG. 6). These two forms were readily detected by reverse-phase HPLC (RP-HPLC) in the un-processed cell culture medium of stable hfB3 protein producing cells (FIGS. 7A and 7B).

Figure 7A:
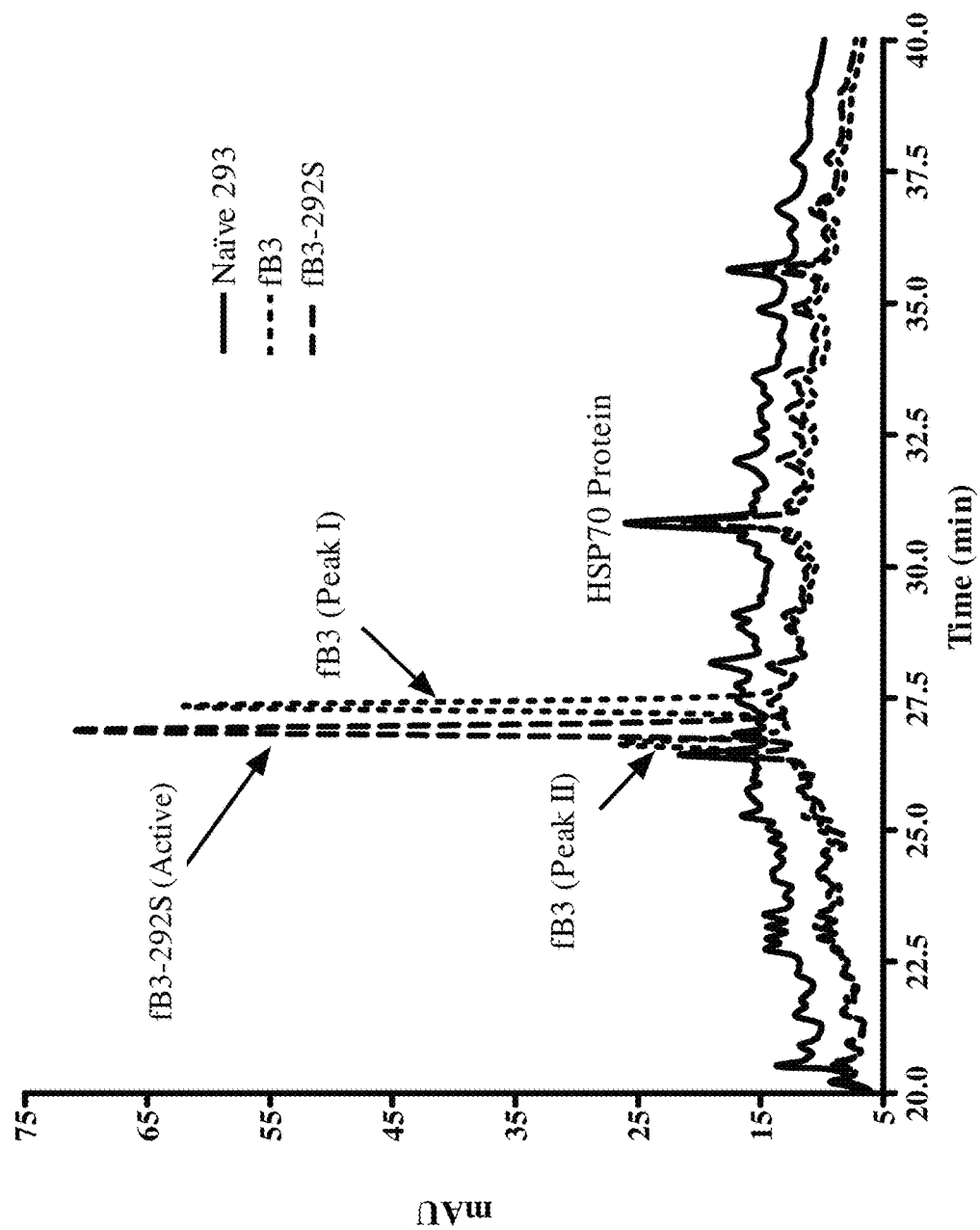
FIG. 7B shows an enlarged region of the chromatogram shown in FIG. 7A focusing on the region (25-29 minutes) containing the Peaks I and II of hfB3 protein and the peak containing hfB3-292S protein.
Figure 7B:
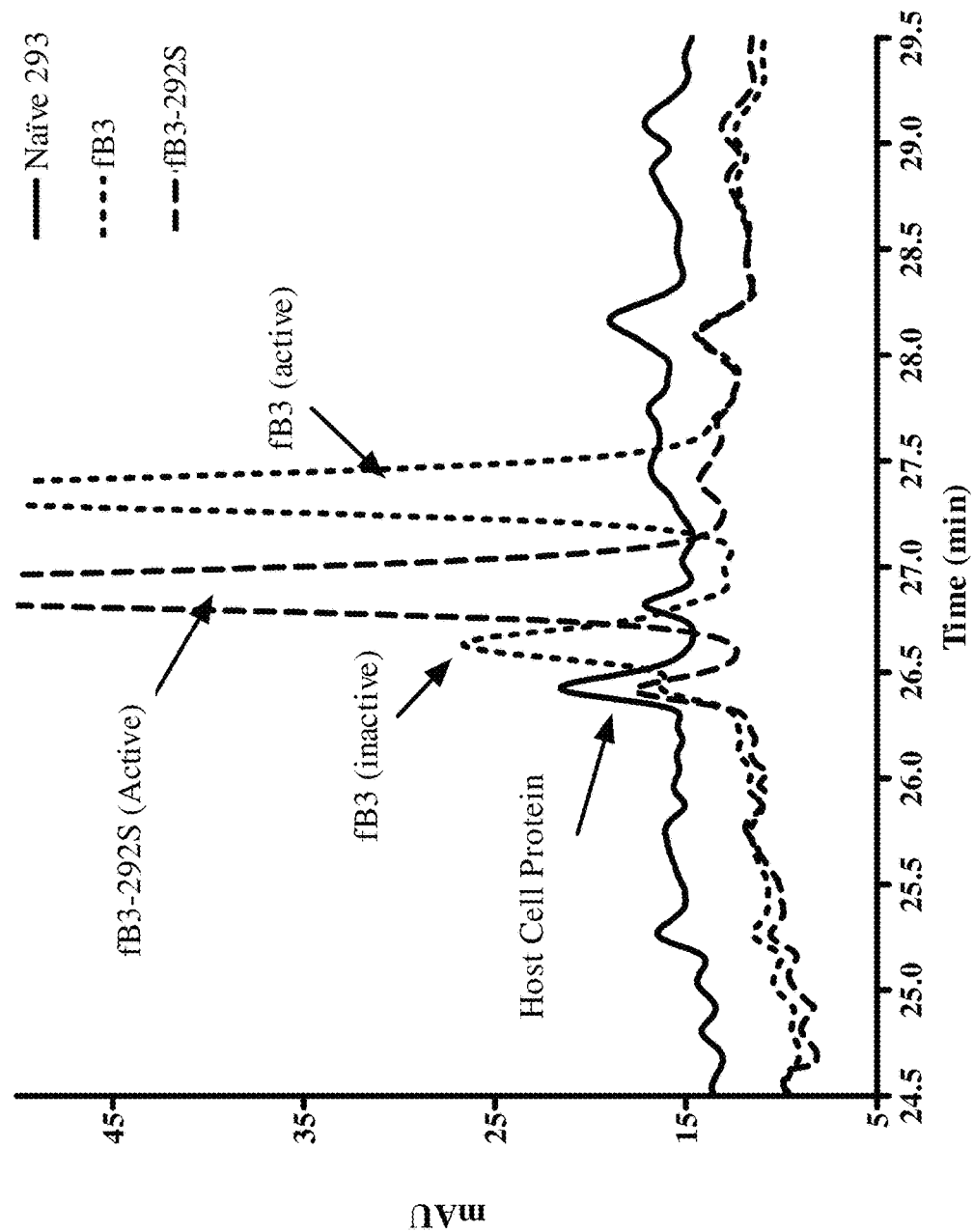

Example 10. hfB3-292S Protein Producing Cell Line does not Produce the Peak II Population The raw hfB3-292S protein cell culture medium containing a complement factor B analog with the free cysteine substituted with serine at the position 292 was subjected to RP-HPLC analysis with raw naïve 293 FreeStyle cell culture medium as a negative control and raw hfB3 protein cell culture medium as a positive control (FIGS. 7A & 7B). The hfB3-292S protein cell culture medium did not produce any detectable Peak II population, whereas analysis of hfB3 protein cell culture medium showed that 35% of hfB3 was in the less active, Peak II, population. (FIGS. 7A & B.)

Example 11. Generation and Characterization of hfB4 Expression Construct and hfB4 Protein hfB4 protein was designed to change the aspartic acid, at amino acid 740 in hfB3, to an asparagine. This change is thought to attenuate or inhibit the function of the serine protease function of this complement factor B protein analog.

To create the hfB4 expression construct, site-specific mutation was introduced into the hfB3 expression construct. The hfB3 expression construct (SEQ ID NO:5) described in Example 1 was used as a template to make a mutation changing the aspartic acid (D) at position 740 in SEQ ID NO:4 to asparagine (N) using Stratagene's Site-Directed Mutagenesis Kit (Stratagene, Santa Clara, Calif.) according to the manufacture's instructions, creating the hfB4 expression construct. Two primers were used: Forward primer 5'-GTCCCCGCCCACGCCCGG AACTTCCACATCAACCTGTTCC-3' (SEQ ID NO:15) and Reverse primer 5'-GGAACAGGTTGATGTGGAA GTTCCGGGCGTGGGCGGGGAC-3' (SEQ ID NO:16). The underlined nucleotides indicate the nucleotide change that results in the amino acid change from D to N. This hfB4 expression construct includes, from 5' to 3', a CMV promoter, a chimeric intron, a codon optimized coding sequence for hfB4, an IRES-Neo selectable marker, and a synthetic polyA. The entire construct was sequenced to confirm the mutation and the integrity of the construct. The expected amino acid sequence for hfB4 is shown in SEQ ID NO:17. The only difference between the amino acid sequence of hfB3 and hfB4 is the D740N change.

A stable cell line that expresses hfB4 protein was generated by PEI-mediated transfection and drug selection of 293 cells as described in Example 3. The concentration of hfB4 protein in the cell culture medium of the selected cell population was measured by ECL as described in Example 5.

Biological activity of hfB4 protein, purified as described in Example 9 using the one HIC chromatography step method, was examined by hemolytic activity assay as described in Example 7. Table 2 shows the inhibition of human alternative complement pathway hemolytic activity by cell culture medium containing hfB4 protein. Relative hemolytic activity was scored by hemoglobin released after hemolysis of rRBC by human alternative complement pathway activity. As shown in Table 2, hfB4 protein efficiently inhibited the alternative complement pathway activity.

TABLE 2 hfB4 inhibition of human alternative complement pathway hemolytic activity

| | Control w/o wt | Competed with 0.5 ug wt hfB | | | |
|---|---|---|---|---|---|
| hfB4 | 0.0 ug | 1.0 ug | 0.5 ug | 0.25 ug | 0.125 ug |
| % Inhibition | 100 ± 0.0 | 99.3 ± 1.5 | 100.3 ± 0.0 | 100.1 ± 0.3 | 96.1 ± 0.8 |

Example 12. Generation and Characterization of an hfB3-Fc Expression Construct and an hfB3-Fc Protein hfB3-Fc is a fusion protein between hfB3 and an IgG Fc. Specifically, the full length of the hfB3 protein was fused with a human IgG4 Fc.

To create an hfB3-Fc expression construct, a PCR product was amplified from the hfB3 expression construct (SEQ ID NO:5) described in Example 1 using two primers: the forward primer 5'-GCGCACCGGTGCTAGCGAATTCG-GCGACAAGAAGGGCAGCTGCGA-3' (SEQ ID NO:19); and the reverse primer 5'-GCGCAGATCTCAGGAAGC-CCAGGTCCTCAT-3' (SEQ ID NO:20). The 377 bp PCR product containing the coding region for the C-terminus of hfB3-Fc was then digested with Age I and Bgl II and ligated into pFUSE-hIgG4Fc (Invivogen, Cat. Code: pfuse-hg4fcl) which was previously digested with Age I and Bgl II, creating the plasmid phfB3Cterm-Fc. The hfB3 expression construct (SEQ ID NO:5, described in Example 1) was digested with EcoR I and EcoR V. The EcoR I/EcoR V fragment containing the N-terminus of hfB3 was ligated into phfB3Cterm-Fc which was previously digested with EcoR I and EcoR V, creating phfB3-Fc. The phfB3-Fc plasmid was digested with Nhe I and the fragment containing the hfB3 and Fc coding sequences was ligated into the modified pCI construct with IRES-Neo described in Example 1, creating the hfB3-Fc expression construct (SEQ ID NO:18). This hfB3-Fc expression construct includes, from 5' to 3', a CMV promoter, a chimeric intron, a coding sequence for hfB3-Fc, an IRES-Neo selectable marker, and a synthetic polyA. The entire construct was sequenced to confirm the integrity of the construct (SEQ ID NO:18). SEQ ID NO:21 is the amino acid sequence of the hfB3-Fc protein.

Figure 8:
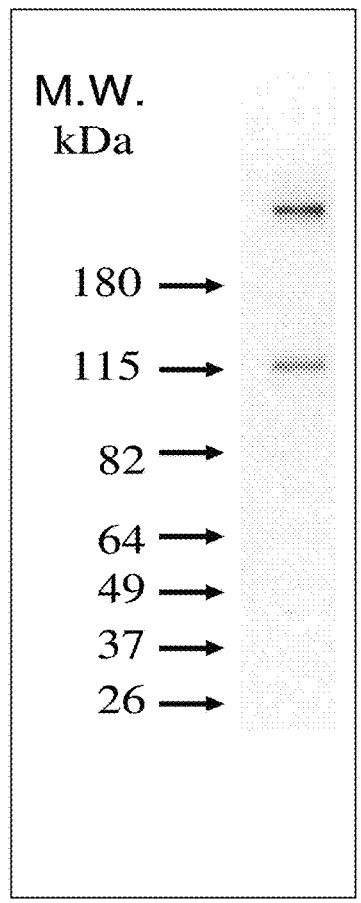
FIG. 8 shows analysis of hfB3-Fc protein expression by subjecting 2 μl of cell culture supernatant containing hfB3-Fc protein to a non-reducing SDS-PAGE and Western blot analysis. (See Example 12) Two bands of hfB3-Fc protein were detected with molecular weight markers in KDa indicated on the left.

A stable cell line that expresses hfB3-Fc protein was generated by PEI-mediated transfection and drug selection of 293 cells as described in Example 3. The drug selected cells were cultured at $2\times10^6$ cells/mL for 72 hours. Then hfB3-Fc protein expression was examined by subjecting 2 µl of the cell culture supernatant to a non-reducing SDS-PAGE and Western blot analysis. As shown in FIG. 8, two bands of hfB3-Fc protein were detected by a goat anti-factor B specific antibody (R&D Systems, Cat. No. AF2739). The molecular weight markers in KDa are indicated on the left. Not wishing to be bound by theory, these two bands of hfB3-Fc protein might represent monomers and dimers of the protein. Biological activity of hfB3-Fc protein (in cell culture supernatant) was examined by a hemolytic activity assay as described in Example 7. As shown in Table 3, hfB3-Fc protein inhibited the alternative complement pathway activity.

TABLE 3 hfB3-Fc inhibition of human alternative complement pathway hemolytic activity

| | Control w/o wt | compete with 0.5 ug wt hfB | |
|---|---|---|---|
| Sup. of hfB3-Fc | 0 | 35 ul | 20 uL |
| % inhibition | 100 ± 0.0 | 100.2 ± 0.8 | 92.6 ± 8.5 |

Example 13. Effect of Repeated Freeze/Thaw on hfB3-292S Complement Inhibition hfB3-292S protein was purified as described in Example 9 using the one HIC chromatography step method. Purified hfB3-292S protein in PBS, removed from a −80° C. freezer and thawed at room temperature, was counted as the first freeze and thaw cycle. After this thaw, the hfB3-292S protein concentration was adjusted to 2 mg/mL with PBS and one aliquot of hfB3-292S was sampled and saved on ice as the first freeze- and thaw sample. The tube of hfB3-292S protein was then frozen by sitting the tube in a methanol/dry ice bath for 20 minutes and then thawing at room temperature till completely thawed (the second freeze and thaw cycle). One aliquot of the sample was sampled and set aside before repeating the next freeze and thaw cycle. The biological activity of samples from each cycle of freeze and thaw (total 7 times) were analyzed by measuring their ability to compete with wild type human factor B in the alternative complement pathway mediated hemolytic assay as described in Example 7. Each reaction contained a fixed amount of wild type human factor B (0.5 µg) with increasing amounts of hfB3-292S. The results in Table 4 represent the percentage of inhibition in the hemolytic assay.

These results demonstrate that hfB3-292S protein can still effectively inhibit alternative pathway mediated hemolysis even after seven cycles of freeze and thaw (Table 4). A similar level of hemolysis inhibition was observed through out all samples showing that repeated freeze and thaw (up to 7 times) did not affect the hfB3-292S protein's ability to inhibit complement mediated hemolysis.

TABLE 4 hfB3-292S After Freeze/Thaw cycles

| Amount of hfB3-292S in Each Reaction | Freeze Thaw Cycles | | | | | | |
|---|---|---|---|---|---|---|---|
| | 1 | 2 | 3 | 4 | 5 | 6 | 7 |
| 1.0 µg | 103.6 +/− 0.4 | 103.9 +/− 1.3 | 103.3 +/− 0.1 | 100.6 +/− 0.5 | 101.3 +/− 1.4 | 102.5 +/− 1.2 | 101.2 +/− 0.4 |
| 0.5 µg | 104.5 +/− 0.6 | 102.7 +/− 1.0 | 102.6 +/− 0.5 | 101.5 +/− 1.5 | 102.9 +/− 2.1 | 102.4 +/− 0.9 | 100.0 +/− 1.8 |
| 0.25 µg | 98.8 +/− 1.0 | 99.8 +/− 2.0 | 99.5 +/− 0.6 | 97.9 +/− 1.5 | 97.1 +/− 0.8 | 97.8 +/− 0.5 | 95.5 +/− 0.6 |
| 0.125 µg | 80.7 +/− 2.2 | 88.3 +/− 1.3 | 84.2 +/− 1.1 | 85.6 +/− 0.8 | 77.6 +/− 3.7 | 80.0 +/− 1.4 | 74.8 +/− 2.3 |

Example 14. Greater Thermostability of hfB3-292S Protein than hfB3 Protein hfB3 and hfB3-292S proteins were purified as described in Example 9 using the one HIC chromatography step method. Purified hfB3 and hfB3-292S protein, both in PBS, were removed from −80° C. Protein concentration was re-adjusted to 2 mg/mL in PBS (pH 7.4). hfB3 and hfB3-292S proteins were equally aliquoted into three 0.6 mL eppendorf tubes (40 µL per tube) and then stored at 4° C., −80° C. and 37° C. conditions for 7 days. The biological activity (ability to inhibit complement mediated hemolysis) of each of the stored samples was analyzed by measuring their ability to inhibit alternative complement pathway mediated hemolysis as described in Example 7. The results of this hemolytic assay showed that storage at 4° C. or −80° C. over 7 days did not affect the ability of either hfB3 or hfB3-292S to inhibit alternative complement pathway mediated hemolysis. However, hfB3 protein stored at 37° C. for 7 days lost essentially all of its biological activity in all four samples tested. Remarkably, hfB3-292S stored at 37° C. for 7 days preserved its biological activity well and still could compete with wild-type human factor B effectively (Table 5). The results in the Table 5 represent the percentage of inhibition of human alternative complement activity (with standard deviation) by either hfB3 or hfB3-292S. These results indicated that hfB3-292S protein has greater thermostability than hfB3 protein at 37° C.

TABLE 5

Thermostability of hfB3 and hfB3-292S

| Sample | Treatment | Amount of Purified hfB3 in Each Reaction + 0.5 µg Wild Type Human Factor B | | | |
|---|---|---|---|---|---|
| | | 1.0 µg | 0.5 µg | 0.25 µg | 0.125 µg |
| hfB3 | 4° C. for 7 days | 99.6 ± 0.2 | 99.1 ± 0.9 | 98.2 ± 0.6 | 88.7 ± 0.7 |
| | −80° C. for 7 days | 99.8 ± 1.2 | 98.2 ± 1.8 | 97.2 ± 1.1 | 89.2 ± 5.8 |
| | 37° C. for 7 days | 0.0 ± 5.5 | 0.0 ± 3.7 | 0.3 ± 5.8 | 4.1 ± 6.4 |

| | | Amount of Purified hfB3-292S in Each Reaction + 0.5 µg Wild Type Human Factor B | | | |
|---|---|---|---|---|---|
| | | 1.0 µg | 0.5 µg | 0.25 µg | 0.125 µg |
| hfB3-292S | 4° C. for 7 days | 98.4 ± 0.6 | 98.4 ± 0.9 | 97.8 ± 0.3 | 83.1 ± 3.0 |
| | −80° C. for 7 days | 99.0 ± 0.3 | 98.4 ± 0.7 | 96.8 ± 0.8 | 81.7 ± 2.1 |
| | 37° C. for 7 days | 98.2 ± 0.4 | 94.6 ± 0.9 | 78.2 ± 2.9 | 48.0 ± 1.3 |

Example 15. Protein Melting Point Determination of Human Factor B, fB3, and fB3-292S Proteins Protein melting temperature (Tm) is a measure of the thermal stability of a protein and changes in the amino acid sequence of a protein may affect, among other things, the protein's thermal stability. Human factor B protein (hfB) contains twenty-three cysteine residues, twenty-two of which occur as disulfide bond pairs (cystine) and one of which, C292, is present in an un-paired free sulfhydrile form.

The melting temperature profiles of hfB3 protein (K258A, R259A, K260A, D279G, N285D) and hfB3-292S protein (the single unpaired cysteine residue of hfB3 protein was modified to serine) were compared to that of hfB protein by incubating each protein in the presence of 1-anilinonaptha-lene-8-sulfonic acid (ANS) and measuring the increase in fluorescence of ANS at 460 nm. ANS binds to protein hydrophobic regions (Stryer, J. Molecular Biology (1965) 13:482-495) and has been used to investigate the effect of temperature on the surface hydrophobicity of hfB protein (Takada, et. al., Complement (1985) 2:193-203). Samples containing hfB protein (35 hfB3 protein (50 µg) and hfB3-292S protein (39 µg) were prepared in 100 µL of PBS (137 mM NaCl, 2.7 mM KCl, 10 mM phosphate, pH 7.4) buffer containing 10 mM ANS (Invitrogen, Catalog # A-47). Samples of each protein (in triplicate) were incubated in closed polypropylene tubes for thirty minutes at 21° C., 30° C., 37° C., 44° C., 47° C., 50° C., 55° C., 60° C., and 65° C. The samples were transferred to a clear 96-well microplate (Costar, Catalog#3635) and the fluorescence was measured in a Perceptive Biosystems Cytofluor 4000 microplate spectrofluorometer (excitation=60/40 nm, emission=460/40 nm). The results were analyzed using a non-linear 4 µL curve fit. The Tm values (average of the results from two experiments) for wild type hfB protein, hfB3 protein and hfB3-292S protein were determined to be 46.4° C., 45.1° C., and 47.0° C., respectively. The five amino acid changes made in hfB3 protein with respect to wild type hfB protein (K258A, R259A, K260A, D279G, N285D) resulted in a ΔTm=−1.3° C., indicating that hfB3 protein was less thermally stable compared to a corresponding wild type hfB protein. However, the Tm of hfB3-292S protein (47.0° C.)

resulted in a ΔTm=+1.9° C. with respect to hfB3 protein and indicated that hfB3-292S protein was at least as thermally stable as wild type hfB protein (46.4° C.).

Therefore, contrary to the results of Culajay, et. al. (Biochemistry (2000) 39:7153-7158) which showed that substitution of a cysteine residue with serine in human fibroblast growth factor (FGF-1) protein (C83S or C117S) decreased the Tm by 13° C. and 2° C., respectively, the serine substitution of hfB3 at amino acid C292 resulted in hfB3-292S being more thermal stable than hfB3.

Example 16. hfB3-292S Protein Prevents Joint Inflammation and Damage in a Mouse Rheumatoid Arthritis Model Collagen antibody-induced arthritis (CAIA) is an aggressive mouse model for rheumatoid arthritis (Terato K et al., J. Immunol. (1992) 148(7):2103-8; Terato K et al., Autoimmunity (1995) 22(3):137-47). In this model, a collagen antibody cocktail containing 4 monoclonal antibodies against collagen (Chondrex, Inc., Catalogue Number: 10010) with LPS boost was used to induce arthritis in six-week-old DBA/1J male wild type mice (Jackson Laboratory).

Forty mice were divided into three groups. Group 1 had 10 mice serving as a vehicle control group where 100 μL PBS (phosphate buffered saline, pH 7.4) was injected into the tail vein on day 0, a booster injection of 25 μg LPS (List Biological Lab, Campbell, Calif., Catalogue Number: 421) per mouse was administrated intraperitoneal (LPS was in PBS at a concentration 500 μg/mL) on day 3, and 100 μL of PBS via the tail vein again on days 3, 5, 7, and 9. Group 2 had 15 mice that were injected with the collagen antibody cocktail (0.25 mg in 100 μL PBS per mouse) via tail vein on day 0, received a booster injection of 25 μg LPS on day 3, and were administered 100 μL PBS via the tail vein on days 3, 5, 7, and 9. Group 3 had 15 mice that were injected with 0.25 mg of the collagen antibody cocktail and 1 mg of hfB3-292S protein, both together in 100 μL PBS per mouse via the tail vein on day 0, administered a booster injection of 25 μg LPS on day 3, and administered 1 mg of hfB3-292S protein in 100 μL PBS via tail vein on days 3, 5, 7, and 9.

Mice were examined every day. Each mouse weight was recorded when joint measurement took place. Forepaws and hind limb joints were measured using calipers for both width and thickness on days −1, 4, 6, 9 and 11. The measuring sequence was left front limb, left hind limb, right hind limb and right front limb. On day 11, all animals were sacrificed and all the limbs (left front limb, right front limb, left hind limb and right hind limb) were collected and stored in individually-labeled plastic cassettes. Each cassette was placed in a histology container box containing 10% neutral buffered formalin solution.

These mouse limbs were subjected to paraffin sectioning and H&E staining to examine the pathogenesis in the joints. Specifically, following fixation, each limb from each mouse was transferred to a plastic cassette separately. The limbs were rinsed with running water in a beaker for 30 minutes (min) at room temperature (RT) to remove fixative solution. Then each cassette was transferred to a beaker containing decalcified solution (Thermo Scientific, Catalogue number 8340) by immersion of the cassette into the solution. Front limbs were decalcified for 8 hours and hind limbs were decalcified for 9 hours. After 8 hours or 9 hours, the limbs were again rinsed with running water for 30 mm at RT to remove decalcified solution. After decalcification, limbs were stored in 70% ethanol overnight (O/N) for the next dehydration step. Limbs were dehydrated by sequentially immersing into: 75% ethanol (made from 100% ethanol) for two times; 85% ethanol for two times, 95% ethanol for two times and 100% ethanol for two times, each time for 15 min at RT with shaking. Next, the limbs were immersed in a 1:1 mixture of 100% ethanol and cedar wood oil (Fisher, Catalogue Number: 040-1) for 15 min at RT with shaking, and repeated two more times for a total of three times. The limbs were then immersed in 100% cedar wood oil and incubated at 40° C. for 5 hrs. Following the 5 hour incubation, limbs were immersed in a 1:1 mixture of cedar wood oil and methyl salicylate (ACROS, Catalogue number 119-36-8) for 60 mm at RT. The limbs were then immersed in another 1:1 mixture of cedar wood oil and methyl salicylate O/N at RT. Following the O/N incubation, limbs were immersed in 100% methyl salicylate for 40 mm at RT, repeated one more time (a total of two times). Finally, limbs were embedded in paraffin that was prepared by incubation at 60° C. for 7 hrs.

Paraffin sections of the mouse limbs were prepared using a microtome and cut to a 7 μm thickness. The sections were incubated on a 40° C. water bath and transferred to a Superfrost Plus microscope slide. The slides were dried O/N at RT, and further dried by incubation O/N on a slide warmer. The slides were kept at RT until staining.

Mounted paraffin sections of the mouse limb were subjected to H&E staining. The sections were de-paraffinized and rehydrated by immersion into xylene for 3 mm repeated 2 times for a total of 3 times. The excess xylene was then blotted, and sections were immersed in 100% ethanol for 3 min, for a total of 3 times, then 95% ethanol for 3 min, once, 80% ethanol for 3 min, once, and deionized water for 5 min, once. All incubations were at RT. For the hematoxylin staining, slides were immersed in hematoxylin for 4 min, one time, and rinsed with deionized water. The slides were immersed in tap water for 5 min one time to allow the stain to develop. The slides were dipped quickly, 8-12 times, into acid ethanol (200 ml 70% ethanol plus 150 μL concentrated HCL) to destain the sections. The slides were then rinsed twice for 1 mm in tap water, and then once for 2 mm in deionized water. The excess water was blotted from the slides prior to eosin staining.

For the eosin staining, slides were immersed in eosin once for 20 seconds. Slides were then dehydrated by immersion into 95% ethanol 3 times for 5 min. Slides were incubated in 100% ethanol 3 times for 5 min. The excess ethanol was blotted, and the slides were incubated in xylene three times for 15 min. Coverslips were adhered to the slides using the xylene-based Permount (EMS, Catalogue number 17986-01) by placing a drop of Permount on the slide using a glass rod being careful not to form bubbles. The coverslip was then angled onto the slide and dropped gently onto the slide. The Permount was allowed to spread beneath the coverslip covering the entire section. The slides were dried O/N at RT in a chemical hood.

As shown in FIG. 10, the group injected with collagen antibody cocktail in the absence of hfB3-292S (Group 2) induced severe front paw swelling. Mice injected with the antibody cocktail, but were treated with hfB3-292S protein (Group 3) showed a 65% reduction in the size of the paw (p<0.0003) (FIG. 10). These results demonstrate a significant inhibitory effect of joint arthritis in this model by hfB3-292S. At 250 μg collagen antibody cocktail dosage per mouse for the induction of CAIA, the hind limbs of the mice did not show obvious swelling. No significant adverse effect for hfB3-292S protein treatment on mouse weight was observed. The average weight of all mice maintained steadily. The average weight for all mice in all three groups was 20.4±1.1 grams by the end of the study.

As shown in FIG. 9, the mice in Group 1 appeared to have normal joints, no detectable inflammatory cell infiltration into the joint and the cartilage and bones appeared normal (FIG. 9, top panel). The mice in Group 2 had severe inflammation in the joints, inflammatory cell infiltration, pannus formation, cartilage damage and bone erosion (FIG. 9, middle panel). The mice in Group 3 treated with hfB3-292S had normal joint structure, no inflammatory cell infiltration, no cartilage or bone erosion or damage (FIG. 9, bottom panel).

These data demonstrated that hfB3-292S was significantly efficacious in preventing joint inflammation and damage in this CAIA mouse model, demonstrating the therapeutic utility of hfB3-292S protein for rheumatoid arthritis.

Example 17. Generation and Characterization of an hfB3-292S-Fc Expression Construct and an hfB3-292S-Fc Protein A stable cell line that expresses hfB3-292S-Fc protein (SEQ ID NO:22) was generated by PEI-mediated transfection and drug selection of 293 cells as described in Example 3. The drug selected cells were cultured at $2 \times 10^6$ cells/mL for 72 hours. Then hfB3-292S-Fc protein expression was examined by subjecting 2 μL of the cell culture supernatant to a non-reducing SDS-PAGE and Western blot analysis. Two bands of hfB3-292S-Fc protein were detected by a goat anti-factor B specific antibody. (Data not shown.) Not wishing to be bound by theory, these two bands of hfB3-292S-Fc protein might represent monomers and dimers of the protein.

hfB3-292S-Fc was purified with a Protein A column. Biological activity of purified hfB3-292S-Fc protein was examined by a hemolytic activity assay as described in Example 7. As shown in Table 6, hfB3-292S-Fc protein inhibited the alternative complement pathway activity in a dose dependent manner

TABLE 6 hfB3-292S-Fc inhibition of human alternative complement pathway hemolytic activity

| | Control w/o wt hfB | Compete with 0.5 μg wt hfB | | | |
|---|---|---|---|---|---|
| Amount of hfB3-292S-Fc (μg) | 0 | 2.0 | 1.0 | 0.5 | 0.3 |
| % inhibition | 100+/−0.0 | 93.8+/−1.9 | 75.4+/−1.2 | 47.3+/−3.2 | 34.0+/−5.3 |

Example 18. C-Terminus Truncated hfB3-292S

A gene expression construct was made that expressed a truncated form of hfB3-292S with the C-terminal 284 amino acids (the serine protease domain) being deleted. The molecule is designated as hfB3-292SN480 which is made up of the N-terminal 480 amino acids of hfB3-292S (amino acids 1-480 of SEQ ID NO:2 or amino acids 26-480 of SEQ ID NO:2 after cleavage of the secretion peptide). The DNA sequence of the expression construct for hfB3-292SN480 is shown in SEQ ID NO:24 with nucleotides 1064-2509 being the coding sequence for hfB3-292SN480. The expression construct was transfected into 293 FreeStyle cells and selected with G418 as described previously in Example 3. The G418 resistant non-clonal cell culture medium was subjected to Western blot analysis for hfB3-292SN480 expression using full-length hfB3-292S as a control (left lane). As shown in FIG. 11, the Western blot analysis with a monoclonal antibody specifically for hfB3-292S detected a band approximately 55 KDa from the cell culture medium of hfB3-292SN480 cell line (right lane), suggesting that even with a 280 amino acid deletion from the C-terminus of hfB3-292S, the N-terminal 480 amino acids can be expressed at an appropriate size.

An alternative complement activity assay was performed as described previously, to determine if hfB3-292SN480 can inhibit alternative complement activity. As shown in FIG. 13 the cell culture supernatant, from cells expressing hfB3-292SN480, inhibited the alternative complement activity in a dose-dependent manner. This demonstrates that fragments of hfB3-292S can still retain the ability to inhibit complement activity and therefore can be utilized the same as described herein for hfB3-292S (SEQ ID NO:2)

Example 19. Monomeric hfB3-292S/Fc Fusion Protein hfB3-292S/Fc-Mono

A gene expression construct encoding a full-length hfB3-292S "fused" to a human IgG4 Fc was engineered. hfB3-292S is a monomer when it is produced in mammalian cells, such as human cells as described previously, e.g., see FIG. 3 described in Example 6 which shows hfB3-292S was detected as one band at approximately MW 100 KDa under non-reducing conditions, suggesting hfB3-292S is a monomer. Two cysteines in the hinge region of the human IgG4 Fc were mutated to ensure the fusion protein would be monomer and retain hfB3-292S's biological property for inhibiting complement activity. The two cysteines were mutated by substituting them each with a serine. This fusion protein of hfB3-292S and the mutated IgG4 Fc was designated hfB3-292S/Fc-mono. The DNA sequence for this fusion protein expression construct is shown in SEQ ID NO:26. The corresponding amino acid sequence for hfB3 292S/Fc mono is shown in SEQ ID NO:25 with amino acids 1-764 being the hfB3-292S region and amino acids 765-1003 being the human IgG4 Fc region with amino acids 782 and 785 being serine amino acids that were substituted for cysteine residues found in a native human IgG4 Fc.

The hfB3-292S/Fc-mono gene expression construct (SEQ ID NO:26) was transfected into human 293 FreeStyle cells. The cells were then subjected to G418 selection. The culture medium from the drug resistant cells was subjected to Western blot analysis for the fusion protein. As shown in FIG. 12, a band at approximately 115 KDa was detected by purified goat anti-human factor B antibody in this non-reducing SDS-PAGE and Western blot analysis. The two higher bands most likely were aggregates of the monomeric fusion protein. The data suggested that the monomeric fusion protein between hfB3-292S and human IgG4 Fc (hfB3-292S/Fc-mono) was successfully expressed in mammalian cells and that the majority of the fusion protein appeared to be monomeric.

To examine if hfB3-292S/Fc-mono preserved hfB3-292S's property of blocking alternative complement activity, an alternative complement activity assay was performed as described previously. As shown in FIG. 14, the cell culture supernatant from hfB3-292S/Fc-mono producing cells inhibited the alternative complement activity in a dose-dependent manner, suggesting that hfB3-292S's complement inhibitory activity was not lost in this monomeric hfB3-292S/Fc-mono fusion protein.

All publications, patents and patent applications mentioned in this specification are herein incorporated by reference in their entirety into the specification to the same extent as if each individual publication, patent or patent application was specifically and individually indicated to be incorporated herein by reference.

What is claimed is:

1. A nucleic acid comprising a nucleotide sequence encoding a polypeptide, the polypeptide comprising a human complement factor B protein analog,
wherein the human complement factor B analog comprises a substitution of a free cysteine amino acid corresponding to amino acid 292 of SEQ ID NO:1 as determined by alignment of the amino acid sequence of the human complement factor B analog with the amino acid sequence of SEQ ID NO: 1; and
the human complement factor B protein analog is at least 90% identical to amino acids 26-764 of SEQ ID NOs: 1, 2 or 3; to amino acids 26-990 of SEQ ID NOs: 22 or 23; to amino acids 26-480 of SEQ ID NO:2; or to amino acids 26-1003 of SEQ ID NO:26.

2. The nucleic acid of claim 1, wherein the free cysteine is substituted with an amino acid selected from the group consisting of alanine, histidine, isoleucine, leucine, methionine, phenylalanine, serine, threonine, tyrosine and valine.

3. The nucleic acid of claim 1, wherein the complement factor B protein analog further comprises mutations corresponding to K258A, R259A, K260A, D279G and N285D of SEQ ID NO:1.

4. The nucleic acid of claim 1, wherein the complement factor B protein analog comprises amino acids 26-480 of SEQ ID NO:2.

5. The nucleic acid of claim 1, wherein the complement factor B protein analog comprises amino acids 26-764 of SEQ ID NO:2.

6. The nucleic acid of claim 1, wherein the complement factor B protein analog comprises a mutation in the C3b binding domain and the complement factor B protein analog exhibits increased binding affinity to C3b as compared to the binding affinity of a corresponding native complement factor B protein to C3b.

7. The nucleic acid of claim 6, wherein the mutation in the C3b binding domain comprises:
(i) a substitution or deletion of an aspartic acid corresponding to amino acid 279 of SEQ ID NO:1, a substitution or deletion of an asparagine corresponding to amino acid 285 of SEQ ID NO:1 or both; or
(ii) an insertion of at least one amino acid next to said aspartic acid or said asparagine.

8. The nucleic acid of claim 1, wherein the polypeptide comprises an immunoglobulin Fc domain.

9. The nucleic acid of claim 1, wherein the complement factor B protein analog exhibits increased binding affinity to factor D as compared to the binding affinity of a corresponding native complement factor B protein to factor D.

10. A viral vector comprising the nucleic acid of claim 1.

11. The viral vector of claim 10, wherein the viral vector is selected from the group consisting of a retroviral vector, a lentiviral vector, an adenoviral vector, a Herpes viral vector, a Hepatitis viral vector, an SV40 viral vector, an AAV vector, an EBV vector and an NDV vector.

12. The viral vector of claim 11, wherein the lentiviral vector is a BIV, HIV, EIAV, SIV or FIV vector.

13. The viral vector of claim 12, wherein the viral vector comprises a decay accelerating factor.

14. A cell comprising the nucleic acid of claim 1, wherein the cell expresses the polypeptide.

15. The cell of claim 14, wherein the cell is a mammalian cell.

16. The cell of claim 14, wherein the cell is selected from the group consisting of a 293 cell, a CHO cell, a PER.C6® (human embryonic retinal tissue-derived cell line) cell and a Vero cell.

17. The cell of claim 14, wherein the cell is a prokaryotic cell.

18. The cell of claim 14, wherein the cell is an *E. coli* cell.

* * * * *

```
                        SEQUENCE LISTING

<160> NUMBER OF SEQ ID NOS: 27

<210> SEQ ID NO 1
<211> LENGTH: 764
<212> TYPE: PRT
<213> ORGANISM: Homo sapiens

<400> SEQUENCE: 1

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
        275                 280                 285

Ala Lys Lys Cys Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
```

```
              340             345             350
Thr Asn Thr Lys Lys Ala Leu Gln Ala Val Tyr Ser Met Met Ser Trp
            355             360             365

Pro Asp Asp Val Pro Pro Glu Gly Trp Asn Arg Thr Arg His Val Ile
        370             375             380

Ile Leu Met Thr Asp Gly Leu His Asn Met Gly Asp Pro Ile Thr
385             390             395             400

Val Ile Asp Glu Ile Arg Asp Leu Leu Tyr Ile Gly Lys Asp Arg Lys
                405             410             415

Asn Pro Arg Glu Asp Tyr Leu Asp Val Tyr Val Phe Gly Val Gly Pro
            420             425             430

Leu Val Asn Gln Val Asn Ile Asn Ala Leu Ala Ser Lys Lys Asp Asn
            435             440             445

Glu Gln His Val Phe Lys Val Lys Asp Met Glu Asn Leu Glu Asp Val
    450             455             460

Phe Tyr Gln Met Ile Asp Glu Ser Gln Ser Leu Ser Leu Cys Gly Met
465             470             475             480

Val Trp Glu His Arg Lys Gly Thr Asp Tyr His Lys Gln Pro Trp Gln
            485             490             495

Ala Lys Ile Ser Val Ile Arg Pro Ser Lys Gly His Glu Ser Cys Met
                500             505             510

Gly Ala Val Val Ser Glu Tyr Phe Val Leu Thr Ala Ala His Cys Phe
            515             520             525

Thr Val Asp Asp Lys Glu His Ser Ile Lys Val Ser Val Gly Gly Glu
        530             535             540

Lys Arg Asp Leu Glu Ile Glu Val Val Leu Phe His Pro Asn Tyr Asn
545             550             555             560

Ile Asn Gly Lys Lys Glu Ala Gly Ile Pro Glu Phe Tyr Asp Tyr Asp
                565             570             575

Val Ala Leu Ile Lys Leu Lys Asn Lys Leu Lys Tyr Gly Gln Thr Ile
            580             585             590

Arg Pro Ile Cys Leu Pro Cys Thr Glu Gly Thr Thr Arg Ala Leu Arg
            595             600             605

Leu Pro Pro Thr Thr Thr Cys Gln Gln Gln Lys Glu Glu Leu Leu Pro
        610             615             620

Ala Gln Asp Ile Lys Ala Leu Phe Val Ser Glu Glu Glu Lys Lys Leu
625             630             635             640

Thr Arg Lys Glu Val Tyr Ile Lys Asn Gly Asp Lys Lys Gly Ser Cys
                645             650             655

Glu Arg Asp Ala Gln Tyr Ala Pro Gly Tyr Asp Lys Val Lys Asp Ile
            660             665             670

Ser Glu Val Val Thr Pro Arg Phe Leu Cys Thr Gly Gly Val Ser Pro
        675             680             685

Tyr Ala Asp Pro Asn Thr Cys Arg Gly Asp Ser Gly Gly Pro Leu Ile
    690             695             700

Val His Lys Arg Ser Arg Phe Ile Gln Val Gly Val Ile Ser Trp Gly
705             710             715             720

Val Val Asp Val Cys Lys Asn Gln Lys Arg Gln Lys Gln Val Pro Ala
                725             730             735

His Ala Arg Asp Phe His Ile Asn Leu Phe Gln Val Leu Pro Trp Leu
            740             745             750

Lys Glu Lys Leu Gln Asp Glu Asp Leu Gly Phe Leu
            755             760
```

<210> SEQ ID NO 2
<211> LENGTH: 764
<212> TYPE: PRT
<213> ORGANISM: Artificial Sequence
<220> FEATURE:
<223> OTHER INFORMATION: complement factor B protein analog

<400> SEQUENCE: 2

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Ala Ala Ala Ile Val Leu Asp Pro Ser Gly Ser Met Asn Ile Tyr
            260                 265                 270

Leu Val Leu Asp Gly Ser Gly Ser Ile Gly Ala Ser Asp Phe Thr Gly
        275                 280                 285

Ala Lys Lys Ser Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365
```

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
            405                 410                 415

Asn Pro Arg Glu Asp Tyr Leu Asp Val Tyr Val Phe Gly Val Gly Pro
        420                 425                 430

Leu Val Asn Gln Val Asn Ile Asn Ala Leu Ala Ser Lys Lys Asp Asn
    435                 440                 445

Glu Gln His Val Phe Lys Val Lys Asp Met Glu Asn Leu Glu Asp Val
450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
            485                 490                 495

Ala Lys Ile Ser Val Ile Arg Pro Ser Lys Gly His Glu Ser Cys Met
        500                 505                 510

Gly Ala Val Val Ser Glu Tyr Phe Val Leu Thr Ala Ala His Cys Phe
    515                 520                 525

Thr Val Asp Asp Lys Glu His Ser Ile Lys Val Ser Val Gly Gly Glu
530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
            565                 570                 575

Val Ala Leu Ile Lys Leu Lys Asn Lys Leu Lys Tyr Gly Gln Thr Ile
        580                 585                 590

Arg Pro Ile Cys Leu Pro Cys Thr Glu Gly Thr Thr Arg Ala Leu Arg
    595                 600                 605

Leu Pro Pro Thr Thr Thr Cys Gln Gln Gln Lys Glu Glu Leu Leu Pro
610                 615                 620

Ala Gln Asp Ile Lys Ala Leu Phe Val Ser Glu Glu Glu Lys Lys Leu
625                 630                 635                 640

Thr Arg Lys Glu Val Tyr Ile Lys Asn Gly Asp Lys Lys Gly Ser Cys
            645                 650                 655

Glu Arg Asp Ala Gln Tyr Ala Pro Gly Tyr Asp Lys Val Lys Asp Ile
        660                 665                 670

Ser Glu Val Val Thr Pro Arg Phe Leu Cys Thr Gly Gly Val Ser Pro
    675                 680                 685

Tyr Ala Asp Pro Asn Thr Cys Arg Gly Asp Ser Gly Gly Pro Leu Ile
690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
            725                 730                 735

His Ala Arg Asp Phe His Ile Asn Leu Phe Gln Val Leu Pro Trp Leu
        740                 745                 750

Lys Glu Lys Leu Gln Asp Glu Asp Leu Gly Phe Leu
    755                 760

<210> SEQ ID NO 3
<211> LENGTH: 764

<212> TYPE: PRT
<213> ORGANISM: Artificial Sequence
<220> FEATURE:
<223> OTHER INFORMATION: complement factor B protein analog

<400> SEQUENCE: 3

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Ala Ala Ala Ile Val Leu Asp Pro Ser Gly Ser Met Asn Ile Tyr
            260                 265                 270

Leu Val Leu Asp Gly Ser Gly Ser Ile Gly Ala Ser Asp Phe Thr Gly
        275                 280                 285

Ala Lys Lys Ser Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380
```

```
Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
            405                 410                 415

Asn Pro Arg Glu Asp Tyr Leu Asp Val Tyr Val Phe Gly Val Gly Pro
        420                 425                 430

Leu Val Asn Gln Val Asn Ile Asn Ala Leu Ala Ser Lys Lys Asp Asn
    435                 440                 445

Glu Gln His Val Phe Lys Val Lys Asp Met Glu Asn Leu Glu Asp Val
450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
    515                 520                 525

Thr Val Asp Asp Lys Glu His Ser Ile Lys Val Ser Val Gly Gly Glu
530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
            645                 650                 655

Glu Arg Asp Ala Gln Tyr Ala Pro Gly Tyr Asp Lys Val Lys Asp Ile
        660                 665                 670

Ser Glu Val Val Thr Pro Arg Phe Leu Cys Thr Gly Gly Val Ser Pro
    675                 680                 685

Tyr Ala Asp Pro Asn Thr Cys Arg Gly Asp Ser Gly Gly Pro Leu Ile
690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asn Phe His Ile Asn Leu Phe Gln Val Leu Pro Trp Leu
            740                 745                 750

Lys Glu Lys Leu Gln Asp Glu Asp Leu Gly Phe Leu
        755                 760
```

<210> SEQ ID NO 4
<211> LENGTH: 764
<212> TYPE: PRT
<213> ORGANISM: Artificial Sequence
<220> FEATURE:
<223> OTHER INFORMATION: complement factor B protein analog

<400> SEQUENCE: 4

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Ala Ala Ala Ile Val Leu Asp Pro Ser Gly Ser Met Asn Ile Tyr
            260                 265                 270

Leu Val Leu Asp Gly Ser Gly Ser Ile Gly Ala Ser Asp Phe Thr Gly
        275                 280                 285

Ala Lys Lys Cys Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
```

405                 410                 415
Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
            435                 440                 445

Glu Gln His Val Phe Lys Val Lys Asp Met Glu Asn Leu Glu Asp Val
            450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
            515                 520                 525

Thr Val Asp Asp Lys Glu His Ser Ile Lys Val Ser Val Gly Gly Glu
            530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
                595                 600                 605

Leu Pro Pro Thr Thr Thr Cys Gln Gln Gln Lys Glu Glu Leu Leu Pro
            610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
            675                 680                 685

Tyr Ala Asp Pro Asn Thr Cys Arg Gly Asp Ser Gly Gly Pro Leu Ile
            690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
            755                 760

<210> SEQ ID NO 5
<211> LENGTH: 7754
<212> TYPE: DNA
<213> ORGANISM: Artificial Sequence
<220> FEATURE:
<223> OTHER INFORMATION: hfB3 expression construct

<400> SEQUENCE: 5
tcaatattgg ccattagcca tattattcat tggttatata gcataaatca atattggcta    60

```
ttggccattg catacgttgt atctatatca taatatgtac atttatattg gctcatgtcc      120
aatatgaccg ccatgttggc attgattatt gactagttat taatagtaat caattacggg      180
gtcattagtt catagcccat atatggagtt ccgcgttaca taacttacgg taaatggccc      240
gcctggctga ccgcccaacg accccccgccc attgacgtca ataatgacgt atgttcccat      300
agtaacgcca tagggacttt ccattgacg tcaatgggtg gagtatttac ggtaaactgc       360
ccacttggca gtacatcaag tgtatcatat gccaagtccg cccctattg acgtcaatga       420 cggtaaatgg cccgcctggc attatgccca gtacatgacc ttacgggact ttcctacttg      480
gcagtacatc tacgtattag tcatcgctat taccatggtg atgcggtttt ggcagtacac      540
caatgggcgt ggatagcggt ttgactcacg gggatttcca gtctccacc ccattgacgt       600 caatgggagt ttgttttggc accaaaatca acgggacttt ccaaaatgtc gtaataaccc      660
cgccccgttg acgcaaatgg gcggtaggcg tgtacggtgg gaggtctata taagcagagc      720
tcgtttagtg aaccgtcaga tcactagaag ctttattgcg gtagtttatc acagttaaat      780
tgctaacgca gtcagtgctt ctgacacaac agtctcgaac ttaagctgca gaagttggtc      840
gtgaggcact gggcaggtaa gtatcaaggt tacaagacag gtttaaggag accaatagaa      900
actgggcttg tcgagacaga gaagactctt gcgtttctga taggcaccta ttggtcttac      960
tgacatccac tttgcctttc tctccacagg tgtccactcc cagttcaatt acagctctta     1020
aggctagagt acttaatacg actcactata ggctagcctc gagaattcac gcgtggtacc     1080
tctagagtcg actagctcct gccccaggcc cagcttctct cctgccttcc aacgccatgg     1140
gctccaacct gtcccccccag ctgtgcctga tgcctttcat cctgggcctg ctgtctggcg     1200
gcgtgaccac cacccttggg tccctggcca ggcctcaggg ctcctgctcc ctggagggcg     1260
tggagatcaa gggcggctcc ttccggctgc tgcaggaagg ccaggctctg gagtacgtgt     1320
gcccttccgg cttctaccct taccctgtgc agacaaggac ctgtaggtcc accggctctt     1380
ggtccacact gaaacccag gaccagaaaa ccgtccggaa ggccgagtgc cgggccatcc     1440
actgccctcg gcctcacgac ttcgagaacg gcgagtactg gcctcggtcc ccttactaca     1500
acgtgtccga cgagatctcc ttccactgct acgacggcta caccctgcgg ggctccgcca     1560
acaggacctg ccaggtcaac ggccggtggt ccggccagac cgccatctgc gacaacggcg     1620
ctggctactg ctccaaccct ggcatcccta tcggcacccg gaaggtcggc tcccagtacc     1680
ggctggagga ctccgtgacc taccactgct ccagaggcct gaccctgaga ggctcccagc     1740
ggcgcacctg tcaggaaggt ggcagctggt ctggcaccga accatcttgc caggactcct     1800
tcatgtacga caccctcag gaagtggccg aggccttcct gtcctccctg accgagacaa     1860
tcgagggcgt ggacgccgag gatggccacg gcctggcga gcagcaggcc gctgccatcg     1920
tgctggaccc ctccggctcc atgaacatct acctggtgct ggacggctcc ggcagcatcg     1980
gcgcctccga cttcaccggc gccaagaagt gcctggtcaa cctgatcgag aaggtggcct     2040
cctacggcgt gaagcctaga tacggcctgg tgacctacgc cacctaccct aagatctggg     2100
tgaaggtgtc cgaggccgac tcctccaacg ccgactgggt gaccaagcag ctgaacgaga     2160
tcaactacga ggaccacaag ctgaagtccg gcaccaacac caagaaggcc ctgcaggcca     2220
tctactccat gatgtcctgg cctgacgacg tgcctcctga gggctggaac cggacccggc     2280
acgtgattat cctgatgacc gacggcctgc acaacatggg cggcgaccct atcaccgtga     2340
tcgacgagat ccgggacctg ctgtacatcg gcaaggaccg gaagaaccct cgggaggact     2400
```

```
acctggacgt gtacgtgttc ggcgtgggcc ctctggtgaa ccaggtcaac atcaacgccc    2460
tggcctccaa gaaggacaac gagcagcacg tgttcaaggt caaggacatg gagaacctgg    2520
aggacgtgtt ctaccagatg atcgatgagt cccagtccct gagcctgtgc ggcatggtct    2580
gggagcaccg caagggaacc gactaccaca agcagccttg gcaggccaag atctccgtga    2640
tccggccttc caagggccac gagtcctgca tgggcgccgt ggtgtccgag tacttcgtgc    2700
tgaccgccgc tcactgcttc accgtggacg acaaggaaca ctccatcaaa gtctccgtgg    2760
gcggcgagaa gcgggacctg gagatcgagg tggtgctgtt ccaccctaac tacaacatca    2820
acggcaagaa ggaagccggc atccctgagt tctacgacta cgacgtggcc ctgatcaagc    2880
tgaagaataa gctgaagtat ggccagacca tccggcctat ctgcctgcct tgcaccgagg    2940
gcaccaccag ggccctgcgg ctgcctccta ccaccacctg ccagcagcag aaggaagagc    3000
tgctgcctgc ccaggacatc aaggccctgt tcgtgtccga ggaagagaag aagctgaccc    3060
ggaaggaagt gtacatcaag aacgcgaca agaagggcag ctgcgagcgg gacgcccagt    3120
acgcccctgg ctacgataag gtcaaggata tctccgaggt ggtgacccct cggttcctgt    3180
gcaccggcgg agtgtccccc tacgccgacc ctaacacctg cagaggcgac tctggcggcc    3240
ctctgatcgt gcacaagcgg tcccggttca tccaggtcgg cgtgatctcc tggggcgtgg    3300
tggacgtgtg caagaaccag aagcggcaga agcaggtccc cgcccacgcc cgggacttcc    3360
acatcaacct gttccaggtg ctgccttggc tgaaggaaaa gctgcaggat gaggacctgg    3420
gcttcctgtg aggggtttcc tgctggacag gggcgtggga ttgacgcccc tctccctccc    3480
cccccctaa cgttactggc cgaagccgct tggaataagg ccggtgtgcg tttgtctata    3540
tgttattttc caccatattg ccgtcttttg gcaatgtgag ggcccggaaa cctggccctg    3600
tcttcttgac gagcattcct aggggtcttt cccctctcgc caaggaatg caaggtctgt    3660
tgaatgtcgt gaaggaagca gttcctctgg aagcttcttg aagacaaaca acgtctgtag    3720
cgacccttttg caggcagcgg aaccccccac ctggcgacag gtgcctctgc ggccaaaagc    3780
cacgtgtata agatacacct gcaaaggcgg cacaacccca gtgccacgtt gtgagttgga    3840
tagttgtgga aagagtcaaa tggctctcct caagcgtatt caacaagggg ctgaaggatg    3900
cccagaaggt accccattgt atgggatctg atctggggcc tcggtgcaca tgctttacat    3960
gtgtttagtc gaggttaaaa aaacgtctag gcccccgaa ccacggggac gtggttttcc    4020
tttgaaaaac acgatgataa gcttgccaca acccgggata attcctgcag ccaatatggg    4080
atcggccatt gaacaagatg gattgcacgc aggttctccg ccgcttggg tggagaggct    4140
attcggctat gactgggcac aacagacaat cggctgctct gatgccgccg tgttccggct    4200
gtcagcgcag gggcgcccgg ttcttttttgt caagaccgac ctgtccggtg ccctgaatga    4260
actgcaggac gaggcagcgc ggctatcgtg gctggccacg acgggcgttc cttgcgcagc    4320
tgtgctcgac gttgtcactg aagcgggaag ggactggctg ctattgggcg aagtgccggg    4380
gcaggatctc ctgtcatctc accttgctcc tgccgagaaa gtatccatca tggctgatgc    4440
aatgcggcgg ctgcatacgc ttgatccggc tacctgccca ttcgaccacc aagcgaaaca    4500
tcgcatcgag cgagcacgta ctcggatgga agccggtctt gtcgatcagg atgatctgga    4560
cgaagagcat caggggctcg cgccagccga actgttcgcc aggctcaagg cgcgcatgcc    4620
cgacggcgat gatctcgtcg tgacccatgg cgatgcctgc ttgccgaata tcatggtgga    4680
aaatggccgc ttttctggat tcatcgactg tggccggctg ggtgtggcgg accgctatca    4740
ggacatagcg ttggctaccc gtgatattgc tgaagagctt ggcggcgaat gggctgaccg    4800
```

```
cttcctcgtg ctttacggta tcgccgctcc cgattcgcag cgcatcgcct tctatcgcct    4860
tcttgacgag ttcttctgag ctagtcgacc cgggcggcct cgagaataaa caatcattat    4920
tttcattgga tctgtgtgtt ggttttttgt gtgggcttgg gggaggggga ggccagaatg    4980
actccaagag ctacaggaag gcaggtcaga gaccccactg gacaaacagt ggctggactc    5040
tgcaccataa cacacaatca acaggggagt gagctggatc gagctgctcg agatccgggc    5100
tggcgtaata gcgaagaggc ccgcaccgat cgcccttccc aacagttgcg cagcctgaat    5160
ggcgaatgga cgcgccctgt agcggcgcat taagcgcggc gggtgtggtg gttacgcgca    5220
gcgtgaccgc tacacttgcc agcgccctag cgcccgctcc tttcgctttc ttcccttcct    5280
ttctcgccac gttcgccggc tttccccgtc aagctctaaa tcggggctc cctttagggt    5340 tccgatttag tgctttacgg cacctcgacc ccaaaaaact tgattagggt gatggttcac    5400
gtagtgggcc atcgccctga tagacggttt ttcgcccttt gacgttggag tccacgttct    5460
ttaatagtgg actcttgttc caaactggaa caacactcaa ccctatctcg gtctattctt    5520
ttgatttata agggattttg ccgatttcgg cctattggtt aaaaaatgag ctgatttaac    5580
aaaaatttaa cgcgaatttt aacaaaatat taacgcttac aatttcctga tgcggtattt    5640
tctccttacg catctgtgcg gtatttcaca ccgcatatgg tgcactctca gtacaatctg    5700
ctctgatgcc gcatagttaa gccagccccg acacccgcca cacccgctg acgcgccctg    5760 acgggcttgt ctgctcccgg catccgctta cagacaagct gtgaccgtct ccgggagctg    5820
catgtgtcag aggttttcac cgtcatcacc gaaacgcgcg agacgaaagg cctcgtgat    5880 acgcctattt ttataggtta atgtcatgat aataatggtt tcttagacgt caggtggcac    5940
ttttcgggga atgtgcgcg gaaccctat tgtttatt ttctaaatac attcaaatat    6000
gtatccgctc atgagacaat aaccctgata atgcttcaa taatattgaa aaaggaagag    6060
tatgagtatt caacatttcc gtgtcgccct tattccctt tttgcggcat tttgccttcc    6120
tgtttttgct cacccagaaa cgctggtgaa agtaaaagat gctgaagatc agttgggtgc    6180
acgagtgggt tacatcgaac tggatctcaa cagcggtaag atccttgaga gttttcgccc    6240
cgaagaacgt tttccaatga tgagcacttt taaagttctg ctatgtggcg cggtattatc    6300
ccgtattgac gccgggcaag agcaactcgg tcgccgcata cactattctc agaatgactt    6360
ggttgagtac tcaccagtca cagaaaagca tcttacggat ggcatgacag taagagaatt    6420
atgcagtgct gccataacca tgagtgataa cactgcggcc aacttacttc tgacaacgat    6480
cggaggaccg aaggagctaa ccgcttttt gcacaacatg gggatcatg taactcgcct    6540 tgatcgttgg gaaccggagc tgaatgaagc cataccaaac gacgagcgtg acaccacgat    6600
gcctgtagca atggcaacaa cgttgcgcaa actattaact ggcgaactac ttactctagc    6660
ttcccggcaa caattaatag actggatgga ggcggataaa gttgcaggac cacttctgcg    6720
ctcggccctt ccggctggct ggtttattgc tgataaatct ggagccggtg agcgtgggtc    6780
tcgcggtatc attgcagcac tggggccaga tggtaagccc tcccgtatcg tagttatcta    6840
cacgacgggg agtcaggcaa ctatggatga acgaaataga cagatcgctg agataggtgc    6900
ctcactgatt aagcattggt aactgtcaga ccaagtttac tcatatatac tttagattga    6960
tttaaaactt catttttaat ttaaaaggat ctaggtgaag atcctttttg ataatctcat    7020
gaccaaaatc ccttaacgtg agttttcgtt ccactgagcg tcagacccccg tagaaaagat    7080 caaaggatct tcttgagatc cttttttct gcgcgtaatc tgctgcttgc aaacaaaaaa    7140
```

```
accaccgcta ccagcggtgg tttgtttgcc ggatcaagag ctaccaactc tttttccgaa    7200
ggtaactggc ttcagcagag cgcagatacc aaatactgtt cttctagtgt agccgtagtt    7260
aggccaccac ttcaagaact ctgtagcacc gcctacatac ctcgctctgc taatcctgtt    7320
accagtggct gctgccagtg gcgataagtc gtgtcttacc gggttggact caagacgata    7380
gttaccggat aaggcgcagc ggtcgggctg aacgggggt tcgtgcacac agcccagctt     7440
ggagcgaacg acctacaccg aactgagata cctacagcgt gagctatgag aaagcgccac    7500
gcttcccgaa gggagaaagg cggacaggta tccggtaagc ggcagggtcg aacaggaga    7560 gcgcacgagg gagcttccag ggggaaacgc ctggtatctt tatagtcctg tcgggtttcg    7620
ccacctctga cttgagcgtc gatttttgtg atgctcgtca gggggcgga gcctatggaa     7680 aaacgccagc aacgcggcct ttttacggtt cctggccttt gctggccttt tgctcacat    7740 ggctcgacag atct                                                      7754

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
caccggcgcc aagaagagcc tggtcaacct gatc                                34

<210> SEQ ID NO 7
<211> LENGTH: 34
<212> TYPE: DNA
<213> ORGANISM: Artificial Sequence
<220> FEATURE:
<223> OTHER INFORMATION: primer

<400> SEQUENCE: 7
gatcaggttg accaggctct tcttggcgcc ggtg                                34

<210> SEQ ID NO 8
<211> LENGTH: 7754
<212> TYPE: DNA
<213> ORGANISM: Artificial Sequence
<220> FEATURE:
<223> OTHER INFORMATION: expression construct

<400> SEQUENCE: 8
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg    180
gtcattagtt catagcccat atatggagtt ccgcgttaca aacttacgg taaatggccc      240 gcctggctga cgcccaacg acccccgccc attgacgtca ataatgacgt atgttcccat     300
agtaacgcca atagggactt tccattgacg tcaatgggtg gagtatttac ggtaaactgc    360
ccacttggca gtacatcaag tgtatcatat gccaagtccg cccctattg acgtcaatga     420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
```

```
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga gaagactctt gcgtttctga taggcaccta ttggtcttac     960
tgacatccac tttgcctttc tctccacagg tgtccactcc cagttcaatt acagctctta    1020
aggctagagt acttaatacg actcactata ggctagcctc gagaattcac gcgtggtacc    1080
tctagagtcg actagctcct gccccaggcc cagcttctct cctgccttcc aacgccatgg    1140
gctccaacct gtcccccag ctgtgcctga tgcctttcat cctgggcctg ctgtctggcg    1200
gcgtgaccac cacccttgg tccctggcca ggcctcaggg ctcctgctcc ctggagggcg    1260
tggagatcaa gggcggctcc ttccggctgc tgcaggaagg ccaggctctg gagtacgtgt    1320
gcccttccgg cttctaccct taccctgtgc agacaaggac ctgtaggtcc accggctctt    1380
ggtccacact gaaacccag gaccagaaaa ccgtccggaa ggccgagtgc cgggccatcc    1440
actgccctcg gcctcacgac ttcgagaacg gcgagtactg gcctcggtcc ccttactaca    1500
acgtgtccga cgagatctcc ttccactgct acgacggcta caccctgcgg ggctccgcca    1560
acaggacctg ccaggtcaac ggccggtggt ccggccagac cgccatctgc gacaacggcg    1620
ctggctactg ctccaaccct ggcatcccta tcggcacccg gaaggtcggc tcccagtacc    1680
ggctggagga ctccgtgacc taccactgct ccagaggcct gaccctgaga ggctcccagc    1740
ggcgcacctg tcaggaaggt ggcagctggt ctggcaccga accatcttgc caggactcct    1800
tcatgtacga caccctcag gaagtggccg aggccttcct gtcctccctg accgagacaa    1860
tcgagggcgt ggacgccgag gatgccacg gccctggcga gcagcaggcc gctgccatcg    1920
tgctggaccc ctccggctcc atgaacatct acctggtgct ggacggctcc ggcagcatcg    1980
gcgcctccga cttcaccggc gccaagaaga gcctggtcaa cctgatcgag aaggtggcct    2040
cctacggcgt gaagcctaga tacggcctgg tgacctacgc cacctaccct aagatctggg    2100
tgaaggtgtc cgaggccgac tcctccaacg ccgactgggt gaccaagcag ctgaacgaga    2160
tcaactacga ggaccacaag ctgaagtccg gcaccaacac caagaaggcc ctgcaggccg    2220
tctactccat gatgtcctgg cctgacgacg tgcctcctga gggctggaac cggacccggc    2280
acgtgattat cctgatgacc gacggcctgc acaacatggg cggcgaccct atcaccgtga    2340
tcgacgagat ccgggacctg ctgtacatcg gcaaggaccg gaagaaccct cgggaggact    2400
acctggacgt gtacgtgttc ggcgtgggcc ctctggtgaa ccaggtcaac atcaacgccc    2460
tggcctccaa gaaggacaac gagcagcacg tgttcaaggt caaggacatg gagaacctgg    2520
aggacgtgtt ctaccagatg atcgatgagt cccagtccct gagcctgtgc ggcatggtct    2580
gggagcaccg caagggaacc gactaccaca gcagccttg gcaggccaag atctccgtga    2640
tccggccttc caagggccac gagtcctgca tgggcgccgt ggtgtccgag tacttcgtgc    2700
tgaccgccgc tcactgcttc accgtggacg acaaggaaca ctccatcaaa gtctccgtgg    2760
gcggcgagaa gcgggacctg gagatcgagg tggtgctgtt ccaccctaac tacaacatca    2820
acggcaagaa ggaagccggc atccctgagt tctacgacta cgacgtggcc ctgatcaagc    2880
tgaagaataa gctgaagtat ggccagacca tccggcctat ctgcctgcct tgcaccgagg    2940
gcaccaccag ggccctgcgg ctgcctccta ccacccctg ccagcagcag aaggaagagc    3000
tgctgcctgc ccaggacatc aaggccctgt tcgtgtccga ggaagagaag aagctgaccc    3060
```

```
ggaaggaagt gtacatcaag aacggcgaca agaagggcag ctgcgagcgg gacgcccagt    3120
acgcccctgg ctacgataag gtcaaggata tctccgaggt ggtgacccct cggttcctgt    3180
gcaccggcgg agtgtccccc tacgccgacc ctaacacctg cagaggcgac tctggcggcc    3240
ctctgatcgt gcacaagcgg tcccggttca tccaggtcgg cgtgatctcc tggggcgtgg    3300
tggacgtgtg caagaaccag aagcggcaga agcaggtccc cgcccacgcc cgggacttcc    3360
acatcaacct gttccaggtg ctgccttggc tgaaggaaaa gctgcaggat gaggacctgg    3420
gcttcctgtg aggggtttcc tgctggacag gggcgtggga ttgacgcccc tctccctccc    3480 cccccccctaa cgttactggc cgaagccgct tggaataagg ccggtgtgcg tttgtctata    3540
tgttattttc caccatattg ccgtcttttg gcaatgtgag ggcccggaaa cctggccctg    3600
tcttcttgac gagcattcct aggggtcttt cccctctcgc caaaggaatg caaggtctgt    3660
tgaatgtcgt gaaggaagca gttcctctgg aagcttcttg aagacaaaca acgtctgtag    3720
cgacccttgt caggcagcgg aacccccac ctggcgacag gtgcctctgc ggccaaaagc    3780
cacgtgtata agatacacct gcaaaggcgg cacaacccca gtgccacgtt gtgagttgga    3840
tagttgtgga aagagtcaaa tggctctcct caagcgtatt caacaagggg ctgaaggatg    3900
cccagaaggt accccattgt atgggatctg atctggggcc tcggtgcaca tgctttacat    3960
gtgtttagtc gaggttaaaa aaacgtctag gccccccgaa ccacggggac gtggttttcc    4020
tttgaaaaac acgatgataa gcttgccaca acccgggata attcctgcag ccaatatggg    4080
atcggccatt gaacaagatg gattgcacgc aggttctccg gccgcttggg tggagaggct    4140
attcggctat gactgggcac aacagacaat cggctgctct gatgccgccg tgttccggct    4200
gtcagcgcag gggcgcccgg ttcttttttgt caagaccgac ctgtccggtg ccctgaatga    4260
actgcaggac gaggcagcgc ggctatcgtg gctggccacg acgggcgttc cttgcgcagc    4320
tgtgctcgac gttgtcactg aagcgggaag ggactggctg ctattgggcg aagtgccggg    4380
gcaggatctc ctgtcatctc accttgctcc tgccgagaaa gtatccatca tggctgatgc    4440
aatgcggcgg ctgcatacgc ttgatccggc tacctgccca ttcgaccacc aagcgaaaca    4500
tcgcatcgag cgagcacgta ctcggatgga agccggtctt gtcgatcagg atgatctgga    4560
cgaagagcat caggggctcg cgccagccga actgttcgcc aggctcaagg cgcgcatgcc    4620
cgacggcgat gatctcgtcg tgacccatgg cgatgcctgc ttgccgaata tcatggtgga    4680
aaatggccgc ttttctggat tcatcgactg tggccggctg ggtgtggcgg accgctatca    4740
ggacatagcg ttggctaccc gtgatattgc tgaagagctt ggcggcgaat gggctgaccg    4800
cttcctcgtg ctttacggta tcgccgctcc cgattcgcag cgcatcgcct tctatcgcct    4860
tcttgacgag ttcttctgag ctagtcgacc cgggcggcct cgagaataaa caatcattat    4920
tttcattgga tctgtgtgtt ggttttttgt gtgggcttgg ggaggggga ggccagaatg    4980 actccaagag ctacaggaag gcaggtcaga gaccccactg gacaaacagt ggctggactc    5040
tgcaccataa cacacaatca acaggggagt gagctggatc gagctgctcg agatccgggc    5100
tggcgtaata gcgaagaggc ccgcaccgat cgcccttccc aacagttgcg cagcctgaat    5160
ggcgaatgga cgcgccctgt agcggcgcat taagcgcggc gggtgtggtg gttacgcgca    5220
gcgtgaccgc tacacttgcc agcgccctag cgcccgctcc tttcgctttc ttcccttcct    5280
ttctcgccac gttcgccggc tttccccgtc aagctctaaa tcggggctc cctttagggt    5340 tccgatttag tgctttacgg cacctcgacc ccaaaaaact tgattagggt gatggttcac    5400
gtagtgggcc atcgccctga tagacggttt ttcgccctt gacgttggag tccacgttct    5460
```

```
ttaatagtgg actcttgttc caaactggaa caacactcaa ccctatctcg gtctattctt    5520
ttgatttata agggatttttg ccgatttcgg cctattggtt aaaaaatgag ctgatttaac    5580
aaaaatttaa cgcgaatttt aacaaaatat taacgcttac aatttcctga tgcggtattt    5640
tctccttacg catctgtgcg gtatttcaca ccgcatatgg tgcactctca gtacaatctg    5700
ctctgatgcc gcatagttaa gccagccccg acacccgcca acacccgctg acgcgccctg    5760
acgggcttgt ctgctcccgg catccgctta cagacaagct gtgaccgtct ccgggagctg    5820
catgtgtcag aggttttcac cgtcatcacc gaaacgcgcg agacgaaagg cctcgtgat    5880 acgcctattt ttataggtta atgtcatgat aataatggtt tcttagacgt caggtggcac    5940
ttttcgggga atgtgcgcg gaaccctat ttgtttattt ttctaaatac attcaaatat    6000
gtatccgctc atgagacaat aaccctgata aatgcttcaa taatattgaa aaaggaagag    6060
tatgagtatt caacatttcc gtgtcgccct tattccctttt tttgcggcat tttgccttcc    6120
tgtttttgct cacccagaaa cgctggtgaa agtaaaagat gctgaagatc agttgggtgc    6180
acgagtgggt tacatcgaac tggatctcaa cagcggtaag atccttgaga gttttcgccc    6240
cgaagaacgt tttccaatga tgagcacttt taaagttctg ctatgtggcg cggtattatc    6300
ccgtattgac gccgggcaag agcaactcgg tcgccgcata cactattctc agaatgactt    6360
ggttgagtac tcaccagtca cagaaaagca tcttacggat ggcatgacag taagagaatt    6420
atgcagtgct gccataacca tgagtgataa cactgcggcc aacttacttc tgacaacgat    6480
cggaggaccg aaggagctaa ccgcttttt gcacaacatg ggggatcatg taactcgcct    6540
tgatcgttgg gaaccggagc tgaatgaagc cataccaaac gacgagcgtg acaccacgat    6600
gcctgtagca atggcaacaa cgttgcgcaa actattaact ggcgaactac ttactctagc    6660
ttcccggcaa caattaatag actggatgga ggcggataaa gttgcaggac cacttctgcg    6720
ctcggccctt ccggctggct ggtttattgc tgataaatct ggagccggtg agcgtgggtc    6780
tcgcggtatc attgcagcac tggggccaga tggtaagccc tcccgtatcg tagttatcta    6840
cacgacgggg agtcaggcaa ctatggatga acgaaataga cagatcgctg agataggtgc    6900
ctcactgatt aagcattggt aactgtcaga ccaagtttac tcatatatac tttagattga    6960
tttaaaactt catttttaat ttaaaaggat ctaggtgaag atcctttttg ataatctcat    7020
gaccaaaatc ccttaacgtg agttttcgtt ccactgagcg tcagaccccg tagaaaagat    7080
caaaggatct tcttgagatc ctttttttct gcgcgtaatc tgctgcttgc aaacaaaaaa    7140
accaccgcta ccagcggtgg tttgtttgcc ggatcaagag ctaccaactc tttttccgaa    7200
ggtaactggc ttcagcagag cgcagatacc aaatactgtt cttctagtgt agccgtagtt    7260
aggccaccac ttcaagaact ctgtagcacc gcctacatac ctcgctctgc taatcctgtt    7320
accagtggct gctgccagtg gcgataagtc gtgtcttacc gggttggact caagacgata    7380
gttaccggat aaggcgcagc ggtcgggctg aacggggggt tcgtgcacac agcccagctt    7440
ggagcgaacg acctacaccg aactgagata cctacagcgt gagctatgag aaagcgccac    7500
gcttcccgaa gggagaaagg cggacaggta tccggtaagc ggcagggtcg gaacaggaga    7560
gcgcacgagg gagcttccag ggggaaacgc ctggtatctt tatagtcctg tcgggtttcg    7620
ccacctctga cttgagcgtc gatttttgtg atgctcgtca ggggggcgga gcctatggaa    7680
aaacgccagc aacgcggcct ttttacggtt cctggccttt tgctggcctt ttgctcacat    7740
ggctcgacag atct                                                     7754
```

<210> SEQ ID NO 9
<211> LENGTH: 23
<212> TYPE: PRT
<213> ORGANISM: Homo sapiens

<400> SEQUENCE: 9

Ile Gly Ala Ser Asn Phe Thr Gly Ala Lys Lys Cys Leu Val Asn Leu
1               5                   10                  15

Ile Glu Lys Val Ala Ser Tyr
            20

<210> SEQ ID NO 10
<211> LENGTH: 23
<212> TYPE: PRT
<213> ORGANISM: Mus musculus

<400> SEQUENCE: 10

Ile Gly Ser Ser Asn Phe Thr Gly Ala Lys Arg Cys Leu Thr Asn Leu
1               5                   10                  15

Ile Glu Lys Val Ala Ser Tyr
            20

<210> SEQ ID NO 11
<211> LENGTH: 23
<212> TYPE: PRT
<213> ORGANISM: Rattus norvegicus

<400> SEQUENCE: 11

Ile Gly Ala Ser Asn Phe Thr Gly Ala Lys Arg Cys Leu Ala Asn Leu
1               5                   10                  15

Ile Glu Lys Val Ala Ser Tyr
            20

<210> SEQ ID NO 12
<211> LENGTH: 23
<212> TYPE: PRT
<213> ORGANISM: Sus scrofa

<400> SEQUENCE: 12

Ile Gly Ala Arg Asn Phe Thr Gly Ala Lys Asn Cys Leu Lys Asp Phe
1               5                   10                  15

Ile Glu Lys Val Ala Ser Tyr
            20

<210> SEQ ID NO 13
<211> LENGTH: 23
<212> TYPE: PRT
<213> ORGANISM: Macaca mulatta

<400> SEQUENCE: 13

Ile Gly Ala Gly Asn Phe Thr Gly Ala Lys Lys Cys Leu Val Asn Leu
1               5                   10                  15

Ile Glu Lys Val Ala Ser Tyr
            20

<210> SEQ ID NO 14
<211> LENGTH: 23
<212> TYPE: PRT
<213> ORGANISM: Ovis aries

<400> SEQUENCE: 14

Val Gly Ala His Asn Phe Thr Gly Ala Lys Asn Cys Leu Arg Asp Phe

```
                1               5                    10                     15
Ile Glu Lys Val Ala Ser Tyr
                20
```

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
gtccccgccc acgcccggaa cttccacatc aacctgttcc                                40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
ggaacaggtt gatgtggaag ttccgggcgt gggcggggac                                40

<210> SEQ ID NO 17
<211> LENGTH: 764
<212> TYPE: PRT
<213> ORGANISM: Artificial Sequence
<220> FEATURE:
<223> OTHER INFORMATION: complement factor B protein analog

<400> SEQUENCE: 17

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
                20                  25                  30

Pro Gln Gly Ser Cys Ser Leu Glu Gly Val Glu Ile Lys Gly Gly Ser
            35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
```

```
            210                 215                 220
Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Ala Ala Ala Ile Val Leu Asp Pro Ser Gly Ser Met Asn Ile Tyr
                260                 265                 270

Leu Val Leu Asp Gly Ser Gly Ser Ile Gly Ala Ser Asp Phe Thr Gly
                275                 280                 285

Ala Lys Lys Cys Leu Val Asn Leu Ile Glu Lys Val Ala Ser Tyr Gly
                290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
                340                 345                 350

Thr Asn Thr Lys Lys Ala Leu Gln Ala Val Tyr Ser Met Met Ser Trp
                355                 360                 365

Pro Asp Asp Val Pro Pro Glu Gly Trp Asn Arg Thr Arg His Val Ile
                370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
                420                 425                 430

Leu Val Asn Gln Val Asn Ile Asn Ala Leu Ala Ser Lys Lys Asp Asn
                435                 440                 445

Glu Gln His Val Phe Lys Val Lys Asp Met Glu Asn Leu Glu Asp Val
                450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
                500                 505                 510

Gly Ala Val Val Ser Glu Tyr Phe Val Leu Thr Ala Ala His Cys Phe
                515                 520                 525

Thr Val Asp Asp Lys Glu His Ser Ile Lys Val Ser Val Gly Gly Glu
530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
                580                 585                 590

Arg Pro Ile Cys Leu Pro Cys Thr Glu Gly Thr Thr Arg Ala Leu Arg
                595                 600                 605

Leu Pro Pro Thr Thr Thr Cys Gln Gln Gln Lys Glu Glu Leu Leu Pro
                610                 615                 620

Ala Gln Asp Ile Lys Ala Leu Phe Val Ser Glu Glu Lys Lys Leu
625                 630                 635                 640
```

```
Thr Arg Lys Glu Val Tyr Ile Lys Asn Gly Asp Lys Gly Ser Cys
                645                 650                 655
Glu Arg Asp Ala Gln Tyr Ala Pro Gly Tyr Asp Lys Val Lys Asp Ile
            660                 665                 670
Ser Glu Val Val Thr Pro Arg Phe Leu Cys Thr Gly Gly Val Ser Pro
        675                 680                 685
Tyr Ala Asp Pro Asn Thr Cys Arg Gly Asp Ser Gly Pro Leu Ile
    690                 695                 700
Val His Lys Arg Ser Arg Phe Ile Gln Val Gly Val Ile Ser Trp Gly
705                 710                 715                 720
Val Val Asp Val Cys Lys Asn Gln Lys Arg Gln Lys Val Pro Ala
                725                 730                 735
His Ala Arg Asn Phe His Ile Asn Leu Phe Gln Val Leu Pro Trp Leu
            740                 745                 750
Lys Glu Lys Leu Gln Asp Glu Asp Leu Gly Phe Leu
        755                 760

<210> SEQ ID NO 18
<211> LENGTH: 8465
<212> TYPE: DNA
<213> ORGANISM: Artificial Sequence
<220> FEATURE:
<223> OTHER INFORMATION: expression construct

<400> SEQUENCE: 18
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg acccccgccc attgacgtca ataatgacgt atgttcccat   300
agtaacgcca atagggactt tccattgacg tcaatgggtg gagtatttac ggtaaactgc   360
ccacttggca gtacatcaag tgtatcatat gccaagtccg cccctattg acgtcaatga    420
cggtaaatgg cccgcctggc attatgccca gtacatgacc ttacgggact ttcctacttg   480
gcagtacatc tacgtattag tcatcgctat taccatggtg atgcggtttt ggcagtacac   540
caatgggcgt ggatagcggt ttgactcacg ggatttccaa gtctccacc ccattgacgt     600
caatgggagt ttgttttggc accaaaatca acgggacttt ccaaaatgtc gtaataaccc   660
cgccccgttg acgcaaatgg gcggtaggcg tgtacggtgg gaggtctata taagcagagc   720
tcgtttagtg aaccgtcaga tcactagaag ctttattgcg gtagtttatc acagttaaat   780
tgctaacgca gtcagtgctt ctgacacaac agtctcgaac ttaagctgca gaagttggtc   840
gtgaggcact gggcaggtaa gtatcaaggt tacaagacag gtttaaggag accaatagaa   900
actgggcttg tcgagacaga gaagactctt gcgtttctga taggcaccta ttggtcttac   960
tgacatccac tttgcctttc tctccacagg tgtccactcc cagttcaatt acagctctta  1020
aggctagagt acttaatacg actcactata ggctagcgaa ttcacgcgtg gtacctctag  1080
agtcgactag ctcctgcccc aggcccagct tctctcctgc cttccaacgc catgggctcc  1140
aacctgtccc cccagctgtg cctgatgcct ttcatcctgg gcctgctgtc tggcggcgtg  1200
accaccaccc cttggtccct ggccaggcct cagggctcct gctccctgga gggcgtggag  1260
atcaagggcg gctccttccg gctgctgcag gaaggccagg ctctggagta cgtgtgccct  1320
```

```
tccggcttct acccttaccc tgtgcagaca aggacctgta ggtccaccgg ctcttggtcc    1380
acactgaaaa cccaggacca gaaaaccgtc cggaaggccg agtgccgggc catccactgc    1440
cctcggcctc acgacttcga gaacggcgag tactggcctc ggtcccctta ctacaacgtg    1500
tccgacgaga tctccttcca ctgctacgac ggctacaccc tgcggggctc cgccaacagg    1560
acctgccagg tcaacggccg gtggtccggc cagaccgcca tctgcgacaa cggcgctggc    1620
tactgctcca accctggcat ccctatcggc acccggaagg tcggctccca gtaccggctg    1680
gaggactccg tgacctacca ctgctccaga ggcctgaccc tgagaggctc ccagcggcgc    1740
acctgtcagg aaggtggcag ctggtctggc accgaaccat cttgccagga ctccttcatg    1800
tacgacaccc ctcaggaagt ggccgaggcc ttcctgtcct ccctgaccga acaatcgag    1860 ggcgtggacg ccgaggatgg ccacggccct ggcgagcagc aggccgctgc catcgtgctg    1920
gacccctccg gctccatgaa catctacctg gtgctggacg gctccggcag catcggcgcc    1980
tccgacttca ccggcgccaa gaagtgcctg gtcaacctga tcgagaaggt ggcctcctac    2040
ggcgtgaagc ctagatacgg cctggtgacc tacgccacct accctaagat ctgggtgaag    2100
gtgtccgagg ccgactcctc caacgccgac tgggtgacca agcagctgaa cgagatcaac    2160
tacgaggacc acaagctgaa gtccggcacc aacaccaaga aggccctgca ggccgtctac    2220
tccatgatgt cctggcctga cgacgtgcct cctgagggct ggaaccggac ccggcacgtg    2280
attatcctga tgaccgacgg cctgcacaac atgggcggcg accctatcac cgtgatcgac    2340
gagatccggg acctgctgta catcggcaag gaccggaaga accctcggga ggactacctg    2400
gacgtgtacg tgttcggcgt gggccctctg gtgaaccagg tcaacatcaa cgccctggcc    2460
tccaagaagg acaacgagca gcacgtgttc aaggtcaagg acatggagaa cctggaggac    2520
gtgttctacc agatgatcga tgagtcccag tccctgagcc tgtgcggcat ggtctgggag    2580
caccgcaagg gaaccgacta ccacaagcag ccttggcagg ccaagatctc cgtgatccgg    2640
ccttccaagg gccacgagtc ctgcatgggc gccgtggtgt ccgagtactt cgtgctgacc    2700
gccgctcact gcttcaccgt ggacgacaag gaacactcca tcaaagtctc cgtgggcggc    2760
gagaagcggg acctggagat cgaggtggtg ctgttccacc ctaactacaa catcaacggc    2820
aagaaggaag ccggcatccc tgagttctac gactacgacg tggccctgat caagctgaag    2880
aataagctga agtatggcca gaccatccgg cctatctgcc tgccttgcac cgagggcacc    2940
accagggccc tgcggctgcc tcctaccacc acctgccagc agcagaagga agagctgctg    3000
cctgcccagg acatcaaggc cctgttcgtg tccgaggaag agaagaagct gacccggaag    3060
gaagtgtaca tcaagaacgg cgacaagaag ggcagctgcg agcgggacgc ccagtacgcc    3120
cctggctacg ataaggtcaa ggatatctcc gaggtggtga cccctcggtt cctgtgcacc    3180
ggcggagtgt ccccctacgc cgaccctaac acctgcagag gcgactctgg cggccctctg    3240
atcgtgcaca gcggtcccg gttcatccag gtcggcgtga tctcctgggg cgtggtggac    3300
gtgtgcaaga accagaagcg gcagaagcag gtccccgccc acgcccggga cttccacatc    3360
aacctgttcc aggtgctgcc ttggctgaag gaaaagctgc aggatgagga cctgggcttc    3420
ctgagatctc ccccatgccc atcatgccca gcacctgagt tcctgggggg accatcagtc    3480
ttcctgttcc ccccaaaacc caaggacact ctcatgatct cccggacccc tgaggtcacg    3540
tgcgtggtgg tggacgtgag ccaggaagac cccgaggtcc agttcaactg gtacgtggat    3600
ggcgtggagg tgcataatgc caagacaaag ccgcgggagg agcagttcaa cagcacgtac    3660
cgtgtggtca gcgtcctcac cgtcctgcac caggactggc tgaacggcaa ggagtacaag    3720
```

```
tgcaaggtct ccaacaaagg cctcccgtcc tccatcgaga aaaccatctc caaagccaaa    3780
gggcagcccc gagagccaca ggtgtacacc ctgcccccat cccaggagga gatgaccaag    3840
aaccaggtca gcctgacctg cctggtcaaa ggcttctacc ccagcgacat cgccgtggag    3900
tgggagagca atgggcagcc ggagaacaac tacaagacca cgcctcccgt gctggactcc    3960
gacggctcct tcttcctcta cagcaggcta accgtggaca agagcaggtg gcaggagggg    4020
aatgtcttct catgctccgt gatgcatgag gctctgcaca accactacac acagaagagc    4080
ctctccctgt ctccgggtaa atgagtgcta gcctcgagaa ttcacgcgtg gtacctctag    4140
agtcgatcta gggcggccaa ttccgcccct ccctccccc ccccctaac gttactggcc    4200 gaagccgctt ggaataaggc cggtgtgcgt ttgtctatat gttatttcc accatattgc    4260 cgtcttttgg caatgtgagg gcccggaaac ctggccctgt cttcttgacg agcattccta    4320
ggggtctttc cctctcgcc aaaggaatgc aaggtctgtt gaatgtcgtg aaggaagcag    4380
ttcctctgga agcttcttga agacaaacaa cgtctgtagc gacccttgc aggcagcgga    4440 accccccacc tggcgacagg tgcctctgcg gccaaaagcc acgtgtataa gatacacctg    4500
caaaggcgga caaccccag tgccacgttg tgagttggat agttgtggaa agagtcaaat    4560
ggctctcctc aagcgtattc aacaagggc tgaaggatgc ccagaaggta ccccattgta    4620
tgggatctga tctgggcct cggtgcacat gctttacatg tgtttagtcg aggttaaaa    4680 aacgtctagg ccccccgaac cacggggacg tggttttcct ttgaaaaaca cgatgataag    4740
cttgccacaa cccgggataa ttcctgcagc caatatggga tcggccattg aacaagatgg    4800
attgcacgca ggttctccgg ccgcttgggt ggagaggcta ttcggctatg actgggcaca    4860
acagacaatc ggctgctctg atgccgccgt gttccggctg tcagcgcagg ggcgcccggt    4920
tctttttgtc aagaccgacc tgtccggtgc cctgaatgaa ctgcaggacg aggcagcgcg    4980
gctatcgtgg ctggccacga cgggcgttcc ttgcgcagct gtgctcgacg ttgtcactga    5040
agcgggaagg gactggctgc tattgggcga agtgccgggg caggatctcc tgtcatctca    5100
ccttgctcct gccgagaaag tatccatcat ggctgatgca atgcggcggc tgcatacgct    5160
tgatccggct acctgcccat tcgaccacca agcgaaacat cgcatcgagc gagcacgtac    5220
tcggatggaa gccggtcttg tcgatcagga tgatctggac gaagagcatc aggggctcgc    5280
gccagccgaa ctgttcgcca ggctcaaggc gcgcatgccc gacggcgatg atctcgtcgt    5340
gacccatggc gatgcctgct tgccgaatat catggtggaa aatggccgct tttctggatt    5400
catcgactgt ggccggctgg gtgtggcgga ccgctatcag gacatagcgt tggctacccg    5460
tgatattgct gaagagcttg gcggcgaatg ggctgaccgc ttcctcgtgc tttacggtat    5520
cgccgctccc gattcgcagc gcatcgcctt ctatcgcctt cttgacgagt tcttctgagg    5580
ggatcaattc tctagtcgac ccgggcggcc tcgagaataa acaatcatta ttttcattgg    5640
atctgtgtgt tggttttttg tgtgggcttg gggaggggg aggccagaat gactccaaga    5700
gctacaggaa ggcaggtcag agaccccact ggacaaacag tggctggact ctgcaccata    5760
acacacaatc aacaggggag tgagctggat cgagctgctc gagatccggg ctggcgtaat    5820
agcgaagagg cccgcaccga tcgcccttcc caacagttgc gcagcctgaa tggcgaatgg    5880
acgcgccctg tagcggcgca ttaagcgcgg cgggtgtggt ggttacgcgc agcgtgaccg    5940
ctacacttgc cagcgcccta gcgcccgctc ctttcgcttt cttcccttcc tttctcgcca    6000
cgttcgccgg ctttccccgt caagctctaa atcgggggct ccctttaggg ttccgattta    6060
```

```
gtgctttacg gcacctcgac cccaaaaaac ttgattaggg tgatggttca cgtagtgggc    6120
catcgccctg atagacggtt tttcgcccett tgacgttgga gtccacgttc tttaatagtg    6180
gactcttgtt ccaaactgga acaacactca accctatctc ggtctattct tttgatttat    6240
aagggatttt gccgatttcg gcctattggt taaaaaatga gctgatttaa caaaaattta    6300
acgcgaattt taacaaaata ttaacgctta caatttcctg atgcggtatt ttctccttac    6360
gcatctgtgc ggtatttcac accgcatatg gtgcactctc agtacaatct gctctgatgc    6420
cgcatagtta agccagcccc gacacccgcc aacacccgct gacgcgccct gacgggcttg    6480
tctgctcccg gcatccgctt acagacaagc tgtgaccgtc tccgggagct gcatgtgtca    6540
gaggttttca ccgtcatcac cgaaacgcgc gagacgaaag gcctcgtga tacgcctatt      6600
tttataggtt aatgtcatga taataatggt ttcttagacg tcaggtggca cttttcgggg    6660
aaatgtgcgc ggaacccta tttgtttatt tttctaaata cattcaaata tgtatccgct      6720
catgagacaa taaccctgat aaatgcttca ataatattga aaaggaaga gtatgagtat      6780
tcaacatttc cgtgtcgccc ttattccctt ttttgcggca ttttgccttc ctgttttttgc    6840
tcacccagaa acgctggtga agtaaaaga tgctgaagat cagttgggtg cacgagtggg      6900
ttacatcgaa ctggatctca acagcggtaa gatccttgag agttttcgcc ccgaagaacg    6960
ttttccaatg atgagcactt ttaaagttct gctatgtggc gcggtattat cccgtattga    7020
cgccgggcaa gagcaactcg gtcgccgcat acactattct cagaatgact tggttgagta    7080
ctcaccagtc acagaaaagc atcttacgga tggcatgaca gtaagagaat tatgcagtgc    7140
tgccataacc atgagtgata acactgcggc caacttactt ctgacaacga tcggaggacc    7200
gaaggagcta accgcttttt tgcacaacat ggggatcat gtaactcgcc ttgatcgttg      7260
ggaaccggag ctgaatgaag ccataccaaa cgacgagcgt gacaccacga tgcctgtagc    7320
aatggcaaca acgttgcgca aactattaac tggcgaacta cttactctag cttcccggca    7380
acaattaata gactggatgg aggcggataa agttgcagga ccacttctgc gctcggccct    7440
tccggctggc tggtttattg ctgataaatc tggagccggt gagcgtgggt ctcgcggtat    7500
cattgcagca ctggggccag atggtaagcc ctcccgtatc gtagttatct acacgacggg    7560
gagtcaggca actatggatg aacgaaatag acagatcgct gagataggtg cctcactgat    7620
taagcattgg taactgtcag accaagttta ctcatatata ctttagattg atttaaaact    7680
tcatttttaa tttaaaagga tctaggtgaa gatccttttt gataatctca tgaccaaaat    7740
cccttaacgt gagttttcgt tccactgagc gtcagacccc gtagaaaaga tcaaaggatc    7800
ttcttgagat cctttttttc tgcgcgtaat ctgctgcttg caaacaaaaa aaccaccgct    7860
accagcggtg gtttgtttgc cggatcaaga gctaccaact ctttttccga aggtaactgg    7920
cttcagcaga gcgcagatac caaatactgt tcttctagtg tagccgtagt taggccacca    7980
cttcaagaac tctgtagcac cgcctacata cctcgctctg ctaatcctgt taccagtggc    8040
tgctgccagt ggcgataagt cgtgtcttac cgggttggac tcaagacgat agttaccgga    8100
taaggcgcag cggtcgggct gaacggggg ttcgtgcaca cagcccagct tggagcgaac      8160
gacctacacc gaactgagat acctacagcg tgagctatga gaaagcgcca cgcttcccga    8220
agggagaaag gcggacaggt atccggtaag cggcagggtc ggaacaggag agcgcacgag    8280
ggagcttcca gggggaaacg cctggtatct ttatagtcct gtcgggtttc gccacctctg    8340
acttgagcgt cgatttttgt gatgctcgtc aggggggcgg agcctatgga aaaacgccag    8400
caacgcggcc ttttacggt tcctggcctt ttgctggcct tttgctcaca tggctcgaca    8460
```

-continued

```
gatct                                                              8465

<210> SEQ ID NO 19
<211> LENGTH: 45
<212> TYPE: DNA
<213> ORGANISM: Artificial Sequence
<220> FEATURE:
<223> OTHER INFORMATION: primer

<400> SEQUENCE: 19
gcgcaccggt gctagcgaat tcggcgacaa gaagggcagc tgcga              45

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
gcgcagatct caggaagccc aggtcctcat                                30

<210> SEQ ID NO 21
<211> LENGTH: 990
<212> TYPE: PRT
<213> ORGANISM: Artificial Sequence
<220> FEATURE:
<223> OTHER INFORMATION: complement factor B protein analog with Fc
      domain

<400> SEQUENCE: 21
```

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

```
Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
            245                 250                 255

Gln Ala Ala Ala Ile Val Leu Asp Pro Ser Gly Ser Met Asn Ile Tyr
        260                 265                 270

Leu Val Leu Asp Gly Ser Gly Ser Ile Gly Ala Ser Asp Phe Thr Gly
    275                 280                 285

Ala Lys Lys Cys Leu Val Asn Leu Ile Glu Lys Val Ala Ser Tyr Gly
290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
    450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
    530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Lys Lys Leu
625                 630                 635                 640
```

```
Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
    690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu Arg Ser Pro Pro
        755                 760                 765

Cys Pro Ser Cys Pro Ala Pro Glu Phe Leu Gly Gly Pro Ser Val Phe
    770                 775                 780

Leu Phe Pro Pro Lys Pro Lys Asp Thr Leu Met Ile Ser Arg Thr Pro
785                 790                 795                 800

Glu Val Thr Cys Val Val Val Asp Val Ser Gln Glu Asp Pro Glu Val
                805                 810                 815

Gln Phe Asn Trp Tyr Val Asp Gly Val Glu Val His Asn Ala Lys Thr
            820                 825                 830

Lys Pro Arg Glu Glu Gln Phe Asn Ser Thr Tyr Arg Val Val Ser Val
        835                 840                 845

Leu Thr Val Leu His Gln Asp Trp Leu Asn Gly Lys Glu Tyr Lys Cys
    850                 855                 860

Lys Val Ser Asn Lys Gly Leu Pro Ser Ser Ile Glu Lys Thr Ile Ser
865                 870                 875                 880

Lys Ala Lys Gly Gln Pro Arg Glu Pro Gln Val Tyr Thr Leu Pro Pro
                885                 890                 895

Ser Gln Glu Glu Met Thr Lys Asn Gln Val Ser Leu Thr Cys Leu Val
            900                 905                 910

Lys Gly Phe Tyr Pro Ser Asp Ile Ala Val Glu Trp Glu Ser Asn Gly
        915                 920                 925

Gln Pro Glu Asn Asn Tyr Lys Thr Thr Pro Pro Val Leu Asp Ser Asp
    930                 935                 940

Gly Ser Phe Phe Leu Tyr Ser Arg Leu Thr Val Asp Lys Ser Arg Trp
945                 950                 955                 960

Gln Glu Gly Asn Val Phe Ser Cys Ser Val Met His Glu Ala Leu His
                965                 970                 975

Asn His Tyr Thr Gln Lys Ser Leu Ser Leu Ser Pro Gly Lys
            980                 985                 990

<210> SEQ ID NO 22
<211> LENGTH: 990
<212> TYPE: PRT
<213> ORGANISM: Artificial Sequence
<220> FEATURE:
<223> OTHER INFORMATION: complement factor B protein analog

<400> SEQUENCE: 22

Met Gly Ser Asn Leu Ser Pro Gln Leu Cys Leu Met Pro Phe Ile Leu
1               5                   10                  15
```

-continued

Gly Leu Leu Ser Gly Val Thr Thr Thr Pro Trp Ser Leu Ala Arg
                20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Ala Ala Ala Ile Val Leu Asp Pro Ser Gly Ser Met Asn Ile Tyr
            260                 265                 270

Leu Val Leu Asp Gly Ser Gly Ser Ile Gly Ala Ser Asp Phe Thr Gly
        275                 280                 285

Ala Lys Lys Ser Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn

```
                435                 440                 445
Glu Gln His Val Phe Lys Val Lys Asp Met Glu Asn Leu Glu Asp Val
        450                 455                 460
Phe Tyr Gln Met Ile Asp Glu Ser Gln Ser Leu Ser Leu Cys Gly Met
465                 470                 475                 480
Val Trp Glu His Arg Lys Gly Thr Asp Tyr His Lys Gln Pro Trp Gln
                485                 490                 495
Ala Lys Ile Ser Val Ile Arg Pro Ser Lys Gly His Glu Ser Cys Met
            500                 505                 510
Gly Ala Val Ser Glu Tyr Phe Val Leu Thr Ala Ala His Cys Phe
            515                 520                 525
Thr Val Asp Asp Lys Glu His Ser Ile Lys Val Ser Val Gly Gly Glu
        530                 535                 540
Lys Arg Asp Leu Glu Ile Glu Val Val Leu Phe His Pro Asn Tyr Asn
545                 550                 555                 560
Ile Asn Gly Lys Lys Glu Ala Gly Ile Pro Glu Phe Tyr Asp Tyr Asp
                565                 570                 575
Val Ala Leu Ile Lys Leu Lys Asn Lys Leu Lys Tyr Gly Gln Thr Ile
            580                 585                 590
Arg Pro Ile Cys Leu Pro Cys Thr Glu Gly Thr Thr Arg Ala Leu Arg
            595                 600                 605
Leu Pro Pro Thr Thr Thr Cys Gln Gln Gln Lys Glu Glu Leu Leu Pro
610                 615                 620
Ala Gln Asp Ile Lys Ala Leu Phe Val Ser Glu Glu Glu Lys Lys Leu
625                 630                 635                 640
Thr Arg Lys Glu Val Tyr Ile Lys Asn Gly Asp Lys Lys Gly Ser Cys
                645                 650                 655
Glu Arg Asp Ala Gln Tyr Ala Pro Gly Tyr Asp Lys Val Lys Asp Ile
            660                 665                 670
Ser Glu Val Val Thr Pro Arg Phe Leu Cys Thr Gly Gly Val Ser Pro
            675                 680                 685
Tyr Ala Asp Pro Asn Thr Cys Arg Gly Asp Ser Gly Gly Pro Leu Ile
        690                 695                 700
Val His Lys Arg Ser Arg Phe Ile Gln Val Gly Val Ile Ser Trp Gly
705                 710                 715                 720
Val Val Asp Val Cys Lys Asn Gln Lys Arg Gln Lys Gln Val Pro Ala
                725                 730                 735
His Ala Arg Asp Phe His Ile Asn Leu Phe Gln Val Leu Pro Trp Leu
            740                 745                 750
Lys Glu Lys Leu Gln Asp Glu Asp Leu Gly Phe Leu Arg Ser Pro Pro
        755                 760                 765
Cys Pro Ser Cys Pro Ala Pro Glu Phe Leu Gly Gly Pro Ser Val Phe
        770                 775                 780
Leu Phe Pro Pro Lys Pro Lys Asp Thr Leu Met Ile Ser Arg Thr Pro
785                 790                 795                 800
Glu Val Thr Cys Val Val Val Asp Val Ser Gln Glu Asp Pro Glu Val
                805                 810                 815
Gln Phe Asn Trp Tyr Val Asp Gly Val Glu Val His Asn Ala Lys Thr
            820                 825                 830
Lys Pro Arg Glu Glu Gln Phe Asn Ser Thr Tyr Arg Val Val Ser Val
        835                 840                 845
Leu Thr Val Leu His Gln Asp Trp Leu Asn Gly Lys Glu Tyr Lys Cys
    850                 855                 860
```

```
Lys Val Ser Asn Lys Gly Leu Pro Ser Ser Ile Glu Lys Thr Ile Ser
865                 870                 875                 880

Lys Ala Lys Gly Gln Pro Arg Glu Pro Gln Val Tyr Thr Leu Pro Pro
            885                 890                 895

Ser Gln Glu Glu Met Thr Lys Asn Gln Val Ser Leu Thr Cys Leu Val
        900                 905                 910

Lys Gly Phe Tyr Pro Ser Asp Ile Ala Val Glu Trp Glu Ser Asn Gly
            915                 920                 925

Gln Pro Glu Asn Asn Tyr Lys Thr Thr Pro Pro Val Leu Asp Ser Asp
        930                 935                 940

Gly Ser Phe Phe Leu Tyr Ser Arg Leu Thr Val Asp Lys Ser Arg Trp
945                 950                 955                 960

Gln Glu Gly Asn Val Phe Ser Cys Ser Val Met His Glu Ala Leu His
            965                 970                 975

Asn His Tyr Thr Gln Lys Ser Leu Ser Leu Ser Pro Gly Lys
        980                 985                 990

<210> SEQ ID NO 23
<211> LENGTH: 990
<212> TYPE: PRT
<213> ORGANISM: Artificial Sequence
<220> FEATURE:
<223> OTHER INFORMATION: complement factor B protein analog

<400> SEQUENCE: 23

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240
```

```
Thr Ile Glu Gly Val Asp Ala Glu Asp Gly His Gly Pro Gly Glu Gln
                245                 250                 255

Gln Ala Ala Ala Ile Val Leu Asp Pro Ser Gly Ser Met Asn Ile Tyr
            260                 265                 270

Leu Val Leu Asp Gly Ser Gly Ser Ile Gly Ala Ser Asp Phe Thr Gly
        275                 280                 285

Ala Lys Lys Ser Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
    450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
    530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655
```

```
Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
    690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asn Phe His Ile Asn Leu Phe Gln Val Leu Pro Trp Leu
            740                 745                 750

Lys Glu Lys Leu Gln Asp Glu Asp Leu Gly Phe Leu Arg Ser Pro Pro
        755                 760                 765

Cys Pro Ser Cys Pro Ala Pro Glu Phe Leu Gly Gly Pro Ser Val Phe
    770                 775                 780

Leu Phe Pro Pro Lys Pro Lys Asp Thr Leu Met Ile Ser Arg Thr Pro
785                 790                 795                 800

Glu Val Thr Cys Val Val Val Asp Val Ser Gln Glu Asp Pro Glu Val
                805                 810                 815

Gln Phe Asn Trp Tyr Val Asp Gly Val Glu Val His Asn Ala Lys Thr
            820                 825                 830

Lys Pro Arg Glu Glu Gln Phe Asn Ser Thr Tyr Arg Val Val Ser Val
        835                 840                 845

Leu Thr Val Leu His Gln Asp Trp Leu Asn Gly Lys Glu Tyr Lys Cys
    850                 855                 860

Lys Val Ser Asn Lys Gly Leu Pro Ser Ser Ile Glu Lys Thr Ile Ser
865                 870                 875                 880

Lys Ala Lys Gly Gln Pro Arg Glu Pro Gln Val Tyr Thr Leu Pro Pro
                885                 890                 895

Ser Gln Glu Glu Met Thr Lys Asn Gln Val Ser Leu Thr Cys Leu Val
            900                 905                 910

Lys Gly Phe Tyr Pro Ser Asp Ile Ala Val Glu Trp Glu Ser Asn Gly
        915                 920                 925

Gln Pro Glu Asn Asn Tyr Lys Thr Thr Pro Pro Val Leu Asp Ser Asp
    930                 935                 940

Gly Ser Phe Phe Leu Tyr Ser Arg Leu Thr Val Asp Lys Ser Arg Trp
945                 950                 955                 960

Gln Glu Gly Asn Val Phe Ser Cys Ser Val Met His Glu Ala Leu His
                965                 970                 975

Asn His Tyr Thr Gln Lys Ser Leu Ser Leu Ser Pro Gly Lys
            980                 985                 990

<210> SEQ ID NO 24
<211> LENGTH: 6860
<212> TYPE: DNA
<213> ORGANISM: Artificial Sequence
<220> FEATURE:
<223> OTHER INFORMATION: expression construct

<400> SEQUENCE: 24
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
```

```
gtcattagtt catagcccat atatggagtt ccgcgttaca taacttacgg taaatggccc      240
gcctggctga ccgcccaacg acccccgccc attgacgtca ataatgacgt atgttcccat      300
agtaacgcca atagggactt tccattgacg tcaatgggtg gagtatttac ggtaaactgc      360
ccacttggca gtacatcaag tgtatcatat gccaagtccg cccctattg acgtcaatga       420 cggtaaatgg cccgcctggc attatgccca gtacatgacc ttacgggact tcctacttg      480 gcagtacatc tacgtattag tcatcgctat taccatggtg atgcggtttt ggcagtacac      540
caatgggcgt ggatagcggt ttgactcacg gggatttcca agtctccacc ccattgacgt      600
caatgggagt ttgttttggc accaaaatca acgggacttt ccaaaatgtc gtaataaccc      660
cgccccgttg acgcaaatgg gcggtaggcg tgtacggtgg gaggtctata taagcagagc      720
tcgtttagtg aaccgtcaga tcactagaag ctttattgcg gtagtttatc acagttaaat      780
tgctaacgca gtcagtgctt ctgacacaac agtctcgaac ttaagctgca gaagttggtc      840
gtgaggcact gggcaggtaa gtatcaaggt tacaagacag gtttaaggag accaatagaa      900
actgggcttg tcgagacaga agagactctt gcgtttctga taggcaccta ttggtcttac      960
tgacatccac tttgcctttc tctccacagg tgtccactcc cagttcaatt acagctctta     1020
aggctagagt acttaatacg actcactata ggctagcgcc accatgggct ccaacctgtc     1080
cccccagctg tgcctgatgc ctttcatcct gggcctgctg tctggcggcg tgaccaccac     1140
cccttggtcc ctgccaggc ctcagggctc ctgctccctg gagggcgtgg agatcaaggg      1200
cggctccttc cggctgctgc aggaaggcca ggctctggag tacgtgtgcc cttccggctt     1260 ctaccttac cctgtgcaga caaggacctg taggtccacc ggctcttggt ccacactgaa      1320
aacccaggac cagaaaaccg tccggaaggc cgagtgccgg ccatccact gccctcggcc      1380 tcacgacttc gagaacggcg agtactggcc tcggtcccct tactacaacg tgtccgacga     1440
gatctccttc cactgctacg acggctacac cctgcggggc tccgccaaca ggacctgcca     1500
ggtcaacggc cggtggtccg gccagaccgc catctgcgac aacggcgctg gctactgctc     1560
caaccctggc atccctatcg gcacccggaa ggtcggctcc cagtaccggc tggaggactc     1620
cgtgacctac cactgctcca gaggcctgac cctgagagc tcccagcggc gcacctgtca      1680
ggaaggtggc agctggtctg caccgaacc atcttgccag gactccttca tgtacgacac      1740
ccctcaggaa gtggccgagg ccttcctgtc ctccctgacc gagacaatcg agggcgtgga     1800
cgccgaggat ggccacggcc ctggcgagca gcaggccgct gccatcgtgc tggacccctc     1860
cggctccatg aacatctacc tggtgctgga cggctccggc agcatcggcg cctccgactt     1920
caccggcgcc aagaagagcc tggtcaacct gatcgagaag gtggcctcct acggcgtgaa     1980
gcctagatac ggcctggtga cctacgccac ctaccctaag atctgggtga aggtgtccga     2040
ggccgactcc tccaacgccg actgggtgac caagcagctg aacgagatca actacgagga     2100
ccacaagctg aagtccggca ccaacaccaa gaaggccctg caggccgtct actccatgat     2160
gtcctggcct gacgacgtgc ctcctgaggg ctggaaccgg accggcacg tgattatcct       2220 gatgaccgac ggcctgcaca acatgggcgg cgaccctatc accgtgatcg acgagatccg     2280
ggacctgctg tacatcggca aggaccggaa gaacccgg gaggactacc tggacgtgta       2340
cgtgttcggc gtgggccctc tggtgaacca ggtcaacatc aacgccctgg cctccaagaa     2400
ggacaacgag cagcacgtgt tcaaggtcaa ggacatggag aacctggagg acgtgttcta     2460
ccagatgatc gatgagtccc agtccctgag cctgtgcgc atgtgataag ctagcctcga      2520
gaattcacgc gtggtaccctc tagagtcgac cctctagggc ggccaattcc gcccctctcc    2580
```

```
ctcccccccc cctaacgtta ctggccgaag ccgcttggaa taaggccggt gtgcgtttgt    2640
ctatatgtta ttttccacca tattgccgtc ttttggcaat gtgagggccc ggaaacctgg    2700
ccctgtcttc ttgacgagca ttcctagggg tctttcccct ctcgccaaag gaatgcaagg    2760
tctgttgaat gtcgtgaagg aagcagttcc tctggaagct tcttgaagac aaacaacgtc    2820
tgtagcgacc ctttgcaggc agcggaaccc cccacctggc gacaggtgcc tctgcggcca    2880
aaagccacgt gtataagata cacctgcaaa ggcggcacaa ccccagtgcc acgttgtgag    2940
ttggatagtt gtggaaagag tcaaatggct ctcctcaagc gtattcaaca aggggctgaa    3000
ggatgcccag aaggtacccc attgtatggg atctgatctg gggcctcggt gcacatgctt    3060
tacatgtgtt tagtcgaggt taaaaaaacg tctaggcccc ccgaaccacg gggacgtggt    3120
tttcctttga aaaacacgat gataagcttg ccacaacccg ggataattcc tgcagccaat    3180
atgggatcgg ccattgaaca agatggattg cacgcaggtt ctccggccgc ttgggtggag    3240
aggctattcg gctatgactg ggcacaacag acaatcggct gctctgatgc cgccgtgttc    3300
cggctgtcag cgcaggggcg cccggttctt tttgtcaaga ccgacctgtc cggtgccctg    3360
aatgaactgc aggacgaggc agcgcggcta tcgtggctgg ccacgacggg cgttccttgc    3420
gcagctgtgc tcgacgttgt cactgaagcg ggaagggact ggctgctatt gggcgaagtg    3480
ccggggcagg atctcctgtc atctcacctt gctcctgccg agaaagtatc catcatggct    3540
gatgcaatgc ggcggctgca tacgcttgat ccggctacct gcccattcga ccaccaagcg    3600
aaacatcgca tcgagcgagc acgtactcgg atggaagccg gtcttgtcga tcaggatgat    3660
ctggacgaag agcatcaggg gctcgcgcca gccgaactgt tcgccaggct caaggcgcgc    3720
atgcccgacg gcgatgatct cgtcgtgacc catggcgatg cctgcttgcc gaatatcatg    3780
gtggaaaatg gccgcttttc tggattcatc gactgtggcc ggctgggtgt ggcggaccgc    3840
tatcaggaca tagcgttggc tacccgtgat attgctgaag agcttggcgg cgaatgggct    3900
gaccgcttcc tcgtgcttta cggtatcgcc gctcccgatt cgcagcgcat cgccttctat    3960
cgccttcttg acgagttctt ctgagggat caattctggg cggcctcgag aataaacaat    4020
cattattttc attggatctg tgtgttggtt ttttgtgtgg gcttggggga gggggaggcc    4080
agaatgactc caagagctac aggaaggcag gtcagagacc ccactggaca acagtggct    4140
ggactctgca ccataacaca caatcaacag gggagtgagc tggatcgagc tgctcgagat    4200
ccgggctggc gtaatagcga agaggcccgc accgatcgcc cttcccaaca gttgcgcagc    4260
ctgaatggcg aatggacgcg ccctgtagcg gcgcattaag cgcggcgggt gtggtggtta    4320
cgcgcagcgt gaccgctaca cttgccagcg ccctagcgcc cgctcctttc gctttcttcc    4380
cttcctttct cgccacgttc gccggctttc cccgtcaagc tctaaatcgg ggctccctt    4440
tagggttccg atttagtgct ttacggcacc tcgaccccaa aaaacttgat tagggtgatg    4500
gttcacgtag tgggccatcg ccctgataga cggtttttcg ccctttgacg ttggagtcca    4560
cgttctttaa tagtggactc ttgttccaaa ctggaacaac actcaaccct atctcggtct    4620
attcttttga tttataaggg attttgccga tttcggccta ttggttaaaa atgagctga    4680
tttaacaaaa atttaacgcg aattttaaca aaatattaac gcttacaatt tcctgatgcg    4740
gtattttctc cttacgcatc tgtgcggtat tcacaccgc atatggtgca ctctcagtac    4800
aatctgctct gatgccgcat agttaagcca gccccgacac ccgccaacac ccgctgacgc    4860
gccctgacgg gcttgtctgc tcccggcatc cgcttacaga caagctgtga ccgtctccgg    4920
```

| | |
|---|---|
| gagctgcatg tgtcagaggt tttcaccgtc atcaccgaaa cgcgcgagac gaaagggcct | 4980 |
| cgtgatacgc ctattttat aggttaatgt catgataata atggtttctt agacgtcagg | 5040 |
| tggcactttt cggggaaatg tgcgcggaac ccctatttgt ttatttttct aaatacattc | 5100 |
| aaatatgtat ccgctcatga acaataacc ctgataaatg cttcaataat attgaaaaag | 5160 |
| gaagagtatg agtattcaac atttccgtgt cgcccttatt ccctttttg cggcattttg | 5220 |
| ccttcctgtt tttgctcacc cagaaacgct ggtgaaagta aaagatgctg aagatcagtt | 5280 |
| gggtgcacga gtgggttaca tcgaactgga tctcaacagc ggtaagatcc ttgagagttt | 5340 |
| tcgccccgaa gaacgttttc caatgatgag cacttttaaa gttctgctat gtggcgcggt | 5400 |
| attatcccgt attgacgccg ggcaagagca actcggtcgc cgcatacact attctcagaa | 5460 |
| tgacttggtt gagtactcac cagtcacaga aaagcatctt acggatggca tgacagtaag | 5520 |
| agaattatgc agtgctgcca taaccatgag tgataacact gcggccaact tacttctgac | 5580 |
| aacgatcgga ggaccgaagg agctaaccgc ttttttgcac aacatggggg atcatgtaac | 5640 |
| tcgccttgat cgttgggaac cggagctgaa tgaagccata ccaaacgacg agcgtgacac | 5700 |
| cacgatgcct gtagcaatgg caacaacgtt gcgcaaacta ttaactggcg aactacttac | 5760 |
| tctagcttcc cggcaacaat taatagactg gatggaggcg gataaagttg caggaccact | 5820 |
| tctgcgctcg gcccttccgg ctggctggtt tattgctgat aaatctggag ccggtgagcg | 5880 |
| tgggtctcgc ggtatcattg cagcactggg gccagatggt aagccctccc gtatcgtagt | 5940 |
| tatctacacg acggggagtc aggcaactat ggatgaacga aatagacaga tcgctgagat | 6000 |
| aggtgcctca ctgattaagc attggtaact gtcagaccaa gtttactcat atatacttta | 6060 |
| gattgattta aaacttcatt tttaatttaa aaggatctag gtgaagatcc ttttgataa | 6120 |
| tctcatgacc aaaatccctt aacgtgagtt ttcgttccac tgagcgtcag acccccgtaga | 6180 |
| aaagatcaaa ggatcttctt gagatccttt ttttctgcgc gtaatctgct gcttgcaaac | 6240 |
| aaaaaaacca ccgctaccag cggtggtttg tttgccggat caagagctac caactctttt | 6300 |
| tccgaaggta actggcttca gcagagcgca gataccaaat actgttcttc tagtgtagcc | 6360 |
| gtagttaggc caccacttca agaactctgt agcaccgcct acatacctcg ctctgctaat | 6420 |
| cctgttacca gtggctgctg ccagtggcga taagtcgtgt cttaccgggt tggactcaag | 6480 |
| acgatagtta ccggataagg cgcagcggtc gggctgaacg ggggggttcgt gcacacagcc | 6540 |
| cagcttggag cgaacgacct acaccgaact gagatacctat cagcgtgagc tatgagaaag | 6600 |
| cgccacgctt cccgaaggga gaaaggcgga caggtatccg gtaagcggca gggtcggaac | 6660 |
| aggagagcgc acgagggagc ttccaggggg aaacgcctgg tatctttata gtcctgtcgg | 6720 |
| gtttcgccac ctctgacttg agcgtcgatt tttgtgatgc tcgtcagggg gcggagcct | 6780 |
| atggaaaaac gccagcaacg cggccttttt acggttcctg gccttttgct ggccttttgc | 6840 |
| tcacatggct cgacagatct | 6860 |

<210> SEQ ID NO 25
<211> LENGTH: 8435
<212> TYPE: DNA
<213> ORGANISM: Artificial Sequence
<220> FEATURE:
<223> OTHER INFORMATION: expression construct

<400> SEQUENCE: 25

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |

```
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat     300
agtaacgcca atagggactt tccattgacg tcaatgggtg gagtatttac ggtaaactgc    360
ccacttggca gtacatcaag tgtatcatat gccaagtccg cccctattg acgtcaatga     420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660 cgcccgttg acgcaaatgg gcggtaggcg tgtacggtgg gaggtctata taagcagagc     720
tcgtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt acttaatacg actcactata ggctagctcc tgcccaggc ccagcttctc     1080 tcctgccttc caacgccatg gctccaacc tgtcccccca gctgtgcctg atgcctttca      1140
tcctgggcct gctgtctggc ggcgtgacca ccacccttg gtccctggcc aggcctcagg      1200
gctcctgctc cctggagggc gtggagatca agggcggctc cttccggctg ctgcaggaag    1260
gccaggctct ggagtacgtg tgcccttccg gcttctaccc ttaccctgtg cagacaagga    1320
cctgtaggtc caccggctct tggtccacac tgaaaaccca ggaccagaaa accgtccgga    1380
aggccgagtg ccgggccatc cactgccctc ggcctcacga cttcgagaac ggcgagtact    1440
ggcctcggtc cccttactac aacgtgtccg acgagatctc cttccactgc tacgacggct    1500 acacccctgcg gggctccgcc aacaggacct gccaggtcaa cggccggtgg tccggccaga    1560
ccgccatctg cgacaacggc gctggctact gctccaaccc tggcatccct atcggcaccc    1620
ggaaggtcgg ctcccagtac cggctggagg actccgtgac ctaccactgc tccagaggcc    1680 tgacccctgag aggctcccag cggcgcacct gtcaggaagg tggcagctgg tctggcaccg    1740
aaccatcttg ccaggactcc ttcatgtacg acacccctca ggaagtggcc gaggccttcc    1800
tgtcctccct gaccgagaca atcgagggcg tggacgccga ggatggccac ggccctggcg    1860
agcagcaggc cgctgccatc gtgctggacc cctccggctc catgaacatc tacctggtgc    1920 tggacgctc cggcagcatc ggcgcctccg acttcaccgg cgccaagaag agcctggtca    1980
acctgatcga gaaggtggcc tcctacggcg tgaagcctag atacggcctg gtgacctacg    2040
ccacctaccc taagatctgg gtgaaggtgt ccgaggccga ctcctccaac gccgactggg    2100
tgaccaagca gctgaacgag atcaactacg aggaccacaa gctgaagtcc ggcaccaaca    2160
ccaagaaggc cctgcaggcc gtctactcca tgatgtcctg gcctgacgac gtgcctcctg    2220
agggctggaa ccggacccgg cacgtgatta tcctgatgac cgacggcctg cacaacatgg    2280
gcggcgaccc tatcaccgtg atcgacgaga tccgggacct gctgtacatc ggcaaggacc    2340
ggaagaaccc tcgggaggac tacctggacg tgtacgtgtt cggcgtgggc ctctctgtga    2400
accaggtcaa catcaacgcc ctggcctcca agaaggacaa cgagcagcac gtgttcaagg    2460
```

```
tcaaggacat ggagaacctg gaggacgtgt tctaccagat gatcgatgag tcccagtccc   2520
tgagcctgtg cggcatggtc tgggagcacc gcaagggaac cgactaccac aagcagcctt   2580
ggcaggccaa gatctccgtg atccggcctt ccaagggcca cgagtcctgc atgggcgccg   2640
tggtgtccga gtacttcgtg ctgaccgccg ctcactgctt caccgtggac gacaaggaac   2700
actccatcaa agtctccgtg ggcggcgaga agcgggacct ggagatcgag gtggtgctgt   2760
tccaccctaa ctacaacatc aacggcaaga aggaagccgg catccctgag ttctacgact   2820
acgacgtggc cctgatcaag ctgaagaata agctgaagta tggccagacc atccggccta   2880
tctgcctgcc ttgcaccgag ggcaccacca gggccctgcg gctgcctcct accaccacct   2940
gccagcagca gaaggaagag ctgctgcctg cccaggacat caaggccctg ttcgtgtccg   3000
aggaagagaa gaagctgacc cggaaggaag tgtacatcaa gaacggcgac aagaagggca   3060
gctgcgagcg ggacgcccag tacgccctg gctacgataa ggtcaaggat atctccgagg   3120
tggtgacccc tcggttcctg tgcaccggcg gagtgtcccc ctacgccgac cctaacacct   3180
gcagaggcga ctctggcggc cctctgatcg tgcacaagcg gtcccggttc atccaggtcg   3240
gcgtgatctc ctggggcgtg gtggacgtgt gcaagaacca gaagcggcag aagcaggtcc   3300
ccgcccacgc ccgggacttc cacatcaacc tgttccaggt gctgccttgg ctgaaggaaa   3360
agctgcagga tgaggacctg ggcttcctga gatccaacac caaggtggac aagagagttg   3420
agtccaaata tggtccccca tccccatcat ccccagcacc tgagttcctg ggggaccat   3480
cagtcttcct gttcccccca aacccaagg acactctcat gatctcccgg acccctgagg   3540
tcacgtgcgt ggtggtggac gtgagccagg aagaccccga ggtccagttc aactggtacg   3600
tggatggcgt ggaggtgcat aatgccaaga caaagccgcg ggaggagcag ttcaacagca   3660
cgtaccgtgt ggtcagcgtc ctcaccgtcc tgcaccagga ctggctgaac ggcaaggagt   3720
acaagtgcaa ggtctccaac aaaggcctcc cgtcctccat cgagaaaacc atctccaaag   3780
ccaaagggca gccccgagag ccacaggtgt acaccctgcc cccatcccag gaggagatga   3840
ccaagaacca ggtcagcctg acctgcctgg tcaaaggctt ctaccccagc gacatcgccg   3900
tggagtggga gagcaatggg cagccggaga acaactacaa gaccacgcct cccgtgctgg   3960
actccgacgg ctccttcttc ctctacagca ggctaaccgt ggacaagagc aggtggcagg   4020
aggggaatgt cttctcatgc tccgtgatgc atgaggctct gcacaaccac tacacacaga   4080
agagcctctc cctgtctctg ggtaaatgag tctagacagg ggcgtgggat tgacgcccct   4140
ctccctcccc cccccctaac gttactggcc gaagccgctt ggaataaggc cggtgtgcgt   4200
ttgtctatat gttatttcc accatattgc cgtcttttgg caatgtgagg gcccggaaac   4260
ctggccctgt cttcttgacg agcattccta ggggtctttc ccctctcgcc aaaggaatgc   4320
aaggtctgtt gaatgtcgtg aaggaagcag ttcctctgga agcttcttga agacaaacaa   4380
cgtctgtagc gacccttgc aggcagcgga accccccacc tggcgacagg tgcctctgcg   4440
gccaaaagcc acgtgtataa gatacacctg caaaggcggc acaaccccag tgccacgttg   4500
tgagttggat agttgtggaa agagtcaaat ggctctcctc aagcgtattc aacaagggc   4560
tgaaggatgc ccagaaggta ccccattgta tgggatctga tctggggcct cggtgcacat   4620
gctttacatg tgtttagtcg aggttaaaaa aacgtctagg ccccccgaac cacggggacg   4680
tggttttcct ttgaaaaaca cgatgataag cttgccacaa cccgggataa ttcctgcagc   4740
caatatggga tcgccattg aacaagatgg attgcacgca ggttctccgg ccgcttgggt   4800
ggagaggcta ttcggctatg actgggcaca acagacaatc ggctgctctg atgccgccgt   4860
```

```
gttccggctg tcagcgcagg ggcgcccggt tcttttgtc aagaccgacc tgtccggtgc   4920
cctgaatgaa ctgcaggacg aggcagcgcg gctatcgtgg ctggccacga cgggcgttcc   4980
ttgcgcagct gtgctcgacg ttgtcactga agcgggaagg gactggctgc tattgggcga   5040
agtgccgggg caggatctcc tgtcatctca ccttgctcct gccgagaaag tatccatcat   5100
ggctgatgca atgcggcggc tgcatacgct tgatccggct acctgcccat cgaccacca   5160
agcgaaacat cgcatcgagc gagcacgtac tcggatggaa gccggtcttg tcgatcagga   5220
tgatctggac gaagagcatc aggggctcgc gccagccgaa ctgttcgcca ggctcaaggc   5280
gcgcatgccc gacggcgatg atctcgtcgt gacccatggc gatgcctgct tgccgaatat   5340
catggtggaa aatggccgct tttctggatt catcgactgt ggccggctgg gtgtggcgga   5400
ccgctatcag gacatagcgt tggctacccg tgatattgct gaagagcttg gcggcgaatg   5460
ggctgaccgc ttcctcgtgc tttacggtat cgccgctccc gattcgcagc gcatcgcctt   5520
ctatcgcctt cttgacgagt tcttctgagg ggatcaattc tctagtcgac ccgggcggcc   5580
tcgagaataa acaatcatta ttttcattgg atctgtgtgt tggttttttg tgtgggcttg   5640
ggggagggg aggccagaat gactccaaga gctacaggaa ggcaggtcag agaccccact   5700
ggacaaacag tggctggact ctgcaccata acacacaatc aacaggggag tgagctggat   5760
cgagctgctc gagatccggg ctggcgtaat agcgaagagg cccgcaccga tcgcccttcc   5820
caacagttgc gcagcctgaa tggcgaatgg acgcgccctg tagcggcgca ttaagcgcgg   5880
cgggtgtggt ggttacgcgc agcgtgaccg ctacacttgc cagcgcccta gcgcccgctc   5940
ctttcgcttt cttcccttcc tttctcgcca cgttcgccgg ctttccccgt caagctctaa   6000
atcgggggct ccctttaggg ttccgattta gtgctttacg gcacctcgac cccaaaaaac   6060
ttgattaggg tgatggttca cgtagtgggc catcgccctg atagacggtt tttcgccctt   6120
tgacgttgga gtccacgttc tttaatagtg actcttgtt ccaaactgga caaacactca   6180
accctatctc ggtctattct tttgatttat aagggatttt gccgatttcg gcctattggt   6240
taaaaaatga gctgatttaa caaaaattta acgcgaattt taacaaaata ttaacgctta   6300
caatttcctg atgcggtatt ttctccttac gcatctgtgc ggtatttcac accgcatatg   6360
gtgcactctc agtacaatct gctctgatgc cgcatagtta agccagcccc gacacccgcc   6420
aacacccgct gacgcgccct gacgggcttg tctgctcccg gcatccgctt acagacaagc   6480
tgtgaccgtc tccgggagct gcatgtgtca gaggttttca ccgtcatcac cgaaacgcgc   6540
gagacgaaag gcctcgtgat acgcctattt ttataggtt aatgtcatga taataatggt   6600
ttcttagacg tcaggtggca cttttcgggg aaatgtgcgc ggaacccca tttgtttatt   6660
tttctaaata cattcaaata tgtatccgct catgagacaa taaccctgat aaatgcttca   6720
ataatattga aaaggaaga gtatgagtat tcaacatttc cgtgtcgccc ttattccctt   6780
ttttgcggca ttttgccttc ctgtttttgc tcacccagaa acgctggtga agtaaaga    6840
tgctgaagat cagttgggtg cacgagtggg ttacatcgaa ctggatctca acagcggtaa   6900
gatccttgag agttttcgcc ccgaagaacg ttttccaatg atgagcactt ttaaagttct   6960
gctatgtggc gcggtattat cccgtattga cgccgggcaa gagcaactcg gtcgccgcat   7020
acactattct cagaatgact tggttgagta ctcaccagtc acagaaaagc atcttacgga   7080
tggcatgaca gtaagagaat tatgcagtgc tgccataacc atgagtgata acactgcggc   7140
caacttactt ctgacaacga tcggaggacc gaaggagcta accgcttttt tgcacaacat   7200
```

-continued

```
ggggatcat gtaactcgcc ttgatcgttg ggaaccggag ctgaatgaag ccataccaaa   7260
cgacgagcgt gacaccacga tgcctgtagc aatggcaaca acgttgcgca aactattaac   7320
tggcgaacta cttactctag cttcccggca acaattaata gactggatgg aggcggataa   7380
agttgcagga ccacttctgc gctcggccct tccggctggc tggtttattg ctgataaatc   7440
tggagccggt gagcgtgggt ctcgcggtat cattgcagca ctggggccag atggtaagcc   7500
ctcccgtatc gtagttatct acacgacggg gagtcaggca actatggatg aacgaaatag   7560
acagatcgct gagataggtg cctcactgat taagcattgg taactgtcag accaagttta   7620
ctcatatata ctttagattg atttaaaact tcatttttaa tttaaaagga tctaggtgaa   7680
gatcctttt gataatctca tgaccaaaat cccttaacgt gagttttcgt tccactgagc    7740
gtcagacccc gtagaaaaga tcaaaggatc ttcttgagat cctttttttc tgcgcgtaat   7800
ctgctgcttg caaacaaaaa aaccaccgct accagcggtg gtttgtttgc cggatcaaga   7860
gctaccaact ctttttccga aggtaactgg cttcagcaga gcgcagatac caaatactgt   7920
tcttctagtg tagccgtagt taggccacca cttcaagaac tctgtagcac cgcctacata   7980
cctcgctctg ctaatcctgt taccagtggc tgctgccagt ggcgataagt cgtgtcttac   8040
cgggttggac tcaagacgat agttaccgga taaggcgcag cggtcgggct gaacggggg    8100
ttcgtgcaca cagcccagct tggagcgaac gacctacacc gaactgagat acctacagcg   8160
tgagctatga gaaagcgcca cgcttcccga agggagaaag gcggacaggt atccggtaag   8220
cggcagggtc ggaacaggag agcgcacgag ggagcttcca gggggaaacg cctggtatct   8280
ttatagtcct gtcgggtttc gccacctctg acttgagcgt cgatttttgt gatgctcgtc   8340
agggggggcgg agcctatgga aaaacgccag caacgcggcc ttttacggtt cctggccttt   8400
tgctggcct tttgctcaca tggctcgaca gatct                               8435
```

<210> SEQ ID NO 26
<211> LENGTH: 1003
<212> TYPE: PRT
<213> ORGANISM: Artificial Sequence
<220> FEATURE:
<223> OTHER INFORMATION: complement factor B protein analog

<400> SEQUENCE: 26

```
Met Gly Ser Asn Leu Ser Pro Gln Leu Cys Leu Met Pro Phe Ile Leu
 1               5                  10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140
```

```
Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
            165                 170                 175

Val Gly Ser Gln Tyr Arg Leu Glu Asp Ser Val Thr Tyr His Cys Ser
        180                 185                 190

Arg Gly Leu Thr Leu Arg Gly Ser Gln Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Ala Ala Ala Ile Val Leu Asp Pro Ser Gly Ser Met Asn Ile Tyr
            260                 265                 270

Leu Val Leu Asp Gly Ser Gly Ser Ile Gly Ala Ser Asp Phe Thr Gly
            275                 280                 285

Ala Lys Lys Ser Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
    355                 360                 365

Pro Asp Asp Val Pro Glu Gly Trp Asn Arg Thr Arg His Val Ile
370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
    530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
```

```
                565                 570                 575
Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
    690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu Arg Ser Asn Thr
        755                 760                 765

Lys Val Asp Lys Arg Val Glu Ser Lys Tyr Gly Pro Pro Ser Pro Ser
    770                 775                 780

Ser Pro Ala Pro Glu Phe Leu Gly Gly Pro Ser Val Phe Leu Phe Pro
785                 790                 795                 800

Pro Lys Pro Lys Asp Thr Leu Met Ile Ser Arg Thr Pro Glu Val Thr
                805                 810                 815

Cys Val Val Val Asp Val Ser Gln Glu Asp Pro Glu Val Gln Phe Asn
            820                 825                 830

Trp Tyr Val Asp Gly Val Glu Val His Asn Ala Lys Thr Lys Pro Arg
        835                 840                 845

Glu Glu Gln Phe Asn Ser Thr Tyr Arg Val Val Ser Val Leu Thr Val
    850                 855                 860

Leu His Gln Asp Trp Leu Asn Gly Lys Glu Tyr Lys Cys Lys Val Ser
865                 870                 875                 880

Asn Lys Gly Leu Pro Ser Ser Ile Glu Lys Thr Ile Ser Lys Ala Lys
                885                 890                 895

Gly Gln Pro Arg Glu Pro Gln Val Tyr Thr Leu Pro Pro Ser Gln Glu
            900                 905                 910

Glu Met Thr Lys Asn Gln Val Ser Leu Thr Cys Leu Val Lys Gly Phe
        915                 920                 925

Tyr Pro Ser Asp Ile Ala Val Glu Trp Glu Ser Asn Gly Gln Pro Glu
    930                 935                 940

Asn Asn Tyr Lys Thr Thr Pro Pro Val Leu Asp Ser Asp Gly Ser Phe
945                 950                 955                 960

Phe Leu Tyr Ser Arg Leu Thr Val Asp Lys Ser Arg Trp Gln Glu Gly
                965                 970                 975

Asn Val Phe Ser Cys Ser Val Met His Glu Ala Leu His Asn His Tyr
            980                 985                 990
```

```
Thr Gln Lys Ser Leu Ser Leu Ser  Leu Gly Lys
        995                 1000

<210> SEQ ID NO 27
<211> LENGTH: 238
<212> TYPE: PRT
<213> ORGANISM: Homo sapiens

<400> SEQUENCE: 27

Ser Asn Thr Lys Val Asp Lys Arg Val Glu Ser Lys Tyr Gly Pro Pro
1               5                   10                  15

Cys Pro Ser Cys Pro Ala Pro Glu Phe Leu Gly Gly Pro Ser Val Phe
            20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser Gln Glu Asp Pro Glu Val
        50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
            115                 120                 125

Lys Ala Lys Gly Gln Pro Arg Glu Pro Gln Val Tyr Thr Leu Pro Pro
        130                 135                 140

Ser Gln Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Arg Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235
```